United States Patent
Gillman et al.

(10) Patent No.: US 7,091,202 B2
(45) Date of Patent: Aug. 15, 2006

(54) 4-ARYLSPIROCYCLOALKYL-2-AMINOPYRIMIDINE CARBOXAMIDE KCNQ POTASSIUM CHANNEL MODULATORS

(75) Inventors: Kevin W. Gillman, Madison, CT (US); Dharmpal S. Dodd, Princeton, NJ (US); John E. Starrett, Jr., Middletown, CT (US); Danielle Bocchino, Philadelphia, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 8 days.

(21) Appl. No.: 11/222,123

(22) Filed: Sep. 8, 2005

(65) Prior Publication Data

US 2006/0063790 A1 Mar. 23, 2006

Related U.S. Application Data

(60) Provisional application No. 60/610,115, filed on Sep. 15, 2004.

(51) Int. Cl.
*C07D 239/42* (2006.01)
*C07D 401/04* (2006.01)
*C07D 401/08* (2006.01)
*C07D 413/12* (2006.01)
*A61K 31/505* (2006.01)

(52) U.S. Cl. .............. 514/235.8; 514/255.05; 514/256; 514/275; 544/122; 544/295; 544/296; 544/331

(58) Field of Classification Search ......... 544/122, 544/295, 296, 331; 514/235.8, 255.05, 256, 514/275

See application file for complete search history.

(56) References Cited

U.S. PATENT DOCUMENTS 4,931,560 A * 6/1990 Hubele .............. 544/315
5,811,428 A    9/1998 Suto et al.
6,281,219 B1 * 8/2001 Cuccia et al. ......... 514/256

OTHER PUBLICATIONS

Gribkoff et al., Effects of Channel Modulators on Cloned Large-Conductance Calcium-Activated Potassium Channels, Molecular Pharmacology, 50(1), pp. 206-217, 1996.*
Wang et al., KCNQ2 and KCNQ3 Potassium Channel Subunits: Molecular Correlates of the M-Channel, Science, vol. 282, pp. 1890-1893, 1998.*
Robbins, KCNQ potassium channels: physiology, pathophysiology, and pharmacology, Pharmacology & Therapeutics, 90, pp. 1-19, 2001.*
Ulrich, Crystallization, Kirk-Othmer Encyclopedia of Chemical Technology, vol. 8, pp. 113-120, (http://www.mrw.interscience.wiley.com/kirk/articles/crysrous.a01/sect4-fs.html) Aug. 2002.*
West, Solid Solutions, Solid state chemistry and it's applications, Wiley, New York, pp. 358 and 365, 1988.*
Vippagunta et al., Crystalline solids, Advanced Drug Delivery Reviews, 48 (2001), pp. 3-26, 2001.*

* cited by examiner

*Primary Examiner*—Deepak Rao
(74) *Attorney, Agent, or Firm*—James Epperson

(57) ABSTRACT

The invention encompasses compounds of Formula I, which are blockers of KCNQ channels. Blockers of KCNQ channels are known to enchance cognition in laboratory animals. The invention includes, salts, solvates, compositions, and methods of use

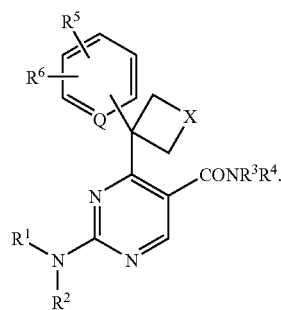

10 Claims, No Drawings

US 7,091,202 B2

4-ARYLSPIROCYCLOALKYL-2-AMINOPYRIMIDINE CARBOXAMIDE KCNQ POTASSIUM CHANNEL MODULATORS

CROSS-REFERENCE TO RELATED APPLICATIONS

This application claims the benefit of U.S. Provisional Application Ser. No. 60/610,115 filed Sep. 15, 2004.

BACKGROUND OF THE INVENTION

Potassium ($K^+$) channels are a diverse class of ion channels and have several critical roles in cell function. One role is in neurons, where $K^+$ channels are responsible, in part, for determining cell excitability by contributing to membrane repolarization following depolarization, resting membrane potential, and regulation of neurotransmitter release. The M-current, measured by electrophysiology recording methods and by pharmacology, has been described as a dominant conductance in controlling neuronal excitability. Pharmacological activation or suppression of M currents by small molecules could have profound effects in controlling neuronal excitability. Recently, Wang reported that co-assembly of the KCNQ2 and KCNQ3 potassium channels underlies the native M-current in neurons (Wang et al., *Science* 1998, 282, 1890–1893).

Compounds that block KCNQ channels and M current, including linopirdine and XE-991, demonstrate cognition enhancing effects. The compounds act by increasing the stimulus-evoked release of a number of neurotransmitters in the central nervous system. See Wang et al. *Science* 1998, 282, 1890; Lamas *Eur. J. Neurosci.* 1997, 9, 607; Schnee and Brown *J. Pharmacol. Exp. Ther.* 1998, 286, 709; Zaczek et al. *J. Pharmacol Exp. Ther.* 1998, 285, 724 and references cited by these papers.

At the time linopirdine and XE-991 were discovered, they were not known to be KCNQ blockers and were not optimized for KCNQ inhibition or selectivity. Thus, potent and selective KCNQ blockers offer a promising opportunity for treating impairments of memory or cognition.

2-Amino-5-carboxamidopyrimidines have been disclosed. See Suto et al. U.S. Pat. No. 5,811,428. Nothing in this reference discloses or suggests the novel compounds of this application.

DESCRIPTION OF THE INVENTION

The invention encompasses compounds of Formula I, their salts and solvates, compositions, and methods of using these compounds.

One aspect of the invention are compounds of Formula I

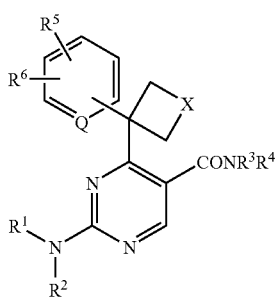

wherein:
Q is CH or N;
X is a bond, methylene, ethylene, or propylene;

$R^1$ is hydrogen, $C_{1-6}$alkyl, $C_{3-7}$cycloalkyl, $CH_2Ar^1$, $CH_2CH_2Ar^1$, $CH(CH_3)Ar^1$, $CH_2CH(CH_3)Ar^1$, $CH(CH_2OH)CH_2Ar^1$, $CH_2CH_2CH_2Ar^1$, $CH_2CH_2OAr^1$, $CH_2CH_2SAr^1$, $CH_2CH_2N(R^7)Ar^1$, $CH_2CH_2CH_2CH_2Ar^1$, $CH_2CH_2CH_2CH_2CH_2Ar^1$, or $CH_2CH_2CH_2CH_2CH_2CH_2Ar^1$ wherein the $C_{1-6}$alkyl group is unsubstituted or substituted with 1–2 moieties selected from the group consisting of $OR^7$, $CO_2R^7$, $N(R^7)(R^7)$, $CON(R^7)(R^7)$, $N(R^7)COR^7$, and $R^8$;
$R^2$ is hydrogen or $C_{1-6}$alkyl;
or $NR^1R^2$ taken together are

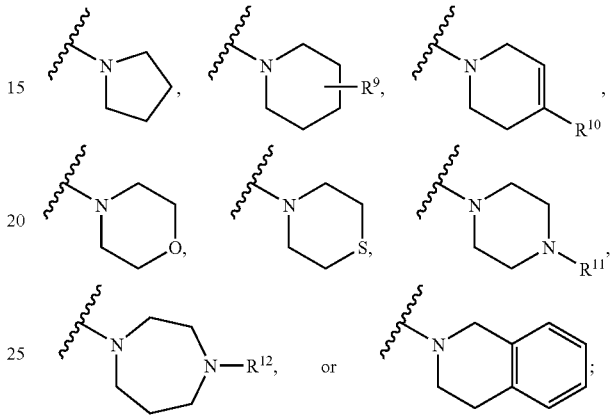

$R^3$ is hydrogen, $C_{1-6}$alkyl, $C_{3-7}$cycloalkyl, $CH_2Ar^1$, $CH_2CH_2Ar^1$, $CH(CH_3)Ar^1$, $CH_2CH(CH_3)Ar^1$, $CH(CH_2OH)CH_2Ar^1$, $CH_2CH_2CH_2Ar^1$, $CH_2CH_2OAr^1$, $CH_2CH_2SAr^1$, $CH_2CH_2N(R^7)Ar^1$, $CH_2CH_2CH_2CH_2Ar^1$, $CH_2CH_2CH_2CH_2Ar^1$, $CH_2CH_2CH_2CH_2CH_2Ar^1$, $Ar^2$, $CH_2Ar^2$, $CH_2CH_2Ar^2$, or $CH(CH_3)Ar^2$, wherein the $C_{1-6}$alkyl group is unsubstituted or substituted with 1–2 moieties selected from the group consisting of $OR^7$, $CO_2R^7$, $N(R^7)(R^7)$, $CON(R^7)(R^7)$, $N(R^7)COR^7$, and $R^8$;
$R^4$ is hydrogen or $C_{1-6}$alkyl;
or $N(R^3)(R^4)$ taken together are

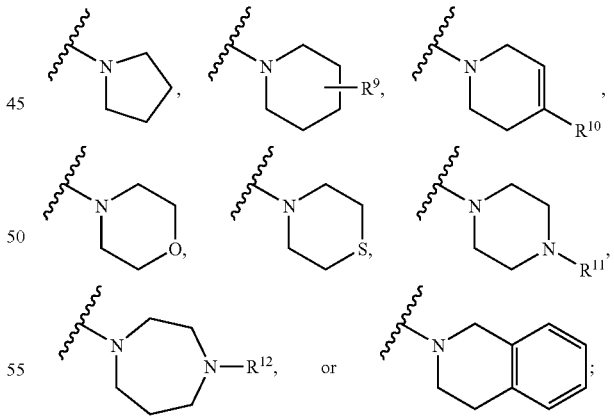

$R^5$ and $R^6$ are independently hydrogen, halo, $C_{1-6}$alkyl, trifluoromethyl, cyano, $OR^7$, or $N(R^7)(R^7)$;
$R^7$ is independently hydrogen or $C_{1-6}$alkyl;
$R^8$ is a heterocycle selected from the group consisting of tetrahydrofuranyl, pyrrolidinyl, piperidinyl, and benzopyrrolidinyl and is unsubstituted or substituted with 1 substituent selected from the group consisting of oxo, $C_{1-6}$alkyl, hydroxymethyl, benzyl, and $CO_2R^7$;
$R^9$ is hydrogen, $C_{1-6}$alkyl, $CO_2R^7$, or $CON(R^7)(R^7)$;

$R^{10}$ is hydrogen or phenyl;
$R^{11}$ is hydrogen, $C_{1-6}$alkyl, or $C_{1-6}$hydroxyalkyl;
$R^{12}$ is hydrogen, $C_{1-6}$alkyl, or $COR^7$;
$Ar^1$ is phenyl, naphthyl, pyridinyl or benzodioxolanyl and is unsubstituted or substituted with 1–2 moieties selected from the group consisting of halo, $C_{1-6}$alkyl, trifluoromethyl, cyano, pyridinyloxy, $OR^7$, $N(R^1)(R^2)$, or $Ar^2$; and
$Ar^2$ is pyridinyl, pyrimidinyl, pyridizinyl, or triazinyl;

or a pharmaceutically acceptable salt or solvate thereof.

Another aspect of the invention are compounds of Formula I where X is a bond.

Another aspect of the invention are compounds of Formula I where X is methylene.

Another aspect of the invention are compounds of Formula I where X is ethylene.

Another aspect of the invention are compounds of Formula I where X is propylene.

Some compounds of the invention are listed in the specific embodiments section.

"Alkyl" and other substituents with an alkyl moiety include both straight and branched chain configurations. Aryl includes both carbocyclic and heterocyclic aromatic moieties. "Benzopyrrolidinyl" means a pyrrolidine ring fused with a benzene ring in either a 1,2 sense or a 2,3 sense.

"Benzodioxolanyl" means

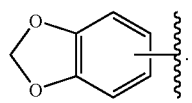

"Pyridinyloxy" means

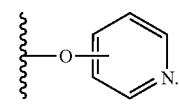

The invention includes all pharmaceutically acceptable salt forms of the instant compounds. Pharmaceutically acceptable salts are those in which the counter ions do not contribute significantly to the physiological activity or toxicity of the compounds and as such function as pharmacological equivalents. In many instances, salts have physical properties that make them desirable for formulation, such as solubility or crystallinity. The salts can be made according to common organic techniques employing commercially available reagents. Suitable anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Suitable cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the instant compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate. Some hydrated forms include monohydrate, hemihydrate, and dihydrate.

Synthetic Methods

The compounds of this invention can be made by the methods illustrated in Schemes A–E. All reagents are commercially available or made by methods known in the art. Additional compounds can be made using these methods.

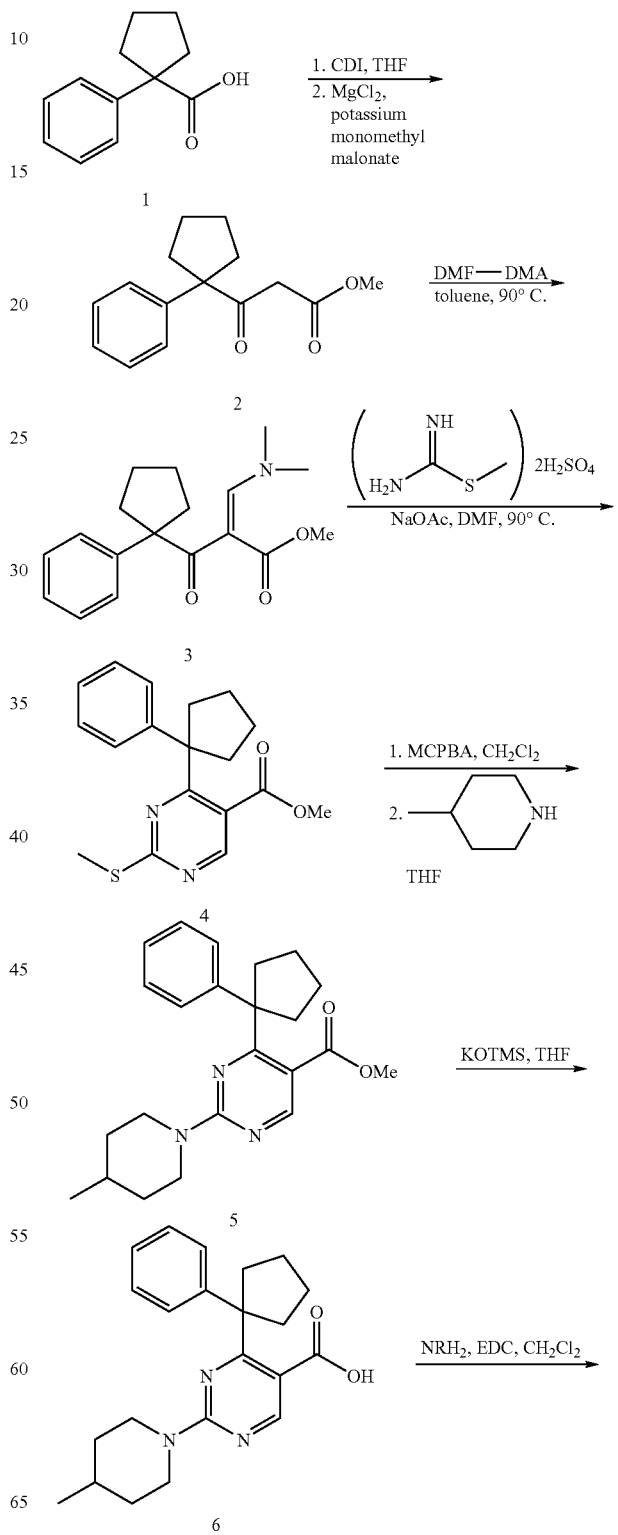

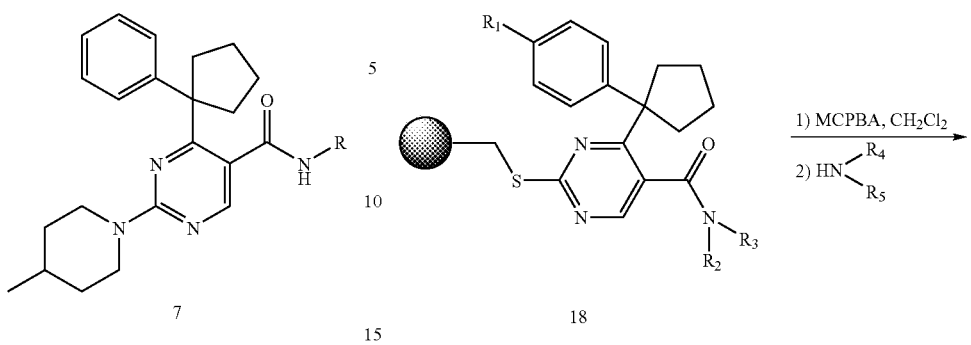
7
Scheme B.
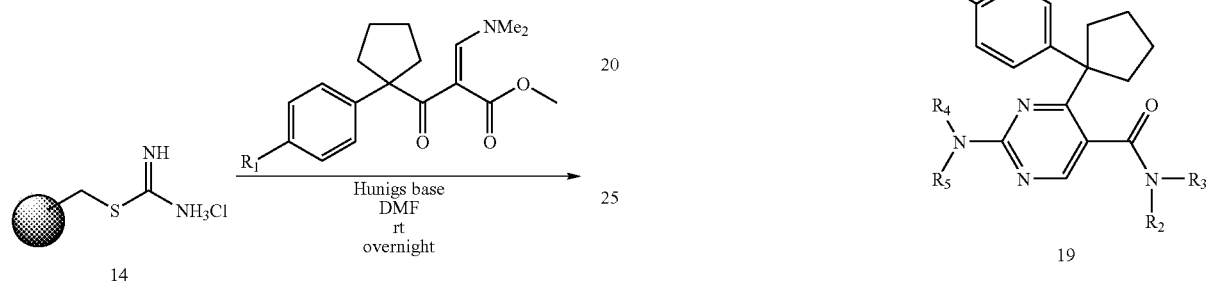
14
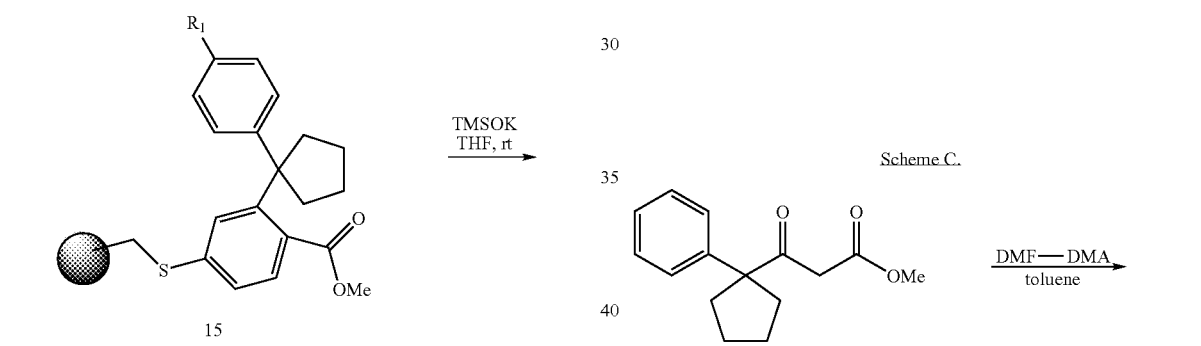
15
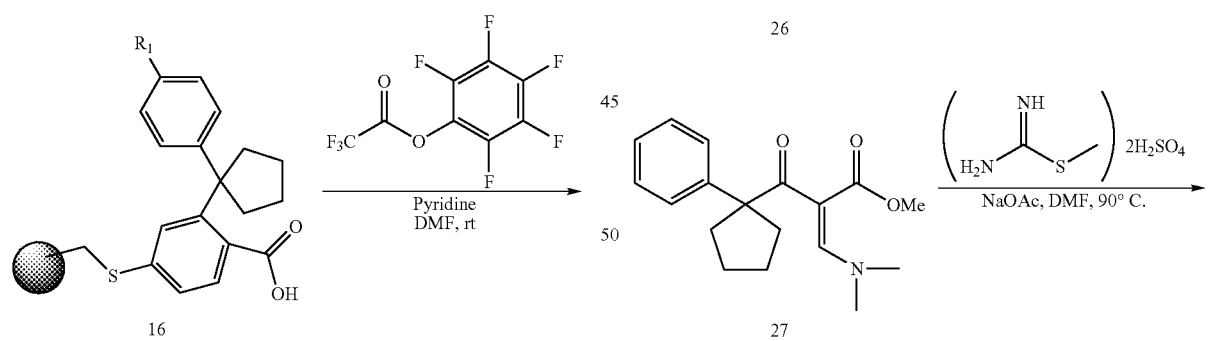
16
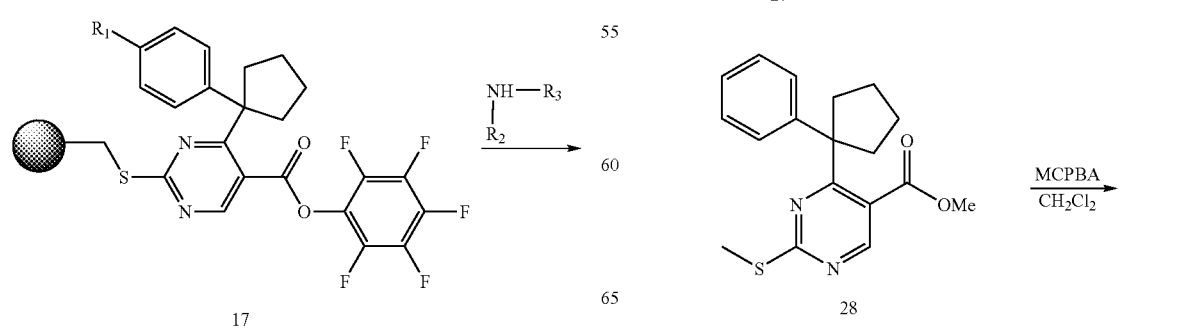
17
18
19
Scheme C.
26
27
28

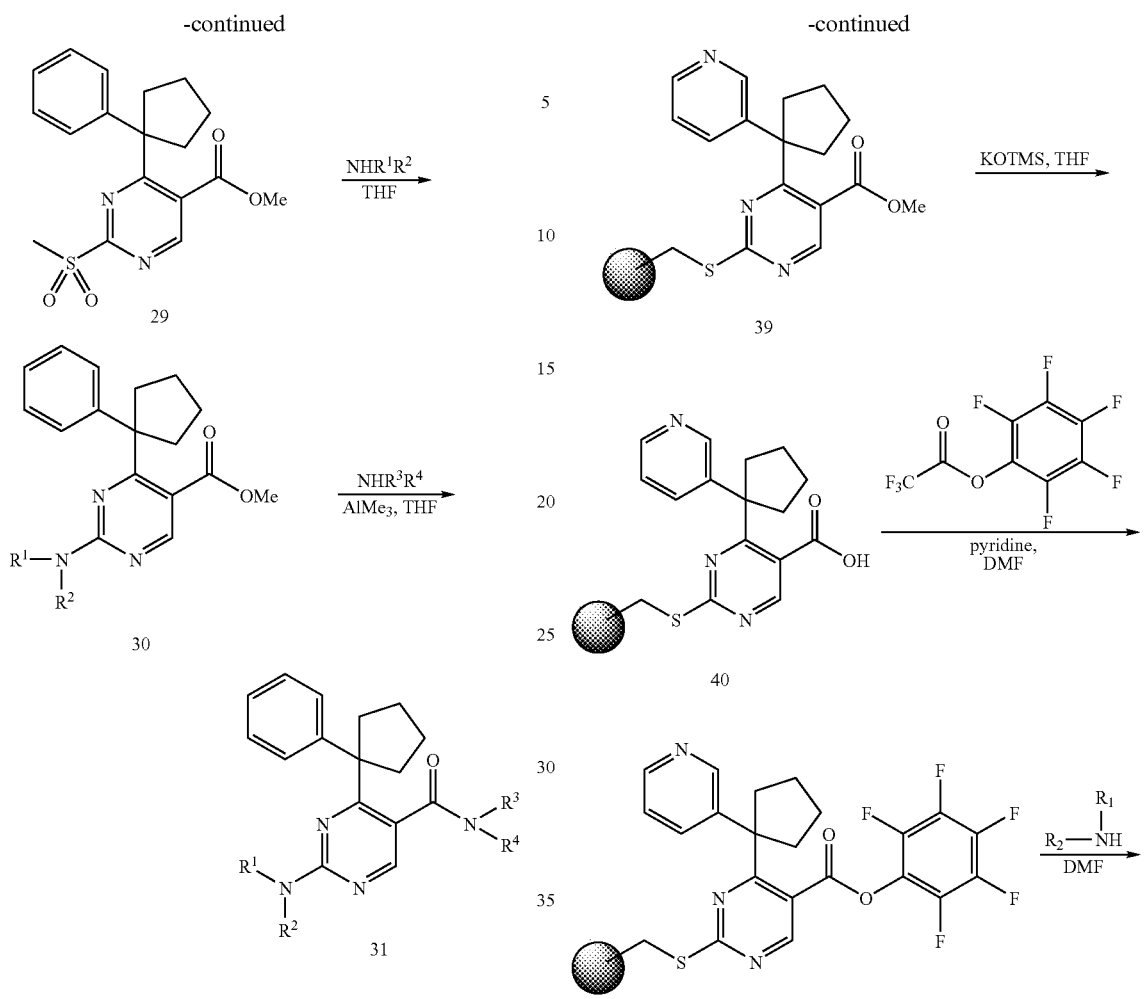

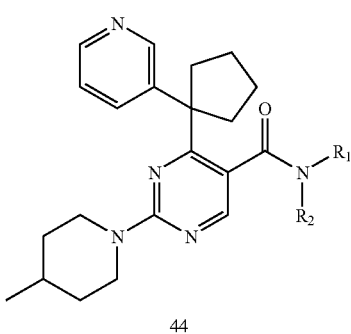

44

Scheme E.

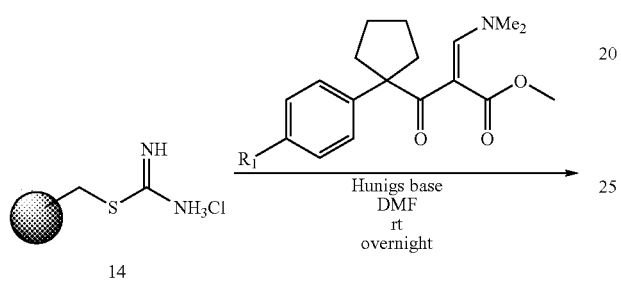

14

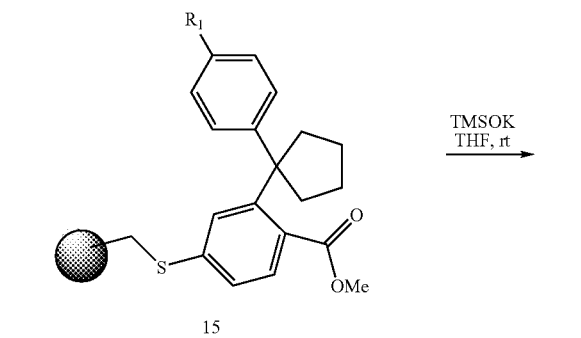

15

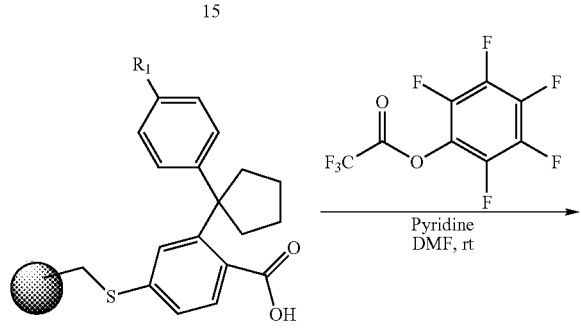

16

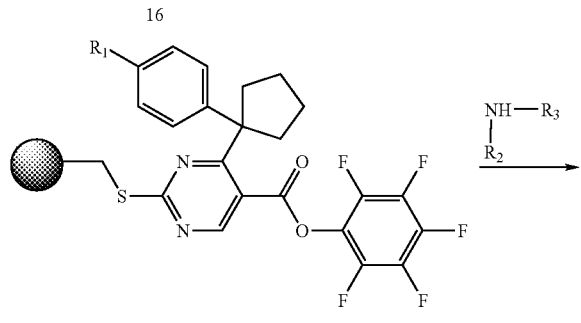

17

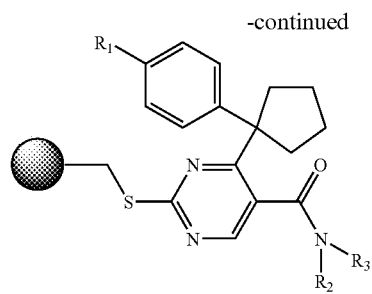

18

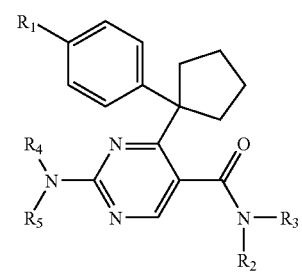

48

Biological Methods

The compounds of this invention were evaluated for blocking KCNQ channels using an assay. Representative compounds were confirmed to be KCNQ blockers in a functional assay measuring current through KCNQ channels transfected into oocytes.

Thallium Flux Assay for KCNQ channel blockers. Approximately 20,000 cells/well of an HEK-293 cell line stably transfected with one of the members of the KCNQ family were plated into clear-bottom, black-walled, poly-D-lysine coated, 384 well assay plates in 20 μl/well of low chloride plating medium. Low chloride plating medium was composed of the following: sodium gluconate, 109 mM; potassium gluconate, 5.4 mM; hemi-calcium gluconate, 3.6 mM; magnesium sulfate, 0.8 mM; sodium bicarbonate, 26.2 mM; sodium phosphate monobasic, 1.2 mM; glutamine, 2 mM; glucose, 5 mM; HEPES (pH 7.3) 10 mM, 10× concentration of vitamins (Gibco/LifeTechnologies catalog #11120-052) and 1× concentration of amino acids (Gibco/LifeTechnologies catalog #11130-051).

Following overnight incubation in a 5% $CO_2$ incubator at 37° C., the cells in the plates were loaded with 20 μl/well of a dye loading solution containing the acetomethoxy ester of the thallium-sensitive fluorescent dye BTC, BTC-AM (2 μM) and pluronic acid (0.02% w/v) in chloride free assay buffer. Chloride free assay buffer was composed of the following: sodium gluconate, 140 mM; potassium gluconate, 2.5 mM; hemi-calcium gluconate, 6 mM; hemi-magnesium gluconate, 2 mM; glucose, 5 mM; HEPES (pH 7.3), 10 mM.

Following incubation in the dye loading solution for from 45–90 min at room temperature, the dye loading solution was removed by aspiration and replaced with 40 μl/well of chloride free assay buffer.

Prior to addition to cell plates, test compound and standard compounds were dissolved in DMSO to 3 mM concentration. Compounds were then diluted from the 3 mM stock to 100-fold over the final assay concentration in DMSO. Finally, compounds in DMSO were diluted from 100-fold over the final assay concentration to 5-fold over the final assay concentration in chloride free assay buffer.

Ten µl/well of compounds at 5-fold over the final assay concentration were then added to the cell plates. This represents a 1:5 dilution, yielding the final test concentration. The wells used for test compounds were A1–P20. Wells A21–P22 contained a standard 'blocker' and a fully efficacious concentration (positive control). Wells A23–P24 contained chloride free assay buffer containing 1% DMSO (negative control).

Following addition of test compounds, the plates were loaded onto the Molecular Devices FLIPR. The 488 nm line of the argon laser was used to excite the BTC and the emission filter was a 540(+/−30) nm. Images were collected at 1 Hz. Ten seconds of baseline were collected and then the FLIPR was used to add 13 µl/well of a stimulus buffer composed of $Tl_2SO_4$, 25 mM; sodium gluconate, 30 mM; potassium sulfate, 50 mM; hemi-calcium gluconate, 6 mM; hemi-magnesium gluconate, 2 mM; glucose, 5 mM; HEPES (pH 7.3), 10 mM in chloride free assay buffer. Images were collected for an additional 60 seconds.

For data analysis, the amplitude of the average of the negative controls was subtracted from all wells. The amplitudes of the test compounds were then compared to the value of four standard deviations of the negative control wells. The lowest concentration of a test compound sufficient to generate a signal amplitude greater than or equal to four standard deviations from the amplitude of the negative controls was defined as the minimal active concentration.

For generating $IC_{50}$ values, compounds were serially diluted in 1:3 volume increments to produce a 10 point concentration series. $IC_{50}$ values were calculated by fitting the resulting amplitudes to a single-site logistic equation. $IC_{50}$ was defined as the concentration of test compound required to yield 50% of the response of the positive control.

The biological activity of several Formula I compounds are listed in Tables 1–3.

KCNQ Patch-clamp. Frog oocytes were surgically harvested from mature *Xenopus laevis* that had been anesthetized with 0.15% 3-aminobenzoic acid ethyl ester (tricaine). Only late stage V and VI oocytes were selected for cRNA injection, and the overlying follicle cell layers were enzymatically removed. Each oocyte was injected with approximately 60 ng of the mKCNQ2 cRNA. Following injection, oocytes were maintained at 17° C. in ND96 medium consisting of (in mM): NaCl, 90; KCl, 1.0; $CaCl_2$, 1.0; $MgCl_2$, 1.0; HEPES, 5.0; (pH 7.5) and supplemented with heat-inactivated horse serum (5%) and penicillin/streptomycin (5%).

Two-electrode voltage clamp techniques were used to record membrane currents; recording commenced 3–7 days following cRNA injection (Gribkoff, V. K., et al., *Mol. Pharmacol.* 1996, 50(1), 206–217). For recording and compound application, oocytes were placed in a recording chamber and incubated in Modified Barth's Solution (MBS) consisting of (in mM): NaCl, 88; $NaHCO_3$, 2.4; KCl, 1.0; HEPES, 10; $MgSO_4$, 0.82; $Ca(NO_3)_2$, 0.33; $CaCl_2$, 0.41; (pH 7.5). Voltage-clamp protocols consisted of a series of 4 second duration depolarizing voltage steps from a holding potential of −90 mV to a maximal potential of +40 mV in 10 mV intervals. A family of outward currents was generated under control conditions for comparison with currents elicited in the presence of an experimental compound. Control or drug solutions were continually introduced into the recording chamber using a gravity-flow system with an in-line electronic valve array. A minimum of 5 oocytes was used for each drug concentration; drug concentrations ranged from 0.001 µM to 10 µM. During a single experiment, an oocyte was exposed to as many as three drug concentrations sequentially administered for 5 minutes each. All experiments ended with a 5 minute application of TEA (5 mM), a non-selective, but effective blocker of KCNQ channels. Typically, 5 mM TEA produced a maximal blockade of outward current when measured at the −40 mV membrane voltage (94.6+/−0.5% inhibition, n=112). In this manner, all drug effects could be presented as a percentage of TEA blockade, controlling for the variable levels of channel expression from oocyte to oocyte. Table 1 discloses data for representative examples. Data are expressed as percent inhibition relative to TEA blockade at a membrane voltage of −40 mV: A>50% TEA blockage at 100 nM, B>50% TEA blockage at 1 µM, C<50% TEA blockage at 1.0 µM.

TABLE 1

| Example | Percent TEA blockage |
|---------|----------------------|
| 16 | A |
| 138 | B |
| 181 | A |
| 263 | A |
| 299 | B |

A > 50% TEA blockage at 100 nM,
B > 50% TEA blockage at 1 µM,
C < 50% TEA blockage at 1.0 µM.

Pharmaceutical Composition and Methods of Use

The compounds of this invention block KCNQ channels. Compounds that block KCNQ channels and thus modulate M current, including linopirdine and XE-991, demonstrate cognition enhancing effects. The compounds act by increasing the stimulus-evoked release of a number of neurotransmitters in the central nervous system. See Wang et al. *Science* 1998, 282, 1890; Lamas *Eur. J. Neurosci.* 1997, 9, 607; Schnee and Brown *J. Pharmacol. Exp. Ther.* 1998, 286, 709; Zaczek et al. *J. Pharmacol Exp. Ther.* 1998, 285, 724 and references cited by these papers.

Accordingly, another aspect of the invention is a method of blocking KCNQ channels comprising administering an effective amount of a compound of Formula I to a patient in need of such treatment.

Another aspect of the invention is a method of modulating M-current comprising administering an effective amount of a compound of claim 1 and a pharmaceutically acceptable carrier to a patient characterized with aberrant M-current.

Another aspect of the invention is a method of enhancing cognition comprising administering a therapeutically effective amount of a compound of claim 1 and a pharmaceutically acceptable carrier to a patient.

Another aspect of the invention is a composition comprising a therapeutically effective amount of a compound of claim 1 and a pharmaceutically acceptable carrier.

"Therapeutically effective" means the amount of agent required to provide a meaningful patient benefit as understood by practitioners in the field. "Cognition" and terms related to cognition and enhancing cognition are as understood by practitioners in the field.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10, mg, 100, mg, 250 mg, 500 mg, and 1000 mg.

Liquid compositions are usually in dosage unit ranges. Generally, the liquid composition will be in a unit dosage range of 1–100 mg/mL. Some examples of dosages are 1 mg/mL, 10 mg/mL, 25, mg/mL, 50 mg/mL, and 100 mg/mL.

The invention encompasses all conventional modes of administration; oral and parenteral methods are preferred. Typically, the daily dose will be 1–100 mg/kg body weight daily. Generally, more compound is required orally and less parenterally. The specific dosing regime, however, will be determined by a physician using sound medical judgement.

DESCRIPTION OF SPECIFIC EMBODIMENTS

General Procedure A

To a 500 mL round bottom flask containing phenylcyclopentane carboxylic acid 1 (14 g, 73 mmol) was added anhydrous THF (200 mL). Carbonyldiimidazole (12.5 g, 77 mmol) was added to the reaction mixture, which was then allowed to stir for 2 hr. at room temperature. A mixture of magnesium chloride (7.7 g, 81 mmol) and potassium monomethylmalonate (12.6 g, 81 mmol) was added, and the solution was heated to 50° C. and stirred overnight. The solid was filtered off and washed with THF. The filtrate was evaporated then dissolved in ethyl acetate. The mixture was washed with 1N HCl (1×) and 5% aqueous sodium bicarbonate (2×). The combined organic layers were then dried over anhydrous magnesium sulfate, filtered, and concentrated to give a waxy pale yellow solid (11.7 g, 65% yield) which was used without further purification. $^1$H NMR (CDCl$_3$, 400 MHz): δ=7.34 (m, 2H), 7.27 (m, 3H), 3.63 (s, 3H), 3.28 (s, 2H), 2.53–2.47 (m, 2H), 1.98–1.90 (m, 2H), 1.72 (m, 4H).

To a 500 mL round bottom flask was added 3-oxo-3-(1-phenyl-cyclopentyl)-propionic acid methyl ester, 2, (10.8 g, 44 mmol), dimethylformamide-dimethylacetal (7 mL), and anhydrous toluene (113 mL). The reaction mixture was heated to 85° C. and allowed to stir overnight. The reaction was monitored by NMR and allowed to stir until the methylene singlet at 3.28 ppm disappeared. The reaction mixture was then concentrated to provide a brown oil (12.83 g, 96% yield) which was carried onto the next step without purification. To a 100 mL round bottom flask was added 3-dimethylamino-2-(1-phenyl-cyclopentane carbonyl)-acrylic acid methyl ester 3 (4.42 g, 13.6 mmol), sodium acetate (1.36 g, 16.5 mmol), s-methylthiopseudourea sulfate (2.1 g, 7.5 mmol), and anhydrous DMF (27 mL). The solution was heated to 90° C. and allowed to stir overnight. The reaction was allowed to cool and was then diluted with ether. The solution was extracted with 1N HCl (2×), 5% aqueous sodium bicarbonate (2×), H$_2$O (2×), and saturated aqueous sodium chloride (1×). The organic layers were combined, dried over anhydrous magnesium sulfate, filtered and concentrated to yield a light yellow solid. Purification via column chromatography (silica gel, 20% ethyl acetate in hexanes) provided the desired thiopyrimidine 4 as a pale yellow oil (3.68 g, 68% yield). $^1$H NMR (CDCl$_3$, 400 MHz): δ 8.50 (s, 1H), 7.24 (m, 2H), 7.16 (tt, 1H, J=7.3, 1.2 Hz), 7.10 (m, 2H), 3.37 (s, 3H), 2.66 (s, 3H), 2.63–2.56 (m, 2H), 2.32–2.25 (M, 2H), 1.80–1.74 (m, 4H).

To a 50 mL round bottom flask was added 2-methylsulfanyl-4-(1-phenyl-cylcopentyl)-pyrimidine-5-carboxylic acid methyl ester 4 (0.50 g, 1.4 mmol), 57–86% MCPBA (0.87 g, 2.9 mmol), and anhydrous dichloromethane (5 mL). The reaction was allowed to stir at room temperature for 2 h. The reaction mixture was then concentrated and purified via column chromatography (silica gel, 30% ethyl acetate in hexanes) to produce the desired intermediate sulfone as a white solid (0.47 g, 86% yield).

To a 50 mL round bottom flask containing sulfone (0.47 mg, 1.2 mmol) was added 4-methylpiperidine (0.36 mg, 3.7 mmol) and anhydrous THF (2 mL). The reaction mixture was allowed to stir at room temperature overnight. The solvent was then removed. Purification was accomplished via column chromatography (silica gel, 30% ethyl acetate in hexanes), and provided the desired aminopyrimidine 5 as a clear and colorless oil (0.37 mg, 75% yield).

To a 100 mL round bottom flask was added 2-(4-methyl-piperidin-1-yl)-4-(1-phenyl-cyclopentyl)-pyrimidine-5-carboxylic acid methyl ester 5 (0.7 g, 1.84 mmol) and anhydrous THF (15 mL). The solution was stirred until homogenous. Potassium trimethylsilanoate (0.26 g. 2.03 mmol) was then added, and the reaction mixture was allowed to stir at reflux for 6 h. Once complete, the reaction mixture was concentrated in vacuo, then diluted with dichloromethane. The organic layer was washed with saturated NH$_4$Cl, dried over anhydrous magnesium sulfate, filtered and concentrated to give a foam. The crude product was purified via column chromatography (silica gel, 4:1 hexanes:ethyl acetate) to provide the desired acid 6 as a white foam (0.543 g, 81% yield).

To a reaction vial containing amine (0.025 mmol) was added 2-(4-methyl-piperidin-1-yl)-4-(1-phenyl-cyclopentyl)-pyrimidine-5-carboxylic acid 6 (0.018 g, 0.05 mmol), EDC (0.009 g, 0.05 mmol) and anhydrous dichloromethane (1 mL). The reaction was allowed to stir at room temperature overnight. The reaction mixture was then concentrated and purified by flash chromatography (25% acetone in hexanes) to provide the final product.

General Procedure B

To 500 mL 3-neck flask was added Merrifield resin 70–90 mesh (29.6 g, 0.0367 mol) and thiourea (4.54 g, 0.0597 mol) in 200 mL dry DMF. The reaction was mechanically stirred and heated to 75° C. for 24 hr. The reaction was cooled to room temperature, then filtered through a scintered glass funnel. The filter cake was washed with DMF (3×100 mL), dichloromethane (3×250 mL) and of THF (2×200 mL). The desired thiourea resin was dried in vacuo and used as is in subsequent reactions. IR (neat): 1657 cm$^{-1}$.

To a 125 mL peptide vessel with a scintered glass bottom was added thiourea resin 14 (0.0126 mol) in anhydrous DMF (50 mL). Excess 3-dimethylamino-2-(1-phenyl-cyclopentanecarbonyl)-acrylic acid methyl ester (0.0378 mmol) was added followed by Hunigs base (4.87 g, 0.0378 mol), and the vessel was sealed and shaken at room temperature for 24 hrs. The reaction solution was filtered through the scintered glass bottom of the peptide vessel. The filter cake was washed with DMF (3×50 mL), THF (3×250 mL) and dichloromethane (2×200 mL). The desired thiopyrimidine resin was dried in vacuo and used as is in subsequent reactions. IR (neat): 1736 cm$^{-1}$.

To a 125 mL peptide vessel with a scintered glass bottom was added thiopyrimidine resin 15 (0.0126 mol) in anhydrous THF (50 mL). Potassium trimethylsilanolate (8.08 g, 0.063 mol) was added, and the vessel was sealed and shaken at room temperature for 24 hrs. The reaction solution was filtered through the scintered glass bottom of the peptide vessel. The filter cake was washed with THF (2×100 mL), 5% HOAc solution in DMF (3×100 mL), and dichloromethane (3×100 mL). The desired thiopyrimidinecarboxylic acid resin was dried in vacuo and used as is in subsequent reactions. IR (neat): 1697 cm$^{-1}$.

To a 125 mL peptide vessel with a scintered glass bottom was added thiopyrimidinecarboxylic acid resin 16 (0.0126 mol) in anhydrous DMF (50 mL). pentafluorophenyl trifluoroacetate (17.6 g, 0.063 mol) and pyridine (4.97 g, 0.063 mol) were added, and the vessel was sealed and shaken at room temperature for 24 h. The reaction solution was filtered through the scintered glass bottom of the peptide vessel. The filter cake was washed with DMF (2×100 mL), dichloromethane (3×100 mL), and of anhydrous Et$_2$O (3×100 mL). The desired thiopyrimidinepentafluorophenylester resin was dried in vacuo and used as is in subsequent reactions. IR (neat): 1776 cm$^{-1}$.

To a 4 mL vial was added thiopyrimidinepentafluorophenylester resin 17 (0.050 mmol) in 1 mL anhydrous DMF. The resin was shaken for 1 min and amine (0.50 mmol) was added. The resin was then shaken overnight at room temperature. The resin was filtered away from the reaction solution, and washed with dichloromethane (4×5 mL) and Et$_2$O (2×5 mL). The desired thiopyrimidinecarboxamide resin was carried onto the next step as is.

To a 4 mL vial was added thiopyrimidinecarboxamide resin (0.050 mmol) in anhydrous dichloromethane (1 mL). The resin was shaken for 1 min after which time 3-chloroperoxybenzoic acid (57–86%) (0.30 mmol) was added. The resin was shaken overnight at room temperature. The resin was then filtered away from the reaction solution and washed with dichloromethane (3×5 mL), DMF (3×5 mL), and again with dichloromethane (3×5 mL). The desired sulfone resin 18 was carried onto the next step as is.

To a 4 mL vial was added sulfone resin (0.050 mmol) in anhydrous THF (1 mL). The resin was shaken for 1 min. after which time amine (0.50 mmol) was added. The resin was shaken overnight at room temperature. The resin was then filtered away from the reaction solution and washed with THF (1 mL). The filtrate was evaporated in vacuo to provide the desired product 19.

General Procedure C

To a 100 mL round bottom flask was added 2-methanesulfonyl-4-(1-phenyl-cyclopentyl)-pyrimidine-5-carboxylic acid methyl ester 29 (2.0 mmol), amine (6.1 mmol), and anhydrous THF (20 mL). The solution was allowed to stir at room temperature overnight. Upon completion of the reaction, the solvent was removed. Purification via flash chromatography provided pure product.

To a 100 mL round bottom flask was added amine (1.3 mmol), trimethylaluminum (2.2 mmol), and anhydrous THF (4.6 mL). The solution was allowed to stir at room temperature for 10 min, after which the methyl ester 30 (0.65 mmol) was added. The reaction mixture was then heated to reflux and allowed to stir for 48 h. Reaction was then quenched with saturated NH$_4$Cl, and the aqueous layer was extracted with EtOAc (3×). The organic layer was dried over anhydrous sodium sulfate, filtered and concentrated. Purification via column chromatography provided the desired final product 31.

General Procedure D

To a suspension of activated zinc dust (1.62 g, 25 mmol) in refluxing anhydrous THF was added methylbromoacetate (4 drops). After the appearance of a green color 1-pyridin-3-yl-cyclopentanecarbonitrile 36 (0.879 g, 5.1 mmol) was added. Methylbromoacetate (1.93 mL, 20.4 mmol) was then added over 45 min. The reaction became dark orange and was allowed to reflux for 3.5 hr. The reaction mixture was then diluted with THF (46 mL), and 50% aqueous potassium carbonate (6.5 mL) was added. The reaction mixture was allowed to stir at room temperature for 15 min. after which two distinct layers could be observed. The layers were separated and the organic layer was subsequently filtered through celite. The organic layer was then dried over anhydrous magnesium sulfate, filtered and concentrated to give a dark brown oil. The resulting oil was redissolved in THF and 10% aqueous HCl (33 mL) was added. The reaction mixture was allowed to stir overnight after which time the solvent was removed. The resulting residue was dissolved in dichloromethane, and the mixture was then washed with saturated sodium bicarbonate. The organic layer was dried over anhydrous magnesium sulfate, filtered and concentrated to provide product as a brown oil which was used without further purification (4.69 g, 72% yield). $^1$H NMR (CDCl$_3$, 400 MHz): δ 8.58 (d, 1H, J=1.8 Hz), 8.52 (dd, 1H, J=3.2, 1.5 Hz), 7.58 (m, 1H), 7.29 (m, 1H), 3.60, (s, 3H), 3.30 (s, 2H), 2.57–2.50 (m, 2H), 1.97–1.90 (m, 2H), 1.75–1.71 (m, 4H); LCMS: 248.2 [M+H]$^+$; Retention time: 0.46 min.

To a round bottom flask containing 3-oxo-3-(1-pyridin-3-yl-cyclopentyl)-proprionic acid methyl ester 37 (0.954 g, 3.8 mmol) was added anhydrous toluene (9.7 mL). Dimethylformamide-dimethylacetal (0.613 mL, 4.6 mmol) was then added and the reaction was allowed to stir at 90° C. for 24 h. The reaction was then concentrated and dried in vacuo. The product was isolated as a brown oil (1.12 g, 97% yield) and used without further purification. $^1$H NMR (CDCl$_3$, 400 MHz): δ 8.53 (d, 1H, J=1.8 Hz), 8.41 (dd, 1H, J=4.9, 1.6 Hz), 7.59 (m, 1H), 7.48 (s, 1H), 7.19 (m, 1H), 3.29 (s, 3H), 2.36 (s, 6H), 2.47–2.40 (m, 2H), 2.12–2.06 (m, 2H), 1.79–1.72 (m, 2H), 1.64–1.60 (m, 2H); LCMS: 300.3 [M+H]$^+$; Retention time: 1.07 min.

To a vial containing thiourea resin (1.15 g, 1.49 mmol) was added 3-dimethylamino-2-(1-pyridin-3-yl-cyclopentanecarbonyl)-acrylic acid methyl ester 38 (1.29 g, 4.3 mmol), diisopropylethylamine (0.65 mL, 4.3 mmol), and DMF (7 mL). The suspension was allowed to shake overnight at room temperature. The resin was then washed with DMF (3×), THF (3×), and dichloromethane (3×). The desired thiopyrimidine resin was dried in vacuo and used as is in subsequent reactions. IR (neat): 1726 cm$^{-1}$.

To a vial containing thiopyrimidine resin 39 (0.15 mol) was added THF (1 mL) and potassium trimethylsilanolate (0.098 g, 0.768 mmol). The vial was sealed and shaken at room temperature for 24 h. The reaction solution was filtered, and the filter cake was washed with THF (2×100 mL), 5% HOAc solution in DMF (3×100 mL), and dichloromethane (3×100 mL). The desired thiopyrimidinecarboxylic acid resin was dried in vacuo and used as is in subsequent reactions.

To a vial containing thiopyrimidinecarboxylic acid resin 40 (0.10 g, 0.134 mmol) was added DMF (1 mL), pentafluorophenyl trifluoroacetate (0.114 mL, 0.668 mmol) and pyridine (0.054 mL, 0.668 mmol), and the vessel was sealed and shaken at room temperature for 24 hr. The reaction solution was filtered, and the filter cake was washed with DMF (2×100 mL), dichloromethane (3×100 mL), and anhydrous Et$_2$O (3×100 mL). The desired thiopyrimidinepentafluorophenylester resin was dried in vacuo and used as is in subsequent reactions.

To a 4 mL vial was added thiopyrimidinepentafluorophenylester resin 41 (0.134 mmol) in DMF (1 mL). The resin was shaken for 1 min and amine (0.402 mmol) was added. The resin was then shaken overnight at room temperature. The resin was filtered away from the reaction solution and washed with dichloromethane (4×5 mL) and Et$_2$O (2×5 mL). The desired thiopyrimidinecarboxamide resin was carried onto the next step as is.

To a 4 mL vial containing resin 42 (0.13 mmol) was added Davis reagent (0.65 mmol) and dichloromethane (1 mL). The reaction mixture was allowed to shake at room temperature overnight. The resin was then washed with dichloromethane (3×), DMF (3×) and ether (3×), and dried in vacuo. The desired resin was carried onto the next step as is.

To a 4 mL vial containing resin 43 (0.242 g, 0.306 mmol) was added 4-methylpiperidine (0.091 g, 0.918 mmol) and THF (2 mL). The reaction mixture was shaken overnight at room temperature. The resin was then washed with dichloromethane (3×), DMF (3×), and ether (3×), and the filtrate was collected and concentrated. Purification via column chromatography (silica gel) provided the desired products 44.

General Procedure E

To 500 mL 3-neck flask was added Merrifield resin 70–90 mesh (29.6 g, 0.0367 mol) and thiourea (4.54 g, 0.0597 mol) in 200 mL dry DMF. The reaction was mechanically stirred and heated to 75° C. for 24 hr. The reaction was cooled to room temperature, then filtered through a scintered glass funnel. The filter cake was washed with DMF (3×100 mL), dichloromethane (3×250 mL) and of THF (2×200 mL). The desired thiourea resin was dried in vacuo and used as is in subsequent reactions. IR (neat): 1657 cm$^{-1}$.

To a 125 mL peptide vessel with a scintered glass bottom was added thiourea resin 14 (0.0126 mol) in anhydrous DMF (50 mL). Excess 3-dimethylamino-2-(1-phenyl-cyclopentanecarbonyl)-acrylic acid methyl ester (0.0378 mmol) was added followed by Hunigs base (4.87 g, 0.0378 mol), and the vessel was sealed and shaken at room temperature for 24 hrs. The reaction solution was filtered through the scintered glass bottom of the peptide vessel. The filter cake was washed with DMF (3×50 mL), THF (3×250 mL) and dichloromethane (2×200 mL). The desired thiopyrimidine resin was dried in vacuo and used as is in subsequent reactions. IR (neat): 1736 cm$^{-1}$.

To a 125 mL peptide vessel with a scintered glass bottom was added thiopyrimidine resin 15 (0.0126 mol) in anhydrous THF (50 mL). Potassium trimethylsilanolate (8.08 g, 0.063 mol) was added, and the vessel was sealed and shaken at room temperature for 24 hrs. The reaction solution was filtered through the scintered glass bottom of the peptide vessel. The filter cake was washed with THF (2×100 mL), 5% HOAc solution in DMF (3×100 mL), and dichloromethane (3×100 mL). The desired thiopyrimidinecarboxylic acid resin was dried in vacuo and used as is in subsequent reactions. IR (neat): 1697 cm$^{-1}$.

To a 125 mL peptide vessel with a scintered glass bottom was added thiopyrimidinecarboxylic acid resin 16 (0.0126 mol) in anhydrous DMF (50 mL). Pentafluorophenyl trifluoroacetate (17.6 g, 0.063 mol) and pyridine (4.97 g, 0.063 mol) were added, and the vessel was sealed and shaken at room temperature for 24 hr. The reaction solution was filtered through the scintered glass bottom of the peptide vessel. The filter cake was washed with DMF (2×100 mL), dichloromethane (3×100 mL), and of anhydrous Et$_2$O (3×100 mL). The desired thiopyrimidinepentafluorophenylester resin was dried in vacuo and used as is in subsequent reactions. IR (neat): 1776 cm$^{-1}$.

To a 4 mL vial was added thiopyrimidinepentafluorophenylester resin 17 (0.050 mmol) in 1 mL anhydrous DMF. The resin was shaken for 1 min and amine (0.50 mmol) was added. The resin was then shaken overnight at room temperature. The resin was filtered away from the reaction solution, and washed with dichloromethane (4×5 mL) and Et$_2$O (2×5 mL). The desired thiopyrimidinecarboxamide resin 18 was carried onto the next step as is.

To a 4 mL vial was added thiopyrimidinecarboxamide resin 18 (0.050 mmol) in anhydrous dichloromethane (1 mL). The resin was shaken for 1 min after which time Davis reagent (0.25 mmol) was added. The resin was shaken overnight at room temperature. The resin was then filtered away from the reaction solution and washed with dichloromethane (3×5 mL), DMF (3×5 mL), and again with dichloromethane (3×5 mL). The desired sulfoxide resin was carried onto the next step as is.

To a 4 mL vial was added sulfoxide resin (0.050 mmol) in anhydrous THF (1 mL). The resin was shaken for 1 min. after which time amine (0.50 mmol) was added. The resin was shaken overnight at room temperature. The resin was then filtered away from the reaction solution and washed with THF (1 mL). The filtrate was evaporated in vacuo to provide the desired product 48.

EXAMPLE 1

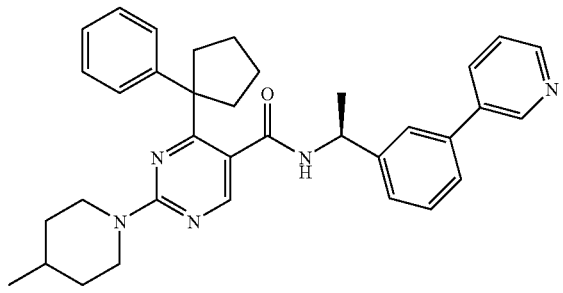

2-(4-Methyl-piperidin-1-yl)-4-(1-phenyl-cylcopentyl)-pyrimidine-5-carboxylic acid [1-(3-pyridin-3-yl-phenyl)-ethyl]-amide. Prepared following procedure A. Product was isolated as an opaque oil (0.0024 g, 18% yield). $^1$H NMR (CDCl$_3$, 400 MHz): δ 8.78 (m, 1H), 8.59 (dd, 1H, J=3.2, 1.6 Hz), 8.24 (s, 1H), 7.82 (m, 1H), 7.43 (m, 1H), 7.38–7.34 (m, 2H), 7.20–7.05 (m, 7H), 5.14 (d, 1H, J=6.2 Hz), 4.88 (m, 1H), 4.82 (d, 2H, J=11.7 Hz), 2.91 (m, 2H), 2.69 (m, 1H), 2.48 (m, 1H), 2.34 (m, 1H), 1.92 (m, 1H), 1.74–1.59 (m, 11H), 1.17 (d, 3H, J=10.5 Hz), 0.97 (d, 2H, J=7.1 Hz). LRMS: 546 [M+H]$^+$; LCMS retention time: 2.66 min.

EXAMPLE 2

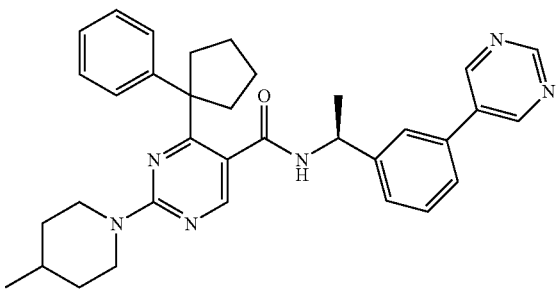

2-(4-Methyl-piperidin-1-yl)-4-(1-phenyl-cyclopentyl)-pyrimidine-5-carboxylic acid [1-(3-pyrimidin-5-yl-phenyl)-ethyl]-amide. Prepared following procedure A. Product was isolated as a clear and colorless oil (0.0024 g, 26% yield). $^1$H NMR (CDCl$_3$, 400 MHz): δ 9.20 (s, 1H), 8.89 (s, 2H), 8.24 (s, 1H), 7.41 (m, 2H), 7.25–7.09 (m, 7H), 5.13 (d, 1H, J=8.2 Hz), 4.89–4.80 (m, 3H), 2.92 (m, 2H), 2.72 (m, 1H), 2.46 (m, 1H), 2.37 (m, 1H), 1.91 (m, 1H), 1.75–1.62 (m, 8H), 1.16 (d, 4H, J=5.2 Hz), 0.97 (d, 3H, J=8.3 Hz); LRMS: 547 [M+H]$^+$; LCMS retention time: 2.97 min.

EXAMPLE 3

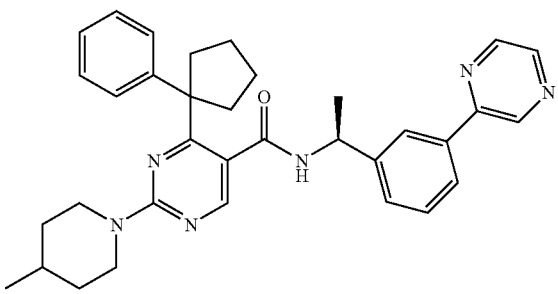

2-(4-Methyl-piperidin-1-yl)-4-(1-phenyl-cyclopentyl)-pyrimidine-5-carboxylic acid [1-(3-pyrazin-2-yl-phenyl)-ethyl]-amide. Prepared following procedure A. Product was isolated as a clear and colorless oil (0.0035 g, 26% yield). $^1$H NMR (CDCl$_3$, 400 MHz): δ 8.98 (s, 1H), 8.64 (s, 1H), 8.51 (s, 1H), 8.25 (s, 1H), 7.85 (d, 1H, J=7.7 Hz), 7.77 (s, 1H), 7.40, (t, 1H, J=7.7 Hz), 7.22–7.15 (m, 5H), 7.08 (t, 1H, J=7.7 Hz), 5.15 (d, 1H, J=6.9 Hz), 4.91–4.81 (m, 3H), 2.92 (m, 2H), 2.66 (m, 1H), 2.49 (m, 1H), 2.32 (m, 1H), 1.95 (m, 1H), 1.75–1.55 (m, 8H), 1.16 (m, 4H), 0.97 (d, 3H, J=8.3 Hz); LRMS: 547.3 [M+H]$^+$; LCMS retention time: 1.99 min.

EXAMPLE 4

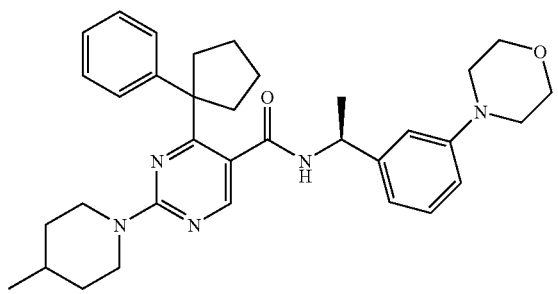

(S)-2-(4-Methyl-piperidin-1-yl)-4-(1-phenyl-cyclopentyl)-pyrimidine-5-carboxylic acid [1-(3-morpholin-4-yl-phenyl)-ethyl]-amide. Prepared following procedure A. Product was isolated as a clear and colorless oil (0.006 g, 61% yield). $^1$H NMR (CDCl$_3$, 400 MHz): δ 8.21 (s, 1H), 7.21–7.10 (m, 6H), 6.76 (d, 1H, J=7.9 Hz), 6.67 (s, 1H), 6.52 (d, 1H, J=7.9 Hz), 5.07 (d, 1H, J=7.6 Hz), 4.83–4.76 (m, 3H), 3.84 (m, 4H), 3.11 (m, 4H), 2.92 (t, 2H, J=12.5 Hz), 2.65 (m, 1H), 2.47 (m, 1H), 2.35 (m, 1H), 1.95 (m, 1H), 1.74–1.59 (m, 6H), 1.21 (m, 2H), 1.12(d, 3H, J=7.2 Hz), 0.97 (d, 3H, J=7.2 Hz); LRMS: 554.3 [M+H]$^+$.

EXAMPLE 5

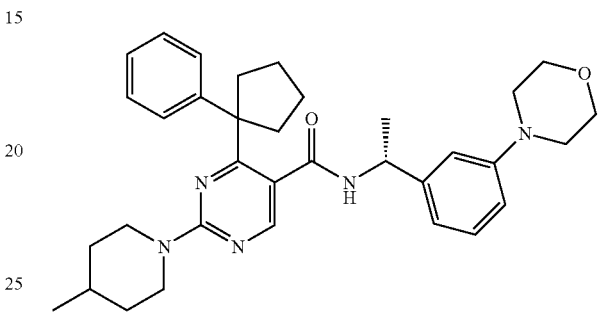

(R)-2-(4-Methyl-piperidin-1-yl)-4-(1-phenyl-cyclopentyl)-pyrimidine-5-carboxylic acid [1-(3-morpholin-4-yl-phenyl)-ethyl]-amide. Prepared following procedure A. Product was isolated as a clear and colorless oil (0.055 g, 52% yield). $^1$H NMR (CDCl$_3$, 400 MHz): δ 8.21 (s, 1H), 7.21–7.10 (m, 6H), 6.76 (d, 1H, J=7.9 Hz), 6.67 (s, 1H), 6.52 (d, 1H, J=7.9 Hz), 5.07 (d, 1H, J=7.6 Hz), 4.83–4.76 (m, 3H), 3.84 (m, 4H), 3.11 (m, 4H), 2.92 (t, 2H, J=12.5 Hz), 2.65 (m, 1H), 2.47 (m, 1H), 2.35 (m, 1H), 1.95 (m, 1H), 1.74–1.59 (m, 6H), 1.21 (m, 2H), 1.12 (d, 3H, J=7.2 Hz), 0.97 (d, 3H, J=7.2 Hz); LRMS: 554.4 [M+H]$^+$; HPLC ret time 3.06 min.

EXAMPLE 6

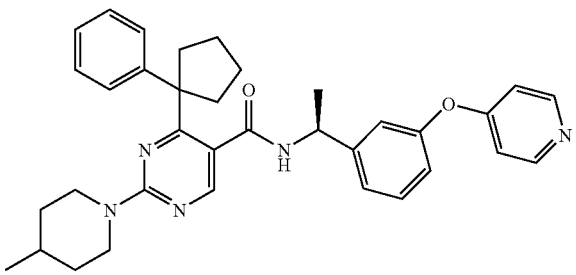

(S)-2-(4-Methyl-piperidin-1-yl)-4-(1-phenyl-cyclopentyl)-pyrimidine-5-carboxylic acid {1-[3-(pyridin-4-yloxy)-phenyl]-ethyl}-amide. Prepared following procedure A. Product was isolated as a clear and colorless oil (0.003 g, 23% yield). $^1$H NMR (CDCl$_3$, 400 MHz): δ 8.47 (brs, 1H), 8.22 (s, 1H), 7.30 (t, 1H, J=7.7 Hz), 7.23–7.09 (m, 5H), 6.96 (d, 1H, J=7.2 Hz), 6.93 (d, 1H, J=7.2 Hz), 6.81 (m, 1H), 6.77 (t, 1H, J=2.0 Hz), 5.07 (d, 1H, J=7.2 Hz), 4.84–4.75 (m, 3H), 2.92 (t, 2H, J=12.8 Hz), 2.69 (m, 1H), 2.48 (m, 1H), 2.35 (m, 1H), 1.89 (m, 1H), 1.75–1.62 (m, 6H), 1.16 (m, 2H), 1.09 (d, 3H, J=7.2 Hz), 0.97 (d, 3H, J=7.2 Hz); LRMS: 562.3 [M+H]$^+$.

EXAMPLE 7

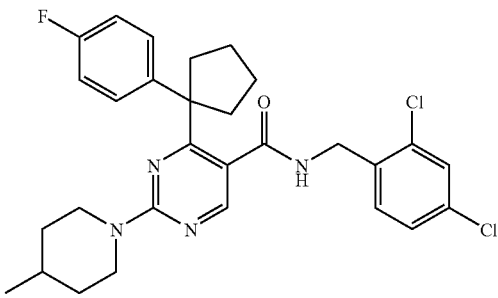

4-[1-(4-Fluoro-phenyl)-cyclopentyl]-2-(4-methyl-piperidin-1-yl)-pyrimidine-5-carboxylic acid 2,4-dichlorobenzylamide. Prepared following procedure B. Product isolated as a clear oil (0.121 g, 13% overall yield). $^1$H NMR (CDCl$_3$, 400 MHz): δ 8.13 (s, 1H), 7.32 (d, 1H, 3.4 Hz), 7.16 (dd, 1H, J=5.6, 2.4 Hz), 7.11–7.07 (m, 3H), 6.80 (t, 2H, J=8.35 Hz), 5.32 (m, 1H), 4.81 (d, 2H, J=13.2 Hz), 4.16 (d, 2H, J=7.1 Hz), 2.90 (m, 2H), 2.55 (m, 2H), 2.11 (m, 2H), 1.74–1.63 (m, 7H), 1.26–1.13 (m, 3H), 0.97 (d, 3H, J=11.3 Hz); LRMS: 541 [M+H]$^+$; LCMS retention time: 2.26 min.

EXAMPLE 8

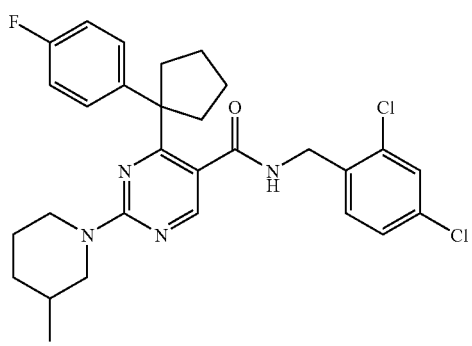

4-[1-(4-Fluoro-phenyl)-cyclopentyl]-2-(3-methyl-piperidin-1-yl)-pyrimidine-5-carboxylic acid 2,4-dichlorobenzylamide. Prepared following procedure B. Product isolated as a pale yellow oil (0.038 g, 14% overall yield). $^1$H NMR (CDCl$_3$, 400 MHz): δ 8.15 (s, 1H), 7.33 (d, 1H, 2.4 Hz), 7.19 (m, 1H), 7.13–7.09 (m, 3H), 6.85 (m, 2H), 5.22 (t, 1H, J=5.9 Hz), 4.66 (m, 2H), 4.17 (d, 2H, J=6.2 Hz), 2.96 (m, 1H), 2.65 (t, 1H, J=11.6 Hz), 2.60–2.53 (m, 2H), 2.14–2.09 (m, 2H), 1.86 (d, 1H, J=12.2 Hz), 1.73–1.62 (m, 7H), 1.33–1.17 (m, 1H), 0.96 (d, 3H, J=8.2 Hz); LRMS: 541 [M+H]$^+$; LCMS retention time: 2.23 min.

EXAMPLE 9

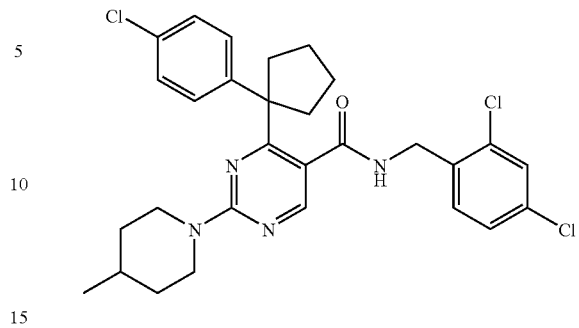

4-[1-(4-Chloro-phenyl)-cyclopentyl]2-(4-methyl-piperidin-1-yl)-pyrimidine-5-carboxylic acid 2,4-dichloro-benzylamide. Prepared following procedure B. A white solid was isolated (0.057 g, 20% overall yield). $^1$H NMR (CDCl$_3$, 400 MHz): δ 8.14 (s, 1H), 7.34 (d, 1H, J=2.5 Hz), 7.19 (dd, 1H, J=5.8, 2.2 Hz), 7.09 (dd, 3H, J=8.8, 4.7 Hz), 5.21 (t, 1H, J=6.3 Hz), 4.83–4.79 (d, 2H, J=13.8 Hz), 4.16 (d, 2H, J=6.3 Hz), 2.91 (t, 2H, J=13.9 Hz), 2.60–2.52 (m, 2H), 2.14–2.07 (m, 2H), 1.74–1.63 (m, 8H), 1.15 (m, 3H), 0.97 (d, 3H, J=6.3 Hz); LRMS: 557 [M+H]$^+$; LCMS retention time: 2.33 min.

EXAMPLE 10

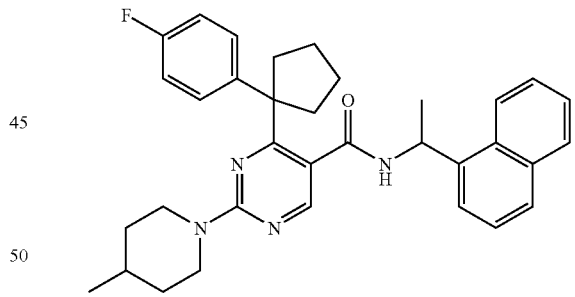

4-[1-(4-Fluoro-phenyl)-cyclopentyl]-2-(4-methyl-piperidin-1-yl)-pyrimidine-5-carboxylic acid (1-naphthalen-1ylethyl)-amide. Prepared following procedure B. Isolated as a white solid (0.020 g, 5% overall yield). $^1$H NMR (CDCl$_3$, 400 MHz): δ 8.14 (s, 1H), 8.04 (d, 1H, J=8.3 Hz), 7.86 (m, 1H), 7.79 (d, 1H, J=8.4 Hz), 7.55–7.47 (m, 2H), 7.40 (t, 1H, J=6.9 Hz), 7.24 (t, 1H, J=5.1 Hz), 6.99 (m, 2H), 6.75 (t, 2H, J=8.9 Hz), 5.77–5.70 (m, 1H), 5.16 (d, 1H, J=8.2 Hz), 4.78 (d, 2H, J=15.2 Hz), 2.90 (t, 2H, J=12.7 Hz), 2.65–2.58 (m, 1H), 2.50–2.43 (m, 1H), 2.39–2.32 (m, 1H), 1.90–1.84 (m, 1H), 1.73–1.62 (m, 7H), 1.40 (d, 3H, J=6.7 Hz), 1.18–1.09 (m, 2H), 0.96 (d, 3H, J=6.5 Hz); LRMS: 537 [M+H]$^+$; LCMS retention time 2.10 min.

EXAMPLE 11

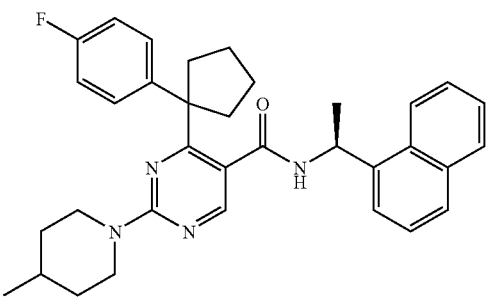

R-4-[1-(4-fluoro-phenyl)-cyclopentyl]-2-(4-methyl-piperidin-1-yl)-pyrimidine-5-carboxylic acid (1-naphthalen-1-yl-ethyl)-amide. Prepared following procedure B. Isolated as a light yellow solid (0.018 g, 7% overall yield). $^1$H NMR (CDCl$_3$, 400 MHz): δ 8.14 (s, 1H), 8.04 (d, 1H, J=8.3 Hz), 7.86 (m, 1H), 7.79 (d, 1H, J=8.4 Hz), 7.55–7.47 (m, 2H), 7.40 (t, 1H, J=6.9 Hz), 7.24 (t, 1H, J=5.1 Hz), 6.99 (m, 2H), 6.75 (t, 2H, J=8.9 Hz), 5.77–5.70 (m, 1H), 5.16 (d, 1H, J=8.2 Hz), 4.78 (d, 2H, J=15.2 Hz), 2.90 (t, 2H, J=12.7 Hz), 2.65–2.58 (m, 1H), 2.50–2.43 (m, 1H), 2.39–2.32 (m, 1H), 1.90–1.84 (m, 1H), 1.73–1.62 (m, 7H), 1.40 (d, 3H, J=6.7 Hz), 1.18–1.09 (m, 2H), 0.96 (d, 3H, J=6.5 Hz); LRMS: 537 [M+H]$^+$; LCMS retention time: 2.06 min.

EXAMPLE 12

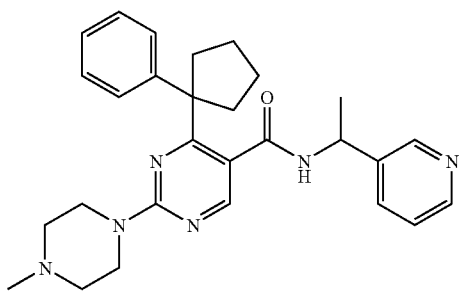

2-(4-Methyl-piperazin-1-yl)-4-(1-phenyl-cyclopentyl)-pyrimidine-5-carboxylic acid (1-pyridin-3-yl-ethyl)-amide. Prepared following procedure B. Isolated as a light yellow solid (0.039 g, 26% overall yield). $^1$H NMR (CDCl$_3$, 400 MHz): δ 8.48 (d, 1H, J=4.2 Hz), 8.35 (s, 1H), 8.25 (s, 1H), 7.36 (d, 1H, J=8.3 Hz), 7.25–7.12 (m, 6H), 5.09 (d, 1H, J=6.3 Hz), 4.81 (m, 1H), 3.98 (m, 4H), 2.63 (m, 1H), 2.54 (m, 4H), 2.49(m, 1H), 2.39 (s, 3H), 2.30 (m, 1H), 1.95 (m, 1H), 1.76–1.62 (m, 4H), 1.14 (d, 3H, J=7.3 Hz); LRMS:. 471.3 [M+H]$^+$.

EXAMPLE 13

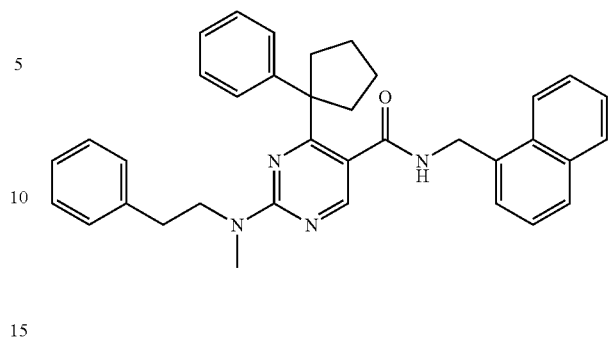

2-(Methyl-phenethyl-amino)-4-(1-phenyl-cyclopentyl)-pyrimidine-5-carboxylic acid (naphthalen-1-ylmethyl)-amide. Prepared following procedure C. Product isolated as a pale yellow oil (0.247 g, 70% yield). $^1$H NMR (CDCl$_3$, 400 MHz): δ 8.25 (s, 1H), 7.87–7.79 (m, 3H), 7.52–7.48 (m, 2H), 7.38 (t, 1H, J=7.4 Hz), 7.30–7.18 (m, 6H), 7.04 (s, 5H), 4.95 (t, 1H, J=5.4 Hz), 4.58 (d, 2H, J=5.4 Hz), 3.93 (s, 2H), 3.15 (s, 3H), 2.95 (t, 2H, J=5.6 Hz), 2.64–2.58 (m, 2H), 2.20–2.15 (m, 2H), 1.71–1.66 (m, 4H); LRMS: 541 [M+H]$^+$; LCMS retention time: 2.10 min.

EXAMPLE 14

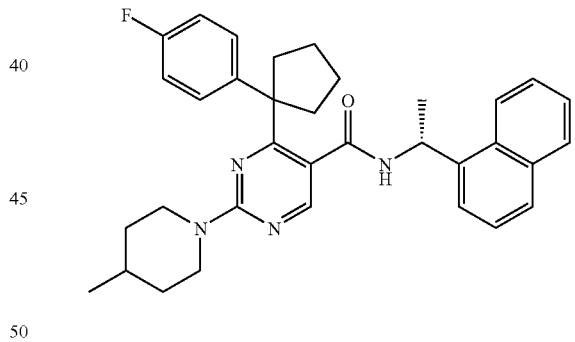

S-4-[1-(4-fluoro-phenyl)-cyclopentyl]-2-(4-methyl-piperidin-1-yl)-pyrimidine-5-carboxylic acid (1-naphthalen-1-yl-ethyl)-amide. Prepared following procedure C starting with 4-fluorophenylcyclopentane carboxylic acid. Product isolated as a slightly orange oil (0.012 g, 35% yield). $^1$H NMR (CDCl$_3$, 400 MHz): δ 8.14 (s, 1H), 8.04 (d, 1H, J=8.3 Hz), 7.86 (m, 1H), 7.79 (d, 1H, J=8.4 Hz), 7.55–7.47 (m, 2H), 7.40 (t, 1H, J=6.9 Hz), 7.24 (t, 1H, J=5.1 Hz), 6.99 (m, 2H), 6.75 (t, 2H, J=8.9 Hz), 5.77–5.70 (m, 1H), 5.16 (d, 1H, J=8.2 Hz), 4.78 (d, 2H, J=15.2 Hz), 2.90 (t, 2H, J=12.7 Hz), 2.65–2.58 (m, 1H), 2.50–2.43 (m, 1H), 2.39–2.32 (m, 1H), 1.90–1.84 (m, 1H), 1.73–1.62 (m, 7H), 1.40 (d, 3H, J=6.7 Hz), 1.18–1.09 (m, 2H), 0.96 (d, 3H, J=6.5 Hz); LRMS: 537 [M+H]$^+$; LCMS retention time: 2.06 min.

EXAMPLE 15

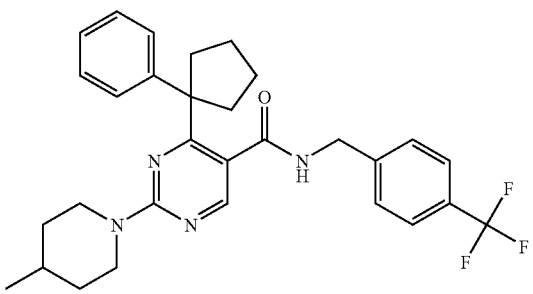

2-(4-Methyl-piperidin-1-yl)-4-(1-phenyl-cylcopentyl)-pyrimidine-5-carboxylic acid 4-trifluoromethyl-benzylamide. Prepared following procedure C. Product isolated as white solid (0.33 g, 73% yield). $^1$H NMR (CDCl$_3$, 400 MHz): δ 8.23 (s, 1H), 7.51 (d, 2H, J=8.2 Hz), 7.21–7.11 (m, 7H), 4.99 (t, 1H, J=5.8 Hz), 4.84 (d, 2H, J=12.6 Hz), 4.12 (d, 2H, J=5.5 Hz), 2.98–2.90 (m, 2H), 2.61–2.55 (m, 2H), 2.17–2.12 (m, 2H), 1.76–1.67 (m, 7H), 1.24–1.13 (m, 2H), 0.98 (d, 3H, J=4.5 Hz); LRMS: 523 [M+H]$^+$; LCMS retention time: 2.06 min.

EXAMPLE 16

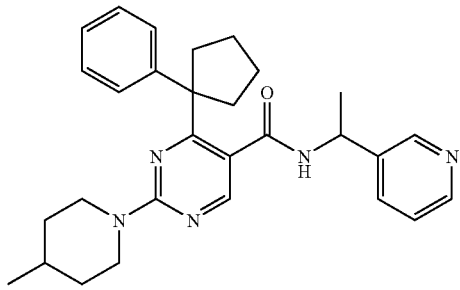

2-(4-Methyl-piperidin-1-yl)-4-(1-phenyl-cyclopentyl)-pyrimidine-5-carboxylic acid (1-pyridin-3-yl-ethyl)-amide. Prepared following procedure C. Product isolated as white solid (0.33 g, 73% yield). $^1$H NMR (CDCl$_3$, 400 MHz): δ 8.47 (d, 1H, J=3.8 Hz), 8.35 (s, 1H), 8.24 (s, 1H), 7.38 (d, 1H, J=7.5 Hz), 7.22–7.13 (m, 6H), 5.08 (d, 1H, J=7.5 Hz), 4.85–4.77 (m, 3H), 2.92 (t, 2H, J=12.2 Hz), 2.64 (m, 1H), 2.50 (m, 1H), 2.27 (m, 1H), 1.92 (m, 1H), 1.74–1.65 (m, 8H), 1.17 (m, 1H), 1.13 (d, 3H, J=7.10), 0.98 (d, 3H, J=6.4 Hz); LRMS: 470.1 [M+H]$^+$; LCMS retention time: 2.58 min.

EXAMPLE 17

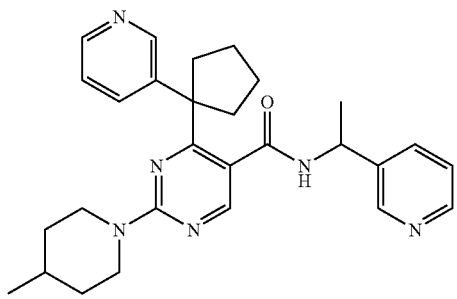

2-(4-Methyl-piperidin-1-yl)-4-(1-pyridin-3-yl-cyclopentyl)-pyrimidine-5-carboxylic acid (1-pyridin-3-yl-ethyl) amide. Prepared following procedure D. Product isolated as a yellow solid (0.017 g, 12% overall yield). $^1$H NMR (CDCl$_3$, 400 MHz): δ 8.48 (d, 1H, J=4.3 Hz), 8.44 (s, 1H), 8.23 (d, 1H, J=3.8 Hz), 8.11 (s, 1H), 8.05 (s, 1H), 7.62 (d, 1H, J=7.6 Hz), 7.46 (d, 1H, J=7.6 Hz), 7.21 (dd, 1H, J=8.0, 4.6 Hz), 7.12 (dd, 1H, J=8.4, 4.9 Hz), 6.29 (s, 1H), 4.8 (d, 2H, J=11.8 Hz), 4.71 (t, 1H, J=7.2 Hz), 2.96–2.88 (m, 2H), 2.79–2.72 (m, 1H), 2.54–2.47 (m, 1H), 2.39–2.32 (m, 1H), 1.98–1.91 (m, 1H), 1.76–1.59 (m, 7H), 1.18 (d, 5H, J=6.9 Hz), 0.98 (d, 3H, J=6.3 Hz); LRMS: 471.3 [M+H]$^+$; LCMS retention time: 1.35 min.

EXAMPLE 18

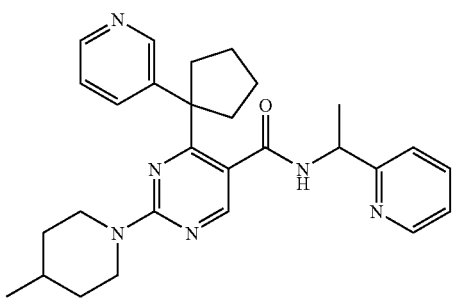

2-(4-Methyl-piperidin-1-yl)-4-(1-pyridin-3-yl-cyclopentyl)-pyrimidine-5-carboxylic acid (1-pyridin-2-yl-ethyl)-amide. Prepared following procedure D. Product isolated as a yellow oil (0.035 g, 26% overall yield). $^1$H NMR (CDCl$_3$, 400 MHz): δ 8.92 (d, 1H, J=6.5 Hz), 8.68 (d, 1H, J=5.2 Hz), 8.63 (s, 1H), 8.55 (d, 1H, J=6.5 Hz), 8.47 (s, 1H), 8.38 (t, 1H, J=7.2 Hz), 8.14 (d, 1H, J=7.9 Hz), 7.91 (d, 1H, J=7.6 Hz), 7.80 (t, 1H, J=6.7 Hz), 7.74 (dd, 1H, J=8.2, 5.7 Hz), 4.95 (m, 1H, J=7.4 Hz), 4.74 (d, 2H, J=11.1 Hz), 3.05 (t, 2H, J=11.4 Hz), 2.73–2.64 (m, 1H), 2.46–2.39 (m, 1H), 2.18–2.11 (m, 2H), 1.83–1.64 (m, 7H), 1.54 (d, 3H, J=6.8 Hz), 1.28–1.18 (m, 2H), 1.0 (d, 3H, J=6.4 Hz); LRMS: 471.2 [M+H]$^+$; LCMS retention time: 1.39 min.

EXAMPLE 19

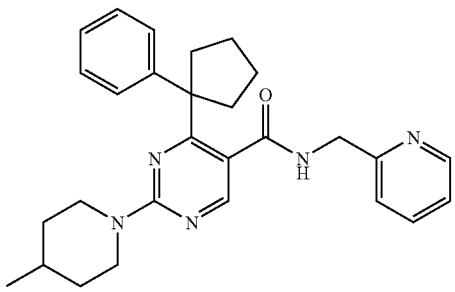

2-(4-Methyl-piperidin-1-yl)-4-(1-phenyl-cyclopentyl)-pyrimidine-5-carboxylic acid (pyridin-2-ylmethyl)-amide. Prepared following procedure E. Product isolated as a yellow oil (0.030 g, 26% overall yield). $^1$H NMR (CDCl$_3$, 400 MHz): δ 8.41 (d, 1H, J=4.5 Hz), 8.18 (s, 1H), 7.61 (t, 1H, J=7.6 Hz), 7.20–7.07 (m, 5H), 6.88 (t, 1H, J=7.6 Hz), 5.97 (t, 1H, J=3.8), 4.83 (d, 2H, J=11.0 Hz), 4.20 (d, 2H, J=5.3 Hz), 2.93 (dt, 2H, J=12.8, 2.3 Hz), 2.66–2.57 (m, 2H), 2.25–2.16 (m, 2H), 1.76–1.65 (m, 7H), 1.21 (dq, 2H, J=12.1, 4.6 Hz), 0.99 (d, 3H, J=6.1 Hz); LRMS: 456.3 [M+H]$^+$.

EXAMPLE 20

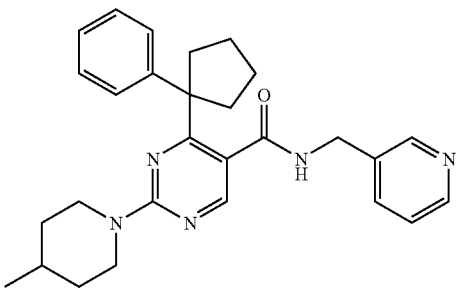

2-(4-Methyl-piperidin-1-yl)-4-(1-phenyl-cyclopentyl)-pyrimidine-5-carboxylic acid (pyridin-3-ylmethyl)-amide. Prepared following procedure E. Product isolated as a yellow oil (0.040 g, 35% overall yield). $^1$H NMR (CDCl$_3$, 400 MHz): δ 8.51 (d, 1H, J=5.6 Hz), 8.31 (d, 1H, J=2.5 Hz), 8.23 (s, 1H), 7.42 (d, 1H, J=8.4 Hz), 7.23–7.12 (m, 7H), 4.98 (t, 1H, J=5.4 Hz), 4.83 (d, 2H, J=11.0 Hz), 4.08 (d, 2H, J=5.4 Hz), 2.93 (dt, 2H, J=13.0, 2.7 Hz), 2.6–2.5 (m, 2H), 2.17–2.10 (m, 2H), 1.76–1.73 (m, 2H), 1.71–1.66 (m, 5H), 1.18 (dq, 2H, J=11.8, 4.6 Hz), 0.98 (d, 3H, J=6.1 Hz); LRMS: 455 [M]$^+$.

EXAMPLE 21

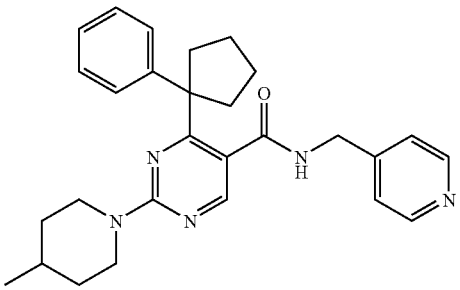

2-(4-Methyl-piperidin-1-yl)-4-(1-phenyl-cyclopentyl)-pyrimidine-5-carboxylic acid (pyridin-4-ylmethyl)-amide. Prepared following procedure E. Product isolated as a yellow oil (0.035 g, 32% overall yield). $^1$H NMR (CDCl$_3$, 400 MHz): δ 8.50 (d, 2H, J=5.1 Hz), 8.25 (s, 1H), 7.24–7.14 (m, 5H), 6.98 (d, 1H, J=5.1 Hz), 5.09 (t, 1H, J=5.5 Hz), 4.85 (d, 2H, J=1.0 Hz), 4.09 (d, 2H, J=5.5 Hz), 2.95 (dt, 2H, J=12.4, 2.5 Hz), 2.63–2.55 (m, 2H), 2.19–2.12 (m, 2H), 1.77–1.74 (m, 2H), 1.72–1.68 (m, 5H), 1.19 (dq, 2H, J=11.8, 4.2 Hz), 0.99 (d, 3H, J=6.3 Hz); LRMS: 456.3 [M+H]$^+$.

EXAMPLE 22

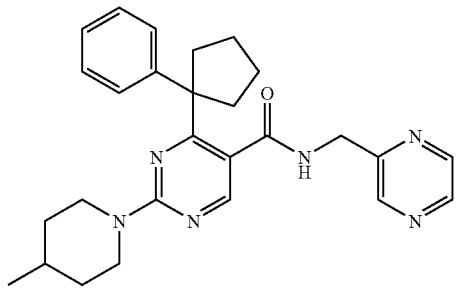

2-(4-Methyl-piperidin-1-yl)-4-(1-phenyl-cyclopentyl)-pyrimidine-5-carboxylic acid (pyrazin-2-ylmethyl)-amide. Prepared following procedure E. Product isolated as a yellow oil (0.003 g, 3% overall yield). $^1$H NMR (CDCl$_3$, 400 MHz): δ 8.39–8.32 (m, 3H), 8.12 (s, 1H), 7.11 (d, 2H, J=8.0 Hz), 7.03 (d, 2H, J=8.0 Hz), 6.83 (t, 1H, J=7.2 Hz), 5.69 (m, 1H), 4.79 (d, 2H, J=11.0 Hz), 4.16 (d, 2H, J=4.8 Hz), 2.90 (m, 2H), 2.57–2.52 (m, 2H), 2.15–2.10 (m, 2H), 1.71–1.60 (m, 7H), 1.16 (dq, 2H, J=11.8, 4.2 Hz), 0.93 (d, 3H, J=6.4 Hz); LRMS: 457.2 [M+H]$^+$; Notebook #: 48148-043.

EXAMPLE 23

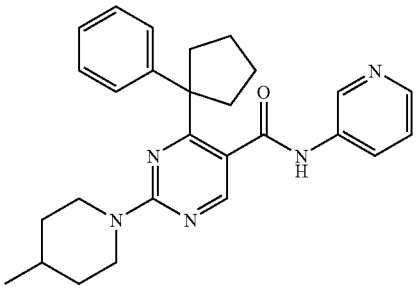

2-(4-Methyl-piperidin-1-yl)-4-(1-phenyl-cyclopentyl)-pyrimidine-5-carboxylic acid pyridin-3-ylamide. Prepared following procedure E. Product isolated as a yellow oil (0.006 g, 5% overall yield). $^1$H NMR (CDCl$_3$, 400 MHz): δ 8.39 (s, 1H), 8.27 (d, 1H, J=5.5 Hz), 7.93 (d, 2H, J=8.6 Hz), 7.77 (d, 2H, J=2.7 Hz), 7.32–7.18 (m, 5H), 6.51 (s, 1H), 4.88 (d, 2H, J=12.7 Hz), 2.98 (d, 2H, J=12.7, 2.3 Hz), 2.62–2.55 (m, 2H), 2.21–2.14 (m, 2H), 1.80–1.67 (m, 7H), 1.23 (dq, 2H, J=12.3, 3.2 Hz), 1.01 (d, 3H, J=6.8 Hz); LRMS: 442.2 [M+H]$^+$.

EXAMPLE 24

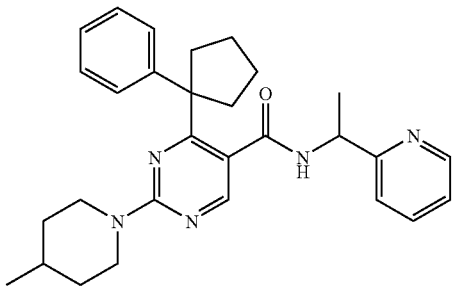

2-(4-Methyl-piperidin-1-yl)-4-(1-phenyl-cyclopentyl)-pyrimidine-5-carboxylic acid (1-pyridin-2-yl-ethyl)-amide. Prepared following procedure E. Product isolated as a yellow oil (0.056 g, 32% overall yield). $^1$H NMR (CDCl$_3$, 400 MHz): δ 8.41 (d, 1H, J=4.1 Hz), 8.18 (s, 1H), 7.63 (t, 1H, J=7.6 Hz), 7.17–7.03 (m, 5H), 6.82 (t, 1H, J=7.3 Hz), 6.33 (t, 1H, J=3.8), 4.84 (d, 2H, J=12.7 Hz), 4.74 (m, 1H, J=6.5 Hz), 2.93 (t, 2H, J=12.7 Hz), 2.67–2.57 (m, 2H), 2.26–2.14 (m, 2H), 1.76–1.66 (m, 7H), 1.17 (dq, 2H, J=12.1, 4.6 Hz), 0.98 (d, 3H, J=6.1 Hz); LRMS: 470.3 [M+H]$^+$; LCMS retention time: 1.81 min.

Some examples of Formula I compounds are listed in the following Tables 2–4.

TABLE 2

| Example no. | Compound Name | hQ23 EC$_{50}$ (uM) | Ret. time (min) | % Purity | e/z M + 1 |
|---|---|---|---|---|---|
| 25 | isoquinoline, 1,2,3,4-tetrahydro-2-[[2-(3-methyl-1-piperidinyl)-4-(1-phenylcyclopropyl)-5-pyrimidinyl]carbonyl]- | 0.945 | 2.65 | 89 | 453.34 |
| 26 | isoquinoline, 1,2,3,4-tetrahydro-2-[[2-(4-methyl-1-piperidinyl)-4-(1-phenylcyclopropyl)-5-pyrimidinyl]carbonyl]- | 0.546 | 2.66 | 88 | 453.34 |
| 27 | 5-pyrimidinecarboxamide, N-cyclohexyl-N-ethyl-2-(4-methyl-1-piperazinyl)-4-(1-phenylcyclopropyl)- | 0.470 | 1.53 | 100 | 448.37 |
| 28 | 5-pyrimidinecarboxamide, 2-[[2-(dimethylamino)ethyl]amino]-N-methyl-4-(1-phenylcyclopropyl)-N-(2-phenylethyl)- | 0.301 | 1.37 | 100 | 444.36 |
| 29 | 5-pyrimidinecarboxamide, N-ethyl-2-[(4-methylcyclohexyl)amino]-4-(1-phenylcyclopropyl)-N-(phenylmethyl)- | 0.607 | 2.1 | 80 | 469.35 |
| 30 | 5-pyrimidinecarboxamide, N-ethyl-2-(3-methyl-1-piperidinyl)-4-(1-phenylcyclopropyl)-N-(phenylmethyl)- | 0.634 | 2.65 | 85 | 455.35 |
| 31 | 5-pyrimidinecarboxamide, N-ethyl-2-(4-methyl-1-piperidinyl)-4-(1-phenylcyclopropyl)-N-(phenylmethyl)- | 0.475 | 2.67 | 87 | 455.35 |
| 32 | 5-pyrimidinecarboxamide, N-(1,3-benzodioxol-5-ylmethyl)-4-(1-phenylcyclopropyl)-2-(1-pyrrolidinyl)- | 0.413 | 1.7 | 73 | 443.27 |
| 33 | 5-pyrimidinecarboxamide, 2-[(4-methylcyclohexyl)amino]-N-[(1R)-1-(1-naphthalenyl)ethyl]-4-(1-phenylcyclopropyl)- | 0.293 | 2.11 | 91 | 505.35 |
| 34 | 5-pyrimidinecarboxamide, 2-(3-methyl-1-piperidinyl)-N-[(1R)-1-(1-naphthalenyl)ethyl]-4-(1-phenylcyclopropyl)- | 0.107 | 2.69 | 86 | 491.36 |
| 35 | 5-pyrimidinecarboxamide, 2-(4-methyl-1-piperidinyl)-N-[(1R)-1-(1-naphthalenyl)ethyl]-4-(1-phenylcyclopropyl)- | 0.212 | 2.65 | 90 | 491.36 |
| 36 | 5-pyrimidinecarboxamide, 2-[(4-methylcyclohexyl)amino]-N-(1-naphthalenylmethyl)-4-(1-phenylcyclopropyl)- | 0.586 | 2.08 | 94 | 491.33 |
| 37 | 5-pyrimidinecarboxamide, 2-(3-methyl-1-piperidinyl)-N-(1-naphthalenylmethyl)-4-(1-phenylcyclopropyl)- | 0.214 | 2.68 | 90 | 477.33 |
| 38 | 5-pyrimidinecarboxamide, 2-(4-methyl-1-piperidinyl)-N-(1-naphthalenylmethyl)-4-(1-phenylcyclopropyl)- | 0.381 | 2.62 | 85 | 477.34 |
| 39 | 5-pyrimidinecarboxamide, N-[(2,4-dichlorophenyl)methyl]-2-[(4-methylcyclohexyl)amino]-4-(1-phenylcyclopropyl)- | 0.551 | 2.76 | 94 | 509.25 |

TABLE 2-continued

| Example no. | Compound Name | hQ23 EC$_{50}$ (uM) | Ret. time (min) | % Purity | e/z M + 1 |
|---|---|---|---|---|---|
| 40 | 5-pyrimidinecarboxamide, N-[(2,4-dichlorophenyl)methyl]-2-(3-methyl-1-piperidinyl)-4-(1-phenylcyclopropyl)- | 0.326 | 2.7 | 80 | 495.25 |
| 41 | 5-pyrimidinecarboxamide, N-[(2,4-dichlorophenyl)methyl]-2-(4-methyl-1-piperidinyl)-4-(1-phenylcyclopropyl)- | 0.220 | 2.66 | 85 | 495.25 |
| 42 | 5-pyrimidinecarboxamide, N-[(2,4-difluorophenyl)methyl]-2-[(4-methylcyclohexyl)amino]-4-(1-phenylcyclopropyl)- | 0.413 | 1.99 | 100 | 477.3 |
| 43 | 5-pyrimidinecarboxamide, N-[(2,4-difluorophenyl)methyl]-2-(4-methyl-1-piperidinyl)-4-(1-phenylcyclopropyl)- | 0.919 | 2.57 | 81 | 463.3 |
| 44 | 5-pyrimidinecarboxamide, N-[[3-fluoro-5-(trifluoromethyl)phenyl]methyl]-2-[(4-methylcyclohexyl)amino]-4-(1-phenylcyclopropyl)- | 0.044 | 2.69 | 88 | 527.31 |
| 45 | 5-pyrimidinecarboxamide, N-[[3-fluoro-5-(trifluoromethyl)phenyl]methyl]-4-(1-phenylcyclopropyl)-2-(1-pyrrolidinyl)- | 0.209 | 0.33 | 72 | 485.27 |
| 46 | 5-pyrimidinecarboxamide, N-[[3-fluoro-5-(trifluoromethyl)phenyl]methyl]-2-(4-methyl-1-piperazinyl)-4-(1-phenylcyclopropyl)- | 0.384 | 2.09 | 98 | 514.31 |
| 47 | 5-pyrimidinecarboxamide, N-[[3-fluoro-5-(trifluoromethyl)phenyl]methyl]-2-(3-methyl-1-piperidinyl)-4-(1-phenylcyclopropyl)- | 0.041 | 2.6 | 76 | 513.31 |
| 48 | 5-pyrimidinecarboxamide, N-[[3-fluoro-5-(trifluoromethyl)phenyl]methyl]-2-(4-methyl-1-piperidinyl)-4-(1-phenylcyclopropyl)- | 0.297 | 2.62 | 71 | 513.31 |
| 49 | 5-pyrimidinecarboxamide, N-[1-(4-fluorophenyl)ethyl]-2-[(4-methylcyclohexyl)amino]-4-(1-phenylcyclopropyl)- | 0.575 | 2 | 100 | 473.32 |
| 50 | 5-pyrimidinecarboxamide, N-[1-(4-fluorophenyl)ethyl]-2-(3-methyl-1-piperidinyl)-4-(1-phenylcyclopropyl)- | 0.673 | 2.53 | 81 | 459.32 |
| 51 | 5-pyrimidinecarboxamide, N-[1-(4-fluorophenyl)ethyl]-2-(4-methyl-1-piperidinyl)-4-(1-phenylcyclopropyl)- | 0.672 | 2.54 | 79 | 459.33 |

TABLE 3

| Example no. | Compound Name | hQ23 EC$_{50}$ (uM) | Ret. time (min) | % Purity | e/z M + 1 |
|---|---|---|---|---|---|
| 52 | 5-pyrimidinecarboxamide, 4-[1-(4-chlorophenyl)cyclobutyl]-N,N-diethyl-2-[(1-methylpropyl)amino]- | 0.211 | 2 | 100 | 415.31 |

TABLE 3-continued

| Example no. | Compound Name | hQ23 EC$_{50}$ (uM) | Ret. time (min) | % Purity | e/z M + 1 |
|---|---|---|---|---|---|
| 53 | 5-pyrimidinecarboxamide, 4-[1-(4-chlorophenyl)cyclobutyl]-2-[[2-(dimethylamino)ethyl]amino]-N,N-diethyl- | 0.558 | 1.42 | 100 | 430.33 |
| 54 | isoquinoline, 2-[[4-[1-(4-chlorophenyl)cyclobutyl]-2-[[2-(dimethylamino)ethyl]amino]-5-pyrimidinyl]carbonyl]-1,2,3,4-tetrahydro- | 0.475 | 1.6 | 100 | 490.33 |
| 55 | 5-pyrimidinecarboxamide, 4-[1-(4-chlorophenyl)cyclobutyl]-2-[[2-(dimethylamino)ethyl]amino]-N-methyl-N-(2-phenylethyl)- | 0.321 | 1.58 | 100 | 492.34 |
| 56 | 5-pyrimidinecarboxamide, N-(1,3-benzodioxol-5-ylmethyl)-4-[1-(4-chlorophenyl)cyclobutyl]-2-(1-pyrrolidinyl)- | 0.719 | 1.98 | 100 | 491.25 |
| 57 | 5-pyrimidinecarboxamide, N-(1,3-benzodioxol-5-ylmethyl)-4-[1-(4-chlorophenyl)cyclobutyl]-2-(4-methyl-1-piperazinyl)- | 0.745 | 2.12 | 83 | 520.29 |
| 58 | 5-pyrimidinecarboxamide, N-(1,3-benzodioxol-5-ylmethyl)-4-[1-(4-chlorophenyl)cyclobutyl]-2-(4-methyl-1-piperidinyl)- | 0.090 | 2.66 | 73 | 519.29 |
| 59 | 5-pyrimidinecarboxamide, N-(1,3-benzodioxol-5-ylmethyl)-4-[1-(4-chlorophenyl)cyclobutyl]-2-[(1-methylpropyl)amino]- | 0.405 | 2.01 | 92 | 493.28 |
| 60 | 5-pyrimidinecarboxamide, 4-[1-(4-chlorophenyl)cyclobutyl]-2-(cyclopropylamino)-N-(1-naphthalenylmethyl)- | 0.614 | 2 | 97 | 483.24 |
| 61 | 5-pyrimidinecarboxamide, 4-[1-(4-chlorophenyl)cyclobutyl]-N-(1-naphthalenylmethyl)-2-(1-pyrrolidinyl)- | 0.079 | 2.13 | 100 | 497.27 |
| 62 | 5-pyrimidinecarboxamide, 4-[1-(4-chlorophenyl)cyclobutyl]-2-(3-methyl-1-piperidinyl)-N-(1-naphthalenylmethyl)- | 0.039 | 2.89 | 89 | 525.32 |
| 63 | 5-pyrimidinecarboxamide, 4-[1-(4-chlorophenyl)cyclobutyl]-N-[(2,4-dichlorophenyl)methyl]-2-(3-methyl-1-piperidinyl)- | 0.014 | 1.35 | 95 | 543.24 |
| 64 | 5-pyrimidinecarboxamide, 4-[1-(4-chlorophenyl)cyclobutyl]-N-[(2,4-dichlorophenyl)methyl]-2-(4-methyl-1-piperidinyl)- | 0.034 | 2.86 | 82 | 543.23 |
| 65 | 5-pyrimidinecarboxamide, 4-[1-(4-chlorophenyl)cyclobutyl]-N-[(2,4-difluorophenyl)methyl]-2-[(4-methylcyclohexyl)amino]- | 0.056 | 2.18 | 92 | 525.28 |
| 66 | 5-pyrimidinecarboxamide, 4-[1-(4-chlorophenyl)cyclobutyl]-N-[[3-fluoro-5- | 0.010 | 2.86 | 81 | 561.31 |

TABLE 3-continued

| Example no. | Compound Name | hQ23 EC$_{50}$ (uM) | Ret. time (min) | % Purity | e/z M + 1 |
|---|---|---|---|---|---|
| | (trifluoromethyl)phenyl]methyl]-2-(3-methyl-1-piperidinyl)- | | | | |
| 67 | 5-pyrimidinecarboxamide, 4-[1-(4-chlorophenyl)cyclobutyl]-N-[[3-fluoro-5-(trifluoromethyl)phenyl]methyl]-2-(4-methyl-1-piperidinyl)- | 0.010 | 2.79 | 86 | 561.31 |
| 68 | 5-pyrimidinecarboxamide, 4-[1-(4-chlorophenyl)cyclobutyl]-N-[1-(4-fluorophenyl)ethyl]-2-(3-methyl-1-piperidinyl)- | 0.128 | 2.74 | 86 | 507.3 |

TABLE 4

| Example no. | Compound Name | hQ23 EC$_{50}$ (uM) | Ret. time (min) | % Purity | e/z M + 1 |
|---|---|---|---|---|---|
| 69 | 5-pyrimidinecarboxamide, N-methyl-4-(1-phenylcyclopentyl)-N-(phenylmethyl)-2-(1-pyrrolidinyl)- | 0.778 | 2.7 | 89 | 441.4 |
| 70 | 5-pyrimidinecarboxamide, N-methyl-2-(4-methyl-1-piperidinyl)-4-(1-phenylcyclopentyl)-N-(phenylmethyl)- | 0.270 | 2.3 | 87 | 469.4 |
| 71 | 5-pyrimidinecarboxamide, 2-(cyclopentylamino)-N-methyl-4-(1-phenylcyclopentyl)-N-(phenylmethyl)- | 0.718 | 2.6 | 79 | 455.4 |
| 72 | 5-pyrimidinecarboxamide, N,N-diethyl-2-[(4-methylcyclohexyl)amino]-4-(1-phenylcyclopentyl)- | 0.576 | 2.7 | 92 | 435.4 |
| 73 | isoquinoline, 1,2,3,4-tetrahydro-2-[[2-[(4-methylcyclohexyl)amino]-4-(1-phenylcyclopentyl)-5-pyrimidinyl]carbonyl]- | 0.798 | 2.7 | 86 | 495.4 |
| 74 | isoquinoline, 1,2,3,4-tetrahydro-2-[[2-(4-methyl-1-piperidinyl)-4-(1-phenylcyclopentyl)-5-pyrimidinyl]carbonyl]- | 0.191 | 2.3 | 100 | 481.4 |
| 75 | isoquinoline, 2-[[2-(cyclopentylamino)-4-(1-phenylcyclopentyl)-5-pyrimidinyl]carbonyl]-1,2,3,4-tetrahydro- | 0.950 | 2.7 | 93 | 467.4 |
| 76 | 5-pyrimidinecarboxamide, N-cyclohexyl-N-ethyl-2-(4-methyl-1-piperidinyl)-4-(1-phenylcyclopentyl)- | 0.900 | 2.4 | 94 | 475.5 |
| 77 | piperidine, 1-[[2-(4-methyl-1-piperidinyl)-4-(1-phenylcyclopentyl)-5-pyrimidinyl]carbonyl]- | 0.164 | 2.2 | 90 | 433.4 |
| 78 | piperidine, 3-methyl-1-[[2-(4-methyl-1-piperidinyl)-4-(1-phenylcyclopentyl)-5-pyrimidinyl]carbonyl]- | 0.775 | 2.3 | 92 | 447.4 |
| 79 | 5-pyrimidinecarboxamide, N-methyl-4-(1-phenylcyclopentyl)-N-(2-phenylethyl)-2-(1-pyrrolidinyl)- | 0.444 | 2.7 | 86 | 455.4 |
| 80 | 5-pyrimidinecarboxamide, N-methyl-2-(3-methyl-1- | 0.880 | 2.2 | 93 | 483.4 |

TABLE 4-continued

| Example no. | Compound Name | hQ23 EC$_{50}$ (uM) | Ret. time (min) | % Purity | e/z M + 1 |
|---|---|---|---|---|---|
| | piperidinyl)-4-(1-phenylcyclopentyl)-N-(2-phenylethyl)- | | | | |
| 81 | 5-pyrimidinecarboxamide, N-methyl-2-(4-methyl-1-piperidinyl)-4-(1-phenylcyclopentyl)-N-(2-phenylethyl)- | 0.437 | 2.3 | 93 | 483.4 |
| 82 | 5-pyrimidinecarboxamide, N,N-bis(1-methylethyl)-2-(3-methyl-1-piperidinyl)-4-(1-phenylcyclopentyl)- | 0.285 | 2.3 | 89 | 447.4 |
| 83 | 5-pyrimidinecarboxamide, N-ethyl-N-methyl-2-(3-methyl-1-piperidinyl)-4-(1-phenylcyclopentyl)- | 0.605 | 2.1 | 82 | 407.4 |
| 84 | 5-pyrimidinecarboxamide, N-ethyl-2-[(4-methylcyclohexyl)amino]-4-(1-phenylcyclopentyl)-N-(phenylmethyl)- | 0.829 | 2.8 | 82 | 497.4 |
| 85 | 5-pyrimidinecarboxamide, N-ethyl-2-(3-methyl-1-piperidinyl)-4-(1-phenylcyclopentyl)-N-(phenylmethyl)- | 0.161 | 2.3 | 94 | 483.4 |
| 86 | 5-pyrimidinecarboxamide, N-ethyl-2-(4-methyl-1-piperidinyl)-4-(1-phenylcyclopentyl)-N-(phenylmethyl)- | 0.334 | 2.3 | 94 | 483.4 |
| 87 | 5-pyrimidinecarboxamide, N-ethyl-2-[(1-methylpropyl)amino]-4-(1-phenylcyclopentyl)-N-(phenylmethyl)- | 0.851 | 2.1 | 100 | 457.4 |
| 88 | 5-pyrimidinecarboxamide, 2-(cyclopentylamino)-N-ethyl-4-(1-phenylcyclopentyl)-N-(phenylmethyl)- | 0.926 | 2.6 | 80 | 469.4 |
| 89 | 5-pyrimidinecarboxamide, N-(1,3-benzodioxol-5-ylmethyl)-2-(cyclopropylamino)-4-(1-phenylcyclopentyl)- | 0.692 | 2.4 | 73 | 457.3 |
| 90 | 5-pyrimidinecarboxamide, N-(1,3-benzodioxol-5-ylmethyl)-2-[(4-methylcyclohexyl)amino]-4-(1-phenylcyclopentyl)- | 0.220 | 2.6 | 79 | 513.4 |
| 91 | 5-pyrimidinecarboxamide, N-(1,3-benzodioxol-5-ylmethyl)-2-(4-methyl-1-piperazinyl)-4-(1-phenylcyclopentyl)- | 0.257 | 1.5 | 100 | 500.4 |
| 92 | 5-pyrimidinecarboxamide, N-(1,3-benzodioxol-5-ylmethyl)-2-(3-methyl-1-piperidinyl)-4-(1-phenylcyclopentyl)- | 0.057 | 2.1 | 83 | 499.4 |
| 93 | 5-pyrimidinecarboxamide, N-(1,3-benzodioxol-5-ylmethyl)-2-(4-methyl-1-piperidinyl)-4-(1-phenylcyclopentyl)- | 0.037 | 2.1 | 78 | 499.4 |
| 94 | 5-pyrimidinecarboxamide, N-(1,3-benzodioxol-5-ylmethyl)-2-[(1-methylpropyl)amino]-4-(1-phenylcyclopentyl)- | 0.301 | 1.9 | 100 | 473.4 |
| 95 | 5-pyrimidinecarboxamide, 2-[(4-methylcyclohexyl)amino]-N-[1-(1-naphthalenyl)ethyl]-4-(1-phenylcyclopentyl)- | 0.064 | 2.7 | 78 | 533.4 |
| 96 | 5-pyrimidinecarboxamide, N-[1-(1-naphthalenyl)ethyl]-4-(1-phenylcyclopentyl)-2-(1-pyrrolidinyl)- | 0.148 | 2.7 | 93 | 491.4 |
| 97 | 5-pyrimidinecarboxamide, 2-(3-methyl-1-piperidinyl)-N-[1- | 0.019 | 2.2 | 95 | 519.4 |

TABLE 4-continued

| Example no. | Compound Name | hQ23 EC$_{50}$ (uM) | Ret. time (min) | % Purity | e/z M + 1 |
|---|---|---|---|---|---|
| 98 | (1-naphthalenyl)ethyl]-4-(1-phenylcyclopentyl)-5-pyrimidinecarboxamide, 2-(4-methyl-1-piperidinyl)-N-[1-(1-naphthalenyl)ethyl]-4-(1-phenylcyclopentyl)- | 0.015 | 2.2 | 95 | 519.4 |
| 99 | 5-pyrimidinecarboxamide, 2-[(1-methylpropyl)amino]-N-[1-(1-naphthalenyl)ethyl]-4-(1-phenylcyclopentyl)- | 0.293 | 2.1 | 75 | 493.4 |
| 100 | 5-pyrimidinecarboxamide, 2-(cyclopentylamino)-N-[1-(1-naphthalenyl)ethyl]-4-(1-phenylcyclopentyl)- | 0.160 | 2.6 | 81 | 505.4 |
| 101 | 5-pyrimidinecarboxamide, 2-(cyclopropylamino)-N-(1-naphthalenylmethyl)-4-(1-phenylcyclopentyl)- | 0.669 | 2.5 | 87 | 463.3 |
| 102 | 5-pyrimidinecarboxamide, 2-[(4-methylcyclohexyl)amino]-N-(1-naphthalenylmethyl)-4-(1-phenylcyclopentyl)- | 0.194 | 2.7 | 76 | 519.4 |
| 103 | 5-pyrimidinecarboxamide, 2-(3-methyl-1-piperidinyl)-N-(1-naphthalenylmethyl)-4-(1-phenylcyclopentyl)- | 0.066 | 2.2 | 95 | 505.4 |
| 104 | 5-pyrimidinecarboxamide, 2-(4-methyl-1-piperidinyl)-N-(1-naphthalenylmethyl)-4-(1-phenylcyclopentyl)- | 0.010 | 2.2 | 97 | 505.4 |
| 105 | 5-pyrimidinecarboxamide, 2-[(1-methylpropyl)amino]-N-(1-naphthalenylmethyl)-4-(1-phenylcyclopentyl)- | 0.604 | 2.1 | 78 | 479.4 |
| 106 | 5-pyrimidinecarboxamide, N-[(3,4-dichlorophenyl)methyl]-2-[(4-methylcyclohexyl)amino]-4-(1-phenylcyclopentyl)- | 0.130 | 2.8 | 87 | 537.3 |
| 107 | 5-pyrimidinecarboxamide, N-[(3,4-dichlorophenyl)methyl]-2-(3-methyl-1-piperidinyl)-4-(1-phenylcyclopentyl)- | 0.111 | 2.2 | 93 | 523.3 |
| 108 | 5-pyrimidinecarboxamide, N-[(3,4-dichlorophenyl)methyl]-2-(4-methyl-1-piperidinyl)-4-(1-phenylcyclopentyl)- | 0.037 | 2.2 | 93 | 523.3 |
| 109 | 5-pyrimidinecarboxamide, 2-(cyclopropylamino)-N-[(2,4-dichlorophenyl)methyl]-4-(1-phenylcyclopentyl)- | 0.504 | 2.6 | 93 | 481.3 |
| 110 | 5-pyrimidinecarboxamide, N-[(2,4-dichlorophenyl)methyl]-2-[(4-methylcyclohexyl)amino]-4-(1-phenylcyclopentyl)- | 0.068 | 2.8 | 73 | 537.3 |
| 111 | 5-pyrimidinecarboxamide, N-[(2,4-dichlorophenyl)methyl]-4-(1-phenylcyclopentyl)-2-(1-pyrrolidinyl)- | 0.192 | 2.7 | 91 | 495.3 |
| 112 | 5-pyrimidinecarboxamide, N-[(2,4-dichlorophenyl)methyl]-2-(3-methyl-1-piperidinyl)-4-(1-phenylcyclopentyl)- | 0.064 | 2.3 | 100 | 523.3 |
| 113 | 5-pyrimidinecarboxamide, N-[(2,4-dichlorophenyl)methyl]-2-(4-methyl-1-piperidinyl)-4-(1-phenylcyclopentyl)- | 0.010 | 2.3 | 92 | 523.3 |
| 114 | 5-pyrimidinecarboxamide, N-[(2,4-dichlorophenyl)methyl]-2-[(1-methylpropyl)amino]-4-(1-phenylcyclopentyl)- | 0.102 | 2.1 | 86 | 497.3 |
| 115 | 5-pyrimidinecarboxamide, 2-(cyclopentylamino)-N-[(2,4-dichlorophenyl)methyl]-4-(1-phenylcyclopentyl)- | 0.136 | 2.7 | 96 | 509.3 |

TABLE 4-continued

| Example no. | Compound Name | hQ23 EC$_{50}$ (uM) | Ret. time (min) | % Purity | e/z M + 1 |
|---|---|---|---|---|---|
| 116 | 5-pyrimidinecarboxamide, N-[(2,4-difluorophenyl)methyl]-2-[(4-methylcyclohexyl)amino]-4-(1-phenylcyclopentyl)- | 0.085 | 2.7 | 91 | 505.4 |
| 117 | 5-pyrimidinecarboxamide, N-[(2,4-difluorophenyl)methyl]-4-(1-phenylcyclopentyl)-2-(1-pyrrolidinyl)- | 0.127 | 2.6 | 100 | 463.3 |
| 118 | 5-pyrimidinecarboxamide, N-[(2,4-difluorophenyl)methyl]-2-(3-methyl-1-piperidinyl)-4-(1-phenylcyclopentyl)- | 0.037 | 2.1 | 84 | 491.4 |
| 119 | 5-pyrimidinecarboxamide, N-[(2,4-difluorophenyl)methyl]-2-(4-methyl-1-piperidinyl)-4-(1-phenylcyclopentyl)- | 0.122 | 2.1 | 78 | 491.4 |
| 120 | 5-pyrimidinecarboxamide, N-[(2,4-difluorophenyl)methyl]-2-[(1-methylpropyl)amino]-4-(1-phenylcyclopentyl)- | 0.062 | 2 | 100 | 465.3 |
| 121 | 5-pyrimidinecarboxamide, 2-(cyclopentylamino)-N-[(2,4-difluorophenyl)methyl]-4-(1-phenylcyclopentyl)- | 0.024 | 2.6 | 85 | 477.4 |
| 122 | 5-pyrimidinecarboxamide, 2-(cyclopropylamino)-N-[[3-fluoro-5-(trifluoromethyl)phenyl]methyl]-4-(1-phenylcyclopentyl)- | 0.010 | 2.6 | 100 | 499.3 |
| 123 | 5-pyrimidinecarboxamide, N-[[3-fluoro-5-(trifluoromethyl)phenyl]methyl]-2-[(4-methylcyclohexyl)amino]-4-(1-phenylcyclopentyl)- | 0.010 | 2.8 | 85 | 555.4 |
| 124 | 5-pyrimidinecarboxamide, N-[[3-fluoro-5-(trifluoromethyl)phenyl]methyl]-4-(1-phenylcyclopentyl)-2-(1-pyrrolidinyl)- | 0.240 | 2.7 | 100 | 513.3 |
| 125 | 5-pyrimidinecarboxamide, N-[[3-fluoro-5-(trifluoromethyl)phenyl]methyl]-2-(4-methyl-1-piperazinyl)-4-(1-phenylcyclopentyl)- | 0.375 | 1.7 | 100 | 542.4 |
| 126 | 5-pyrimidinecarboxamide, N-[[3-fluoro-5-(trifluoromethyl)phenyl]methyl]-2-(3-methyl-1-piperidinyl)-4-(1-phenylcyclopentyl)- | 0.319 | 2.2 | 91 | 541.4 |
| 127 | 5-pyrimidinecarboxamide, N-[[3-fluoro-5-(trifluoromethyl)phenyl]methyl]-2-(4-methyl-1-piperidinyl)-4-(1-phenylcylopentyl)- | 0.010 | 2.2 | 92 | 541.4 |
| 128 | 5-pyrimidinecarboxamide, N-[[3-fluoro-5-(trifluoromethyl)phenyl]methyl]-2-[(1-methylpropyl)amino]-4-(1-phenylcyclopentyl)- | 0.010 | 2.1 | 88 | 515.3 |
| 129 | 5-pyrimidinecarboxamide, 2-[[2-(dimethylamino)ethyl]amino]-N-[[3-fluoro-5-(trifluoromethyl)phenyl]methyl]-4-(1-phenylcyclopentyl)- | 0.020 | 2.2 | 100 | 530.4 |
| 130 | 5-pyrimidinecarboxamide, 2-(cyclopentylamino)-N-[[3-fluoro-5-(trifluoromethyl)phenyl]methyl]-4-(1-phenylcyclopentyl)- | 0.875 | 2.6 | 90 | 527.4 |
| 131 | 5-pyrimidinecarboxamide, N-[1-(4-fluorophenyl)ethyl]-2-[(4-methylcyclohexyl)amino]-4-(1-phenylcyclopentyl)- | 0.158 | 2.6 | 74 | 501.4 |

TABLE 4-continued

| Example no. | Compound Name | hQ23 EC$_{50}$ (uM) | Ret. time (min) | % Purity | e/z M + 1 |
|---|---|---|---|---|---|
| 132 | 5-pyrimidinecarboxamide, N-[1-(4-fluorophenyl)ethyl]-4-(1-phenylcyclopentyl)-2-(1-pyrrolidinyl)- | 0.195 | 2.6 | 97 | 459.4 |
| 133 | 5-pyrimidinecarboxamide, N-[1-(4-fluorophenyl)ethyl]-2-(4-methyl-1-piperazinyl)-4-(1-phenylcyclopentyl)- | 0.442 | 1.5 | 74 | 488.4 |
| 134 | 5-pyrimidinecarboxamide, N-[1-(4-fluorophenyl)ethyl]-2-(4-methyl-1-piperidinyl)-4-(1-phenylcyclopentyl)- | 0.098 | 2.1 | 75 | 487.4 |
| 135 | 5-pyrimidinecarboxamide, N-[1-(4-fluorophenyl)ethyl]-2-[(1-methylpropyl)amino]-4-(1-phenylcyclopentyl)- | 0.029 | 2 | 100 | 461.4 |
| 136 | 5-pyrimidinecarboxamide, 2-(cyclopentylamino)-N-[1-(4-fluorophenyl)ethyl]-4-(1-phenylcyclopentyl)- | 0.413 | 2.6 | 91 | 473.4 |
| 137 | 5-pyrimidinecarboxamide, 2-[(4-methylcyclohexyl)amino]-4-(1-phenylcyclopentyl)-N-[[4-(trifluoromethyl)phenyl]methyl]- | 0.964 | 2.7 | 91 | 537.4 |
| 138 | 5-pyrimidinecarboxamide, 2-(4-methyl-1-piperidinyl)-4-(1-phenylcyclopentyl)-N-[[4-(trifluoromethyl)phenyl]methyl]- | 0.010 | 2.2 | 92 | 523.4 |
| 139 | 5-pyrimidinecarboxamide, 4-[1-(4-chlorophenyl)cyclopentyl]-N-methyl-2-(4-methyl-1-piperazinyl)-N-(phenylmethyl)- | 0.070 | 2.2 | 94 | 504.4 |
| 140 | 5-pyrimidinecarboxamide, 4-[1-(4-chlorophenyl)cyclopentyl]-N-methyl-2-(4-methyl-1-piperidinyl)-N-(phenylmethyl)- | 0.246 | 2.3 | 96 | 503.4 |
| 141 | 5-pyrimidinecarboxamide, 4-[1-(4-chlorophenyl)cyclopentyl]-2-(cyclopentylamino)-N-methyl-N-(phenylmethyl)- | 0.183 | 2.8 | 95 | 489.3 |
| 142 | isoquinoline, 2-[[4-[1-(4-chlorophenyl)cyclopentyl]-2-(cyclopentylamino)-5-pyrimidinyl]carbonyl]-1,2,3,4-tetrahydro- | 0.535 | 2.8 | 94 | 501.4 |
| 143 | 5-pyrimidinecarboxamide, 4-[1-(4-chlorophenyl)cyclopentyl]-N-cyclohexyl-N-ethyl-2-[(1-methylpropyl)amino]- | 0.880 | 2.2 | 100 | 483.4 |
| 144 | piperidine, 1-[[4-[1-(4-chlorophenyl)cyclopentyl]-2-(cyclopropylamino)-5-pyrimidinyl]carbonyl]-3-methyl- | 0.884 | 2.6 | 96 | 439.3 |
| 145 | 5-pyrimidinecarboxamide, 4-[1-(4-chlorophenyl)cyclopentyl]-2-(cyclopropylamino)-N-methyl-N-(2-phenylethyl)- | 0.895 | 2.6 | 100 | 475.4 |
| 146 | 5-pyrimidinecarboxamide, 4-[1-(4-chlorophenyl)cyclopentyl]-N-methyl-2-[(4-methylcyclohexyl)amino]-N-(2-phenylethyl)- | 0.664 | 2.8 | 88 | 531.4 |
| 147 | 5-pyrimidinecarboxamide, 4-[1-(4-chlorophenyl)cyclopentyl]-N- | 0.169 | 2.7 | 90 | 489.4 |

TABLE 4-continued

| Example no. | Compound Name | hQ23 EC$_{50}$ (uM) | Ret. time (min) | % Purity | e/z M + 1 |
|---|---|---|---|---|---|
| 148 | methyl-N-(2-phenylethyl)-2-(1-pyrrolidinyl)-5-pyrimidinecarboxamide, 4-[1-(4-chlorophenyl)cyclopentyl]-2-(cyclopentylamino)-N-methyl-N-(2-phenylethyl)- | 0.597 | 2.8 | 92 | 503.4 |
| 149 | 5-pyrimidinecarboxamide, 4-[1-(4-chlorophenyl)cyclopentyl]-2-(cyclopentylamino)-N-ethyl-N-(phenylmethyl)- | 0.525 | 2.8 | 90 | 503.4 |
| 150 | 5-pyrimidinecarboxamide, N-(1,3-benzodioxol-5-ylmethyl)-4-[1-(4-chlorophenyl)cyclopentyl]-2-(cyclopropylamino)- | 0.717 | 2.5 | 76 | 491.3 |
| 151 | 5-pyrimidinecarboxamide, N-(1,3-benzodioxol-5-ylmethyl)-4-[1-(4-chlorophenyl)cyclopentyl]-2-[(4-methylcyclohexyl)amino]- | 0.119 | 2.7 | 73 | 547.4 |
| 152 | 5-pyrimidinecarboxamide, N-(1,3-benzodioxol-5-ylmethyl)-4-[1-(4-chlorophenyl)cyclopentyl]-2-(1-pyrrolidinyl)- | 0.107 | 2.6 | 88 | 505.3 |
| 153 | 5-pyrimidinecarboxamide, N-(1,3-benzodioxol-5-ylmethyl)-4-[1-(4-chlorophenyl)cyclopentyl]-2-(3-methyl-1-piperidinyl)- | 0.010 | 2.2 | 77 | 533.4 |
| 154 | 5-pyrimidinecarboxamide, N-(1,3-benzodioxol-5-ylmethyl)-4-[1-(4-chlorophenyl)cyclopentyl]-2-(4-methyl-1-piperidinyl)- | 0.010 | 2.2 | 73 | 533.3 |
| 155 | 5-pyrimidinecarboxamide, N-(1,3-benzodioxol-5-ylmethyl)-4-[1-(4-chlorophenyl)cyclopentyl]-2-[(1-methylpropyl)amino]- | 0.337 | 2 | 83 | 507.3 |
| 156 | 5-pyrimidinecarboxamide, N-(1,3-benzodioxol-5-ylmethyl)-4-[1-(4-chlorophenyl)cyclopentyl]-2-(cyclopentylamino)- | 0.070 | 2.6 | 77 | 519.3 |
| 157 | 5-pyrimidinecarboxamide, 4-[1-(4-chlorophenyl)cyclopentyl]-2-(cyclopropylamino)-N-[1-(1-naphthalenyl)ethyl]- | 0.195 | 2.7 | 90 | 511.3 |
| 158 | 5-pyrimidinecarboxamide, 4-[1-(4-chlorophenyl)cyclopentyl]-N-[1-(1-naphthalenyl)ethyl]-2-(1-pyrrolidinyl)- | 0.040 | 2.8 | 94 | 525.4 |
| 159 | 5-pyrimidinecarboxamide, 4-[1-(4-chlorophenyl)cyclopentyl]-2-(4-methyl-1-piperazinyl)-N-[1-(1-naphthalenyl)ethyl]- | 0.643 | 1.8 | 96 | 554.4 |
| 160 | 5-pyrimidinecarboxamide, 4-[1-(4-chlorophenyl)cyclopentyl]-2-(3-methyl-1-piperidinyl)-N-[1-(1-naphthalenyl)ethyl]- | 0.030 | 2.3 | 96 | 553.4 |
| 161 | 5-pyrimidinecarboxamide, 4-[1-(4-chlorophenyl)cyclopentyl]-2-(4-methyl-1-piperidinyl)-N-[1-(1-naphthalenyl)ethyl]- | 0.010 | 2.3 | 94 | 553.4 |
| 162 | 5-pyrimidinecarboxamide, 4-[1-(4-chlorophenyl)cyclopentyl]-2- | 0.113 | 2.2 | 86 | 527.4 |

TABLE 4-continued

| Example no. | Compound Name | hQ23 EC$_{50}$ (uM) | Ret. time (min) | % Purity | e/z M + 1 |
|---|---|---|---|---|---|
| 163 | [(1-methylpropyl)amino]-N-[1-(1-naphthalenyl)ethyl]- | 0.705 | 2.3 | 92 | 542.4 |
| 164 | 5-pyrimidinecarboxamide, 4-[1-(4-chlorophenyl)cyclopentyl]-2-[[2-(dimethylamino)ethyl]amino]-N-[1-(1-naphthalenyl)ethyl]- | 0.010 | 2.7 | 86 | 539.4 |
| 165 | 5-pyrimidinecarboxamide, 4-[1-(4-chlorophenyl)cyclopentyl]-2-(cyclopentylamino)-N-[1-(1-naphthalenyl)ethyl]- | 0.630 | 2.7 | 90 | 497.3 |
| 166 | 5-pyrimidinecarboxamide, 4-[1-(4-chlorophenyl)cyclopentyl]-2-(cyclopropylamino)-N-(1-naphthalenylmethyl)- | 0.016 | 2.8 | 84 | 553.4 |
| 167 | 5-pyrimidinecarboxamide, 4-[1-(4-chlorophenyl)cyclopentyl]-2-[(4-methylcyclohexyl)amino]-N-(1-naphthalenylmethyl)- | 0.142 | 2.8 | 94 | 511.3 |
| 168 | 5-pyrimidinecarboxamide, 4-[1-(4-chlorophenyl)cyclopentyl]-N-(1-naphthalenylmethyl)-2-(1-pyrrolidinyl)- | 0.497 | 1.8 | 97 | 540.4 |
| 169 | 5-pyrimidinecarboxamide, 4-[1-(4-chlorophenyl)cyclopentyl]-2-(4-methyl-1-piperazinyl)-N-(1-naphthalenylmethyl)- | 0.010 | 2.3 | 92 | 539.4 |
| 170 | 5-pyrimidinecarboxamide, 4-[1-(4-chlorophenyl)cyclopentyl]-2-(3-methyl-1-piperidinyl)-N-(1-naphthalenylmethyl)- | 0.010 | 2.3 | 91 | 539.4 |
| 171 | 5-pyrimidinecarboxamide, 4-[1-(4-chlorophenyl)cyclopentyl]-2-(4-methyl-1-piperidinyl)-N-(1-naphthalenylmethyl)- | 0.158 | 2.2 | 78 | 513.3 |
| 172 | 5-pyrimidinecarboxamide, 4-[1-(4-chlorophenyl)cyclopentyl]-2-[(1-methylpropyl)amino]-N-(1-naphthalenylmethyl)- | 0.373 | 2.8 | 86 | 525.3 |
| 173 | 5-pyrimidinecarboxamide, 4-[1-(4-chlorophenyl)cyclopentyl]-2-(cyclopentylamino)-N-(1-naphthalenylmethyl)- | 0.820 | 1.8 | 96 | 558.3 |
| 174 | 5-pyrimidinecarboxamide, 4-[1-(4-chlorophenyl)cyclopentyl]-N-[(3,4-dichlorophenyl)methyl]-2-(4-methyl-1-piperazinyl)- | 0.010 | 2.3 | 95 | 557.3 |
| 175 | 5-pyrimidinecarboxamide, 4-[1-(4-chlorophenyl)cyclopentyl]-N-[(3,4-dichlorophenyl)methyl]-2-(3-methyl-1-piperidinyl)- | 0.010 | 2.3 | 93 | 557.3 |
| 176 | 5-pyrimidinecarboxamide, 4-[1-(4-chlorophenyl)cyclopentyl]-N-[(3,4-dichlorophenyl)methyl]-2-(4-methyl-1-piperidinyl)- | 0.196 | 2.6 | 94 | 515.2 |
| 177 | 5-pyrimidinecarboxamide, 4-[1-(4-chlorophenyl)cyclopentyl]-2-(cyclopropylamino)-N-[(2,4-dichlorophenyl)methyl]- | 0.055 | 2.9 | 82 | 571.3 |
| | 5-pyrimidinecarboxamide, 4-[1-(4-chlorophenyl)cyclopentyl]-N- | | | | |

TABLE 4-continued

| Example no. | Compound Name | hQ23 EC$_{50}$ (uM) | Ret. time (min) | % Purity | e/z M + 1 |
|---|---|---|---|---|---|
| 178 | 5-pyrimidinecarboxamide, 4-[1-(4-chlorophenyl)cyclopentyl]-N-[(2,4-dichlorophenyl)methyl]-2-[(4-methylcyclohexyl)amino]- | 0.074 | 2.7 | 92 | 529.2 |
| 179 | 5-pyrimidinecarboxamide, 4-[1-(4-chlorophenyl)cyclopentyl]-N-[(2,4-dichlorophenyl)methyl]-2-(1-pyrrolidinyl)- | 0.535 | 1.8 | 96 | 558.3 |
| 180 | 5-pyrimidinecarboxamide, 4-[1-(4-chlorophenyl)cyclopentyl]-N-[(2,4-dichlorophenyl)methyl]-2-(4-methyl-1-piperazinyl)- | 0.010 | 2.3 | 84 | 557.3 |
| 181 | 5-pyrimidinecarboxamide, 4-[1-(4-chlorophenyl)cyclopentyl]-N-[(2,4-dichlorophenyl)methyl]-2-(3-methyl-1-piperidinyl)- | 0.010 | 2.3 | 94 | 557.3 |
| 182 | 5-pyrimidinecarboxamide, 4-[1-(4-chlorophenyl)cyclopentyl]-N-[(2,4-dichlorophenyl)methyl]-2-(4-methyl-1-piperidinyl)- | 0.067 | 1.8 | 100 | 586.3 |
| 183 | 5-pyrimidinecarboxamide, 4-[1-(4-chlorophenyl)cyclopentyl]-N-[(2,4-dichlorophenyl)methyl]-2-[methyl(1-methyl-4-piperidinyl)amino]- | 0.010 | 2.2 | 93 | 531.3 |
| 184 | 5-pyrimidinecarboxamide, 4-[1-(4-chlorophenyl)cyclopentyl]-N-[(2,4-dichlorophenyl)methyl]-2-[(1-methylpropyl)amino]- | 0.709 | 2.4 | 94 | 546.3 |
| 185 | 5-pyrimidinecarboxamide, 4-[1-(4-chlorophenyl)cyclopentyl]-N-[(2,4-dichlorophenyl)methyl]-2-[[2-(dimethylamino)ethyl]amino]- | 0.010 | 2.8 | 91 | 543.3 |
| 186 | 5-pyrimidinecarboxamide, 4-[1-(4-chlorophenyl)cyclopentyl]-2-(cyclopentylamino)-N-[(2,4-dichlorophenyl)methyl]- | 0.128 | 2.7 | 84 | 539.4 |
| 187 | 5-pyrimidinecarboxamide, 4-[1-(4-chlorophenyl)cyclopentyl]-N-[(2,4-difluorophenyl)methyl]-2-[(4-methylcyclohexyl)amino]- | 0.095 | 2.2 | 92 | 525.3 |
| 188 | 5-pyrimidinecarboxamide, 4-[1-(4-chlorophenyl)cyclopentyl]-N-[(2,4-difluorophenyl)methyl]-2-(3-methyl-1-piperidinyl)- | 0.016 | 2.2 | 91 | 525.3 |
| 189 | 5-pyrimidinecarboxamide, 4-[1-(4-chlorophenyl)cyclopentyl]-N-[(2,4-difluorophenyl)methyl]-2-(4-methyl-1-piperidinyl)- | 0.340 | 2.7 | 92 | 511.3 |
| 190 | 5-pyrimidinecarboxamide, 4-[1-(4-chlorophenyl)cyclopentyl]-2-(cyclopentylamino)-N-[(2,4-difluorophenyl)methyl]- | 0.163 | 2.8 | 88 | 589.4 |
| 191 | 5-pyrimidinecarboxamide, 4-[1-(4-chlorophenyl)cyclopentyl]-N-[[3-fluoro-5-(trifluoromethyl)phenyl]methyl]-2-[(4-methylcyclohexyl)amino]- | 0.032 | 2.7 | 93 | 547.3 |

TABLE 4-continued

| Example no. | Compound Name | hQ23 EC$_{50}$ (uM) | Ret. time (min) | % Purity | e/z M + 1 |
|---|---|---|---|---|---|
| 192 | [[3-fluoro-5-(trifluoromethyl)phenyl]methyl]-2-(1-pyrrolidinyl)-5-pyrimidinecarboxamide, 4-[1-(4-chlorophenyl)cyclopentyl]-N-[[3-fluoro-5-(trifluoromethyl)phenyl]methyl]-2-(3-methyl-1-piperidinyl)- | 0.010 | 2.3 | 93 | 575.4 |
| 193 | 5-pyrimidinecarboxamide, 4-[1-(4-chlorophenyl)cyclopentyl]-N-[[3-fluoro-5-(trifluoromethyl)phenyl]methyl]-2-(4-methyl-1-piperidinyl)- | 0.012 | 2.3 | 88 | 575.4 |
| 194 | 5-pyrimidinecarboxamide, 4-[1-(4-chlorophenyl)cyclopentyl]-N-[[3-fluoro-5-(trifluoromethyl)phenyl]methyl]-2-[methyl(1-methyl-4-piperidinyl)amino]- | 0.130 | 1.8 | 100 | 604.4 |
| 195 | 5-pyrimidinecarboxamide, 4-[1-(4-chlorophenyl)cyclopentyl]-2-[[2-(dimethylamino)ethyl]amino]-N-[[3-fluoro-5-(trifluoromethyl)phenyl]methyl]- | 0.634 | 2.4 | 95 | 564.3 |
| 196 | 5-pyrimidinecarboxamide, 4-[1-(4-chlorophenyl)cyclopentyl]-2-(cyclopentylamino)-N-[[3-fluoro-5-(trifluoromethyl)phenyl]methyl]- | 0.091 | 2.8 | 91 | 561.3 |
| 197 | 5-pyrimidinecarboxamide, 4-[1-(4-chlorophenyl)cyclopentyl]-N-[1-(4-fluorophenyl)ethyl]-2-[(4-methylcyclohexyl)amino]- | 0.233 | 2.7 | 89 | 535.4 |
| 198 | 5-pyrimidinecarboxamide, 4-[1-(4-chlorophenyl)cyclopentyl]-N-[1-(4-fluorophenyl)ethyl]-2-(3-methyl-1-piperidinyl)- | 0.124 | 2.2 | 93 | 521.4 |
| 199 | 5-pyrimidinecarboxamide, 4-[1-(4-chlorophenyl)cyclopentyl]-N-[1-(4-fluorophenyl)ethyl]-2-(4-methyl-1-piperidinyl)- | 0.061 | 2.2 | 93 | 521.3 |
| 200 | 5-pyrimidinecarboxamide, 4-[1-(4-chlorophenyl)cyclopentyl]-N-[1-(4-fluorophenyl)ethyl]-2-[(1-methylpropyl)amino]- | 0.911 | 2.1 | 100 | 495.3 |
| 201 | 5-pyrimidinecarboxamide, 4-[1-(4-chlorophenyl)cyclopentyl]-2-(cyclopentylamino)-N-[1-(4-fluorophenyl)ethyl]- | 0.592 | 2.7 | 95 | 507.3 |
| 202 | 5-pyrimidinecarboxamide, 4-[1-(4-chlorophenyl)cyclopentyl]-2-(4-methyl-1-piperazinyl)-N-[[4-(trifluoromethyl)phenyl]methyl]- | 0.879 | 1.7 | 97 | 558.4 |
| 203 | 5-pyrimidinecarboxamide, 4-[1-(4-chlorophenyl)cyclopentyl]-2-(4-methyl-1-piperidinyl)-N-[[4-(trifluoromethyl)phenyl]methyl]- | 0.032 | 2.3 | 100 | 557.3 |
| 204 | 5-pyrimidinecarboxamide, 4-[1-(4-chlorophenyl)cyclopentyl]-2-[methyl(1-methyl-4- | 0.400 | 1.8 | 100 | 586.4 |

TABLE 4-continued

| Example no. | Compound Name | hQ23 EC$_{50}$ (uM) | Ret. time (min) | % Purity | e/z M + 1 |
|---|---|---|---|---|---|
| 205 | piperidinyl)amino]-N-[[4-(trifluoromethyl)phenyl]methyl]- 5-pyrimidinecarboxamide, 4-[1-(4-fluorophenyl)cyclopentyl]-N-methyl-2-(3-methyl-1-piperidinyl))-N-(phenylmethyl)- | 0.116 | 2.2 | 94 | 487.4 |
| 206 | 5-pyrimidinecarboxamide, 4-[1-(4-fluorophenyl)cyclopentyl]-N-methyl-2-(4-methyl-1-piperidinyl))-N-(phenylmethyl)- | 0.261 | 2.2 | 100 | 487.4 |
| 207 | 5-pyrimidinecarboxamide, N-cyclohexyl-4-[1-(4-fluorophenyl)cyclopentyl]-N-methyl-2-[(4-methylcyclohexyl)amino]- | 0.873 | 2.6 | 100 | 493.5 |
| 208 | 5-pyrimidinecarboxamide, N-cyclohexyl-4-[1-(4-fluorophenyl)cyclopentyl]-N-methyl-2-(4-methyl-1-piperidinyl)- | 0.558 | 2.3 | 94 | 479.4 |
| 209 | 5-pyrimidinecarboxamide, N-cyclohexyl-2-(cyclopentylamino)-4-[1-(4-fluorophenyl)cyclopentyl]-N-methyl- | 0.702 | 2.7 | 92 | 465.4 |
| 210 | isoquinoline, 2-[[4-[1-(4-fluorophenyl)cyclopentyl]-2-[(4-methylcyclohexyl)amino]-5-pyrimidinyl]carbonyl]-1,2,3,4-tetrahydro- | 0.375 | 2.8 | 72 | 513.4 |
| 211 | isoquinoline, 2-[[4-[1-(4-fluorophenyl)cyclopentyl]-2-(3-methyl-1-piperidinyl)-5-pyrimidinyl]carbonyl]-1,2,3,4-tetrahydro- | 0.272 | 2.3 | 95 | 499.4 |
| 212 | isoquinoline, 2-[[4-[1-(4-fluorophenyl)cyclopentyl]-2-(4-methyl-1-piperidinyl)-5-pyrimidinyl]carbonyl]-1,2,3,4-tetrahydro- | 0.237 | 2.3 | 93 | 499.4 |
| 213 | 5-pyrimidinecarboxamide, N-cyclohexyl-N-ethyl-4-[1-(4-fluorophenyl)cyclopentyl]-2-(1-pyrrolidinyl)- | 0.680 | 2.7 | 74 | 465.4 |
| 214 | 5-pyrimidinecarboxamide, N-cyclohexyl-N-ethyl-4-[1-(4-fluorophenyl)cyclopentyl]-2-(3-methyl-1-piperidinyl)- | 0.575 | 2.3 | 76 | 493.5 |
| 215 | 5-pyrimidinecarboxamide, N-cyclohexyl-N-ethyl-4-[1-(4-fluorophenyl)cyclopentyl]-2-(4-methyl-1-piperidinyl)- | 0.922 | 2.3 | 92 | 493.5 |
| 216 | 5-pyrimidinecarboxamide, N-cyclohexyl-N-ethyl-4-[1-(4-fluorophenyl)cyclopentyl]-2-[(1-methylpropyl)amino]- | 0.821 | 2.2 | 100 | 467.4 |
| 217 | 5-pyrimidinecarboxamide, N-cyclohexyl-2-(cyclopentylamino)-N-ethyl-4-[1-(4-fluorophenyl)cyclopentyl]- | 0.482 | 2.8 | 84 | 479.4 |
| 218 | piperidine, 1-[[4-[1-(4-fluorophenyl)cyclopentyl]-2-(4-methyl-1-piperidinyl)-5-pyrimidinyl]carbonyl]-3-methyl- | 0.866 | 2.2 | 87 | 465.4 |
| 219 | 5-pyrimidinecarboxamide, 4-[1-(4-fluorophenyl)cyclopentyl]-N-methyl-2-[(4-methylcyclohexyl)amino]-N-(2-phenylethyl)- | 0.334 | 2.7 | 74 | 515.4 |

TABLE 4-continued

| Example no. | Compound Name | hQ23 EC$_{50}$ (uM) | Ret. time (min) | % Purity | e/z M + 1 |
|---|---|---|---|---|---|
| 220 | 5-pyrimidinecarboxamide, 4-[1-(4-fluorophenyl)cyclopentyl]-N-methyl-N-(2-phenylethyl)-2-(1-pyrrolidinyl)- | 0.169 | 2.7 | 91 | 473.4 |
| 221 | 5-pyrimidinecarboxamide, 4-[1-(4-fluorophenyl)cyclopentyl]-N-methyl-2-(3-methyl-1-piperidinyl)-N-(2-phenylethyl)- | 0.356 | 2.2 | 92 | 501.4 |
| 222 | 5-pyrimidinecarboxamide, 4-[1-(4-fluorophenyl)cyclopentyl]-N-methyl-2-(4-methyl-1-piperidinyl)-N-(2-phenylethyl)- | 0.273 | 2.2 | 94 | 501.4 |
| 223 | 5-pyrimidinecarboxamide, 4-[1-(4-fluorophenyl)cyclopentyl]-N-methyl-2-[(1-methylpropyl)amino]-N-(2-phenylethyl)- | 0.675 | 2.1 | 100 | 475.4 |
| 224 | 5-pyrimidinecarboxamide, 4-[1-(4-fluorophenyl)cyclopentyl]-N,N-bis(1-methylethyl)-2-(3-methyl-1-piperidinyl)- | 0.039 | 2.2 | 88 | 465.4 |
| 225 | 5-pyrimidinecarboxamide, N-ethyl-4-[1-(4-fluorophenyl)cyclopentyl]-N-methyl-2-[(4-methylcyclohexyl)amino]- | 0.452 | 2.6 | 71 | 439.4 |
| 226 | 5-pyrimidinecarboxamide, N-ethyl-4-[1-(4-fluorophenyl)cyclopentyl]-N-methyl-2-(3-methyl-1-piperidinyl)- | 0.505 | 2.1 | 87 | 425.4 |
| 227 | 5-pyrimidinecarboxamide, N-ethyl-4-[1-(4-fluorophenyl)cyclopentyl]-N-methyl-2-(4-methyl-1-piperidinyl)- | 0.882 | 2.1 | 81 | 425.4 |
| 228 | 5-pyrimidinecarboxamide, N-ethyl-4-[1-(4-fluorophenyl)cyclopentyl]-2-[(4-methylcyclohexyl)amino]-N-(phenylmethyl)- | 0.637 | 2.8 | 86 | 515.4 |
| 229 | 5-pyrimidinecarboxamide, N-ethyl-4-[1-(4-fluorophenyl)cyclopentyl]-2-(3-methyl-1-piperidinyl)-N-(phenylmethyl)- | 0.369 | 2.3 | 93 | 501.4 |
| 230 | 5-pyrimidinecarboxamide, N-ethyl-4-[1-(4-fluorophenyl)cyclopentyl]-2-(4-methyl-1-piperidinyl)-N-(phenylmethyl)- | 0.168 | 2.3 | 94 | 501.4 |
| 231 | 5-pyrimidinecarboxamide, N-ethyl-4-[1-(4-fluorophenyl)cyclopentyl]-2-[(1-methylpropyl)amino]-N-(phenylmethyl)- | 0.786 | 2.1 | 100 | 475.4 |
| 232 | 5-pyrimidinecarboxamide, 2-(cyclopentylamino)-N-ethyl-4-[1-(4-fluorophenyl)cyclopentyl]-N-(phenylmethyl)- | 0.460 | 2.7 | 83 | 487.4 |
| 233 | 5-pyrimidinecarboxamide, N-(1,3-benzodioxol-5-ylmethyl)-2-(cyclopropylamino)-4-[1-(4-fluorophenyl)cyclopentyl]- | 0.436 | 2.4 | 100 | 475.3 |
| 234 | 5-pyrimidinecarboxamide, N-(1,3-benzodioxol-5-ylmethyl)-4-[1-(4- | 0.235 | 2.6 | 78 | 531.4 |

TABLE 4-continued

| Example no. | Compound Name | hQ23 EC$_{50}$ (uM) | Ret. time (min) | % Purity | e/z M + 1 |
|---|---|---|---|---|---|
| 235 | fluorophenyl)cyclopentyl]-2-[(4-methylcyclohexyl)amino]- | 0.214 | 2.5 | 89 | 489.3 |
| 236 | 5-pyrimidinecarboxamide, N-(1,3-benzodioxol-5-ylmethyl)-4-[1-(4-fluorophenyl)cyclopentyl]-2-(1-pyrrolidinyl)- | 0.039 | 2.1 | 79 | 517.4 |
| 237 | 5-pyrimidinecarboxamide, N-(1,3-benzodioxol-5-ylmethyl)-4-[1-(4-fluorophenyl)cyclopentyl]-2-(3-methyl-1-piperidinyl)- | 0.540 | 2.1 | 82 | 517.4 |
| 238 | 5-pyrimidinecarboxamide, N-(1,3-benzodioxol-5-ylmethyl)-4-[1-(4-fluorophenyl)cyclopentyl]-2-(4-methyl-1-piperidinyl)- | 0.344 | 1.9 | 81 | 491.4 |
| 239 | 5-pyrimidinecarboxamide, N-(1,3-benzodioxol-5-ylmethyl)-4-[1-(4-fluorophenyl)cyclopentyl]-2-[(1-methylpropyl)amino]- | 0.792 | 2.1 | 83 | 506.3 |
| 240 | 5-pyrimidinecarboxamide, 2-(cyclopropylamino)-4-[1-(4-fluorophenyl)cyclopentyl]-N-[2-[[2-(dimethylamino)ethyl]amino]-4-[1-(4-fluorophenyl)cyclopentyl]- | 0.507 | 2.6 | 93 | 495.4 |
| 241 | 5-pyrimidinecarboxamide, 4-[1-(4-fluorophenyl)cyclopentyl]-2-[(4-methylcyclohexyl)amino]-N-[1-(1-naphthalenyl)ethyl]- | 0.010 | 2.7 | 73 | 551.4 |
| 242 | 5-pyrimidinecarboxamide, 4-[1-(4-fluorophenyl)cyclopentyl]-N-[1-(1-naphthalenyl)ethyl]-2-(1-pyrrolidinyl)- | 0.034 | 2.7 | 95 | 509.4 |
| 243 | 5-pyrimidinecarboxamide, 4-[1-(4-fluorophenyl)cyclopentyl]-2-(4-methyl-1-piperazinyl)-N-[1-(1-naphthalenyl)ethyl]- | 0.852 | 1.7 | 96 | 538.4 |
| 244 | 5-pyrimidinecarboxamide, 4-[1-(4-fluorophenyl)cyclopentyl]-2-(3-methyl-1-piperidinyl)-N-[1-(1-naphthalenyl)ethyl]- | 0.010 | 2.2 | 96 | 537.4 |
| 245 | 5-pyrimidinecarboxamide, 4-[1-(4-fluorophenyl)cyclopentyl]-2-(4-methyl-1-piperidinyl)-N-[1-(1-naphthalenyl)ethyl]- | 0.010 | 2.2 | 94 | 537.4 |
| 246 | 5-pyrimidinecarboxamide, 4-[1-(4-fluorophenyl)cyclopentyl]-2-[(1-methylpropyl)amino]-N-[1-(1-naphthalenyl)ethyl]- | 0.177 | 2.1 | 91 | 511.4 |
| 247 | 5-pyrimidinecarboxamide, 2-(cyclopentylamino)-4-[1-(4-fluorophenyl)cyclopentyl]-N-[1-(1-naphthalenyl)ethyl]- | 0.092 | 2.7 | 90 | 523.4 |
| 248 | 5-pyrimidinecarboxamide, 4-[1-(4-fluorophenyl)cyclopentyl]-2-[(4-methylcyclohexyl)amino]-N-(1-naphthalenylmethyl)- | 0.010 | 2.7 | 70 | 537.4 |
| 249 | 5-pyrimidinecarboxamide, 4-[1-(4-fluorophenyl)cyclopentyl]-N-(1-naphthalenylmethyl)-2-(1-pyrrolidinyl)- | 0.278 | 2.7 | 96 | 495.4 |
| 250 | 5-pyrimidinecarboxamide, 4-[1-(4- | 0.010 | 2.2 | 100 | 523.4 |

TABLE 4-continued

| Example no. | Compound Name | hQ23 EC$_{50}$ (uM) | Ret. time (min) | % Purity | e/z M + 1 |
|---|---|---|---|---|---|
|  | ...fluorophenyl)cyclopentyl]-2-(3-methyl-1-piperidinyl)-N-(1-naphthalenylmethyl)- |  |  |  |  |
| 251 | 5-pyrimidinecarboxamide, 4-[1-(4-fluorophenyl)cyclopentyl]-2-(4-methyl-1-piperidinyl)-N-(1-naphthalenylmethyl)- | 0.015 | 2.2 | 92 | 523.4 |
| 252 | 5-pyrimidinecarboxamide, 4-[1-(4-fluorophenyl)cyclopentyl]-2-[(1-methylpropyl)amino]-N-(1-naphthalenylmethyl)- | 0.350 | 2.1 | 81 | 497.4 |
| 253 | 5-pyrimidinecarboxamide, 2-(cyclopentylamino)-4-[1-(4-fluorophenyl)cyclopentyl]-N-(1-naphthalenylmethyl)- | 0.183 | 2.7 | 87 | 509.4 |
| 254 | 5-pyrimidinecarboxamide, N-[(3,4-dichlorophenyl)methyl]-4-[1-(4-fluorophenyl)cyclopentyl]-2-(4-methyl-1-piperazinyl)- | 0.529 | 2.3 | 95 | 542.3 |
| 255 | 5-pyrimidinecarboxamide, N-[(3,4-dichlorophenyl)methyl]-4-[1-(4-fluorophenyl)cyclopentyl]-2-(3-methyl-1-piperidinyl)- | 0.010 | 2.2 | 92 | 541.3 |
| 256 | 5-pyrimidinecarboxamide, N-[(3,4-dichlorophenyl)methyl]-4-[1-(4-fluorophenyl)cyclopentyl]-2-(4-methyl-1-piperidinyl)- | 0.010 | 2.2 | 100 | 541.3 |
| 257 | 5-pyrimidinecarboxamide, N-[(3,4-dichlorophenyl)methyl]-2-[[2-(dimethylamino)ethyl]amino]-4-[1-(4-fluorophenyl)cyclopentyl]- | 0.904 | 2.3 | 81 | 530.3 |
| 258 | 5-pyrimidinecarboxamide, 2-(cyclopentylamino)-N-[(3,4-dichlorophenyl)methyl]-4-[1-(4-fluorophenyl)cyclopentyl]- | 0.091 | 2.7 | 92 | 527.3 |
| 259 | 5-pyrimidinecarboxamide, 2-(cyclopropylamino)-N-[(2,4-dichlorophenyl)methyl]-4-[1-(4-fluorophenyl)cyclopentyl]- | 0.869 | 2.6 | 95 | 499.3 |
| 260 | 5-pyrimidinecarboxamide, N-[(2,4-dichlorophenyl)methyl]-4-[1-(4-fluorophenyl)cyclopentyl]-2-[(4-methylcyclohexyl)amino]- | 0.010 | 2.8 | 92 | 555.3 |
| 261 | 5-pyrimidinecarboxamide, N-[(2,4-dichlorophenyl)methyl]-4-[1-(4-fluorophenyl)cyclopentyl]-2-(1-pyrrolidinyl)- | 0.028 | 2.7 | 93 | 513.3 |
| 262 | 5-pyrimidinecarboxamide, N-[(2,4-dichlorophenyl)methyl]-4-[1-(4-fluorophenyl)cyclopentyl]-2-(3-methyl-1-piperidinyl)- | 0.010 | 2.2 | 95 | 541.3 |
| 263 | 5-pyrimidinecarboxamide, N-[(2,4-dichlorophenyl)methyl]-4-[1-(4-fluorophenyl)cyclopentyl]-2-(4-methyl-1-piperidinyl)- | 0.017 | 2.2 | 94 | 541.3 |
| 264 | 5-pyrimidinecarboxamide, N-[(2,4-dichlorophenyl)methyl]-4-[1-(4-fluorophenyl)cyclopentyl]-2-[methyl(1-methyl-4-piperidinyl)amino]- | 0.282 | 2.3 | 100 | 570.4 |
| 265 | 5-pyrimidinecarboxamide, N-[(2,4-dichlorophenyl)methyl]-4-[1-(4- | 0.138 | 2.1 | 92 | 515.3 |

TABLE 4-continued

| Example no. | Compound Name | hQ23 EC$_{50}$ (uM) | Ret. time (min) | % Purity | e/z M + 1 |
|---|---|---|---|---|---|
| 266 | fluorophenyl)cyclopentyl]-2-[(1-methylpropyl)amino]-5-pyrimidinecarboxamide, 2-(cyclopentylamino)-N-[(2,4-dichlorophenyl)methyl]-4-[1-(4-fluorophenyl)cyclopentyl]- | 0.027 | 2.8 | 91 | 527.3 |
| 267 | 5-pyrimidinecarboxamide, N-[(2,4-difluorophenyl)methyl]-4-[1-(4-fluorophenyl)cyclopentyl]-2-[(4-methylcyclohexyl)amino]- | 0.048 | 2.7 | 89 | 523.4 |
| 268 | 5-pyrimidinecarboxamide, N-[(2,4-difluorophenyl)methyl]-4-[1-(4-fluorophenyl)cyclopentyl]-2-(4-methyl-1-piperazinyl)- | 0.634 | 1.6 | 80 | 510.4 |
| 269 | 5-pyrimidinecarboxamide, N-[(2,4-difluorophenyl)methyl]-4-[1-(4-fluorophenyl)cyclopentyl]-2-(3-methyl-1-piperidinyl)- | 0.056 | 2.1 | 91 | 509.4 |
| 270 | 5-pyrimidinecarboxamide, N-[(2,4-difluorophenyl)methyl]-4-[1-(4-fluorophenyl)cyclopentyl]-2-(4-methyl-1-piperidinyl)- | 0.142 | 2.1 | 83 | 509.4 |
| 271 | 5-pyrimidinecarboxamide, N-[(2,4-difluorophenyl)methyl]-4-[1-(4-fluorophenyl)cyclopentyl]-2-[methyl(1-methyl-4-piperidinyl)amino]- | 0.532 | 1.7 | 100 | 538.4 |
| 272 | 5-pyrimidinecarboxamide, N-[(2,4-difluorophenyl)methyl]-2-[[2-(dimethylamino)ethyl]amino]-4-[1-(4-fluorophenyl)cyclopentyl]- | 0.967 | 2.1 | 93 | 498.4 |
| 273 | 5-pyrimidinecarboxamide, 2-(cyclopentylamino)-N-[(2,4-difluorophenyl)methyl]-4-[1-(4-fluorophenyl)cyclopentyl]- | 0.115 | 2.6 | 81 | 495.4 |
| 274 | 5-pyrimidinecarboxamide, 4-[1-(4-fluorophenyl)cyclopentyl]-N-[[3-fluoro-5-(trifluoromethyl)phenyl]methyl]-2-[(4-methylcyclohexyl)amino]- | 0.029 | 2.7 | 85 | 573.4 |
| 275 | 5-pyrimidinecarboxamide, 4-[1-(4-fluorophenyl)cyclopentyl]-N-[[3-fluoro-5-(trifluoromethyl)phenyl]methyl]-2-(1-pyrrolidinyl)- | 0.024 | 2.7 | 100 | 531.3 |
| 276 | 5-pyrimidinecarboxamide, 4-[1-(4-fluorophenyl)cyclopentyl]-N-[[3-fluoro-5-(trifluoromethyl)phenyl]methyl]-2-(4-methyl-1-piperazinyl)- | 0.327 | 2.3 | 94 | 560.4 |
| 277 | 5-pyrimidinecarboxamide, 4-[1-(4-fluorophenyl)cyclopentyl]-N-[[3-fluoro-5-(trifluoromethyl)phenyl]methyl]-2-(3-methyl-1-piperidinyl)- | 0.022 | 2.2 | 92 | 559.4 |
| 278 | 5-pyrimidinecarboxamide, 4-[1-(4-fluorophenyl)cyclopentyl]-N-[[3-fluoro-5-(trifluoromethyl)phenyl]methyl]-2-(4-methyl-1-piperidinyl)- | 0.010 | 2.2 | 89 | 559.4 |
| 279 | 5-pyrimidinecarboxamide, 4-[1-(4-fluorophenyl)cyclopentyl]-N- | 0.055 | 2.1 | 100 | 533.3 |

TABLE 4-continued

| Example no. | Compound Name | hQ23 EC$_{50}$ (uM) | Ret. time (min) | % Purity | e/z M + 1 |
|---|---|---|---|---|---|
| 280 | [[3-fluoro-5-(trifluoromethyl)phenyl]methyl]-2-[(1-methylpropyl)amino]-5-pyrimidinecarboxamide, 2-(cyclopentylamino)-4-[1-(4-fluorophenyl)cyclopentyl]-N- | 0.060 | 2.7 | 92 | 545.3 |
| 281 | [[3-fluoro-5-(trifluoromethyl)phenyl]methyl]-5-pyrimidinecarboxamide, 4-[1-(4-fluorophenyl)cyclopentyl]-N-[1-(4-fluorophenyl)ethyl]-2-[(4-methylcyclohexyl)amino]- | 0.118 | 2.7 | 82 | 519.4 |
| 282 | 5-pyrimidinecarboxamide, 4-[1-(4-fluorophenyl)cyclopentyl]-N-[1-(4-fluorophenyl)ethyl]-2-(1-pyrrolidinyl)- | 0.594 | 2.6 | 100 | 477.4 |
| 283 | 5-pyrimidinecarboxamide, 4-[1-(4-fluorophenyl)cyclopentyl]-N-[1-(4-fluorophenyl)ethyl]-2-(4-methyl-1-piperazinyl)- | 0.752 | 1.6 | 78 | 506.4 |
| 284 | 5-pyrimidinecarboxamide, 4-[1-(4-fluorophenyl)cyclopentyl]-N-[1-(4-fluorophenyl)ethyl]-2-(3-methyl-1-piperidinyl)- | 0.078 | 2.1 | 82 | 505.4 |
| 285 | 5-pyrimidinecarboxamide, 4-[1-(4-fluorophenyl)cyclopentyl]-N-[1-(4-fluorophenyl)ethyl]-2-(4-methyl-1-piperidinyl)- | 0.095 | 2.1 | 78 | 505.4 |
| 286 | 5-pyrimidinecarboxamide, 4-[1-(4-fluorophenyl)cyclopentyl]-N-[1-(4-fluorophenyl)ethyl]-2-[(1-methylpropyl)amino]- | 0.852 | 2 | 100 | 479.4 |
| 287 | 5-pyrimidinecarboxamide, 2-(cyclopentylamino)-4-[1-(4-fluorophenyl)cyclopentyl]-N-[1-(4-fluorophenyl)ethyl]- | 0.573 | 2.6 | 93 | 491.3 |
| 288 | 5-pyrimidinecarboxamide, 4-[1-(4-fluorophenyl)cyclopentyl]-2-(4-methyl-1-piperidinyl)-N-[[4-(trifluoromethyl)phenyl]methyl]- | 0.075 | 2.2 | 85 | 541.4 |

EXAMPLE 299

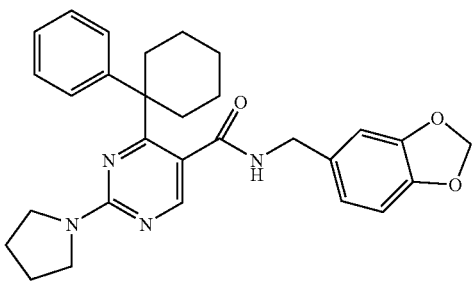

N-(1,3-benzodioxol-5-ylmethyl)-4-[1-phenylcyclohexyl]-2-(1-pyrrolidinyl)-5-pyrimidinecarboxamide. Prepared following procedure B. Product isolated as a yellow oil (0.019 g, 6% yield). $^1$H NMR (CDCl$_3$, 300 MHz): δ 8.24 (s, 1H), 7.26–7.16 (m, 4H), 7.11 (t, 1H, J=8.1 Hz), 6.68 (d, 1H, J=6.5 Hz), 6.51–6.48 (m, 2H), 5.92 (s, 2H), 4.71 (t, 1H, J=5.3 Hz), 4.03 (d, 2H, J=5.6 Hz), 3.65–3.60 (m, 4H), 2.63–2.58 (m, 2H), 2.05–2.00 (m, 4H), 1.96–1.83 (m, 2H), 1.59–1.52 (m, 6H); LRMS: 485.3 [M+H]$^+$; LCMS retention time: 1.95 min.

We claim:

1. A compound of Formula I

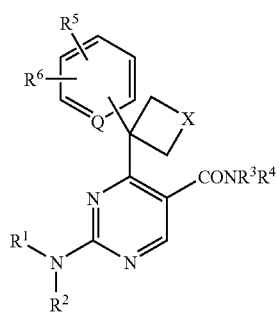

I wherein:

Q is CH or N;

X is a bond, methylene, ethylene, or propylene;

$R^1$ is hydrogen, $C_{1-6}$alkyl, $C_{3-7}$cycloalkyl, $CH_2Ar^1$, $CH_2CH_2Ar^1$, $CH(CH_3)Ar^1$, $CH_2CH(CH_3)Ar^1$, $CH(CH_2OH)CH_2Ar^1$, $CH_2CH_2CH_2Ar^1$, $CH_2CH_2OAr^1$, $CH_2CH_2SAr^1$, $CH_2CH_2N(R^7)Ar^1$, $CH_2CH_2CH_2CH_2Ar^1$, $CH_2CH_2CH_2CH_2Ar^1$, or $CH_2CH_2CH_2CH_2CH_2CH_2Ar^1$ wherein the $C_{1-6}$alkyl group is unsubstituted or substituted with 1–2 moieties selected from the group consisting of $OR^7$, $CO_2R^7$, $N(R^7)(R^7)$, $CON(R^7)(R^7)$, $N(R^7)COR^7$, and $R^8$;

$R^2$ is hydrogen or $C_{1-6}$alkyl;

or $NR^1R^2$ taken together are

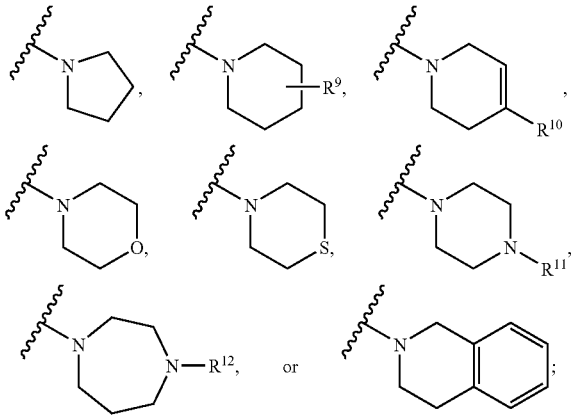

$R^3$ is hydrogen, $C_{1-6}$alkyl, $C_{3-7}$cycloalkyl, $CH_2Ar^1$, $CH_2CH_2Ar^1$, $CH(CH_3)Ar^1$, $CH_2CH(CH_3)Ar^1$, $CH(CH_2OH)CH_2Ar^1$, $CH_2CH_2CH_2Ar^1$, $CH_2CH_2OAr^1$, $CH_2CH_2SAr^1$, $CH_2CH_2N(R^7)Ar^1$, $CH_2CH_2CH_2CH_2Ar^1$, $CH_2CH_2CH_2CH_2Ar^1$, $CH_2CH_2CH_2CH_2CH_2Ar^1$, $Ar^2$, $CH_2Ar^2$, $CH_2CH_2Ar^2$, or $CH(CH_3)Ar^2$, wherein the $C_{1-6}$alkyl group is unsubstituted or substituted with 1–2 moieties selected from the group consisting of $OR^7$, $CO_2R^7$, $N(R^7)(R^7)$, $CON(R^7)(R^7)$, $N(R^7)COR^7$, and $R^8$;

$R^4$ is hydrogen or $C_{1-6}$alkyl;

or $N(R^3)(R^4)$ taken together are

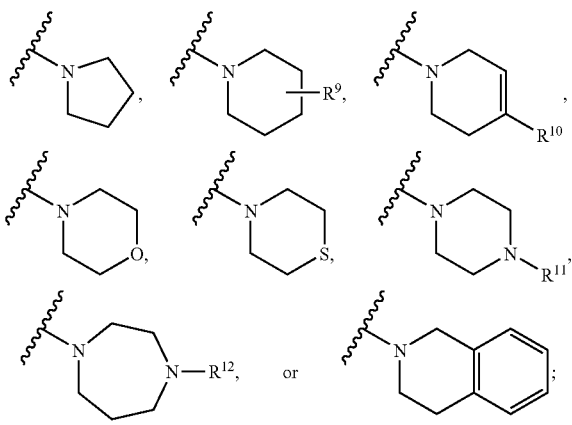

$R^5$ and $R^6$ are independently hydrogen, halo, $C_{1-6}$alkyl, trifluoromethyl, cyano, $OR^7$, or $N(R^7)(R^7)$;

$R^7$ is independently hydrogen or $C_{1-6}$alkyl;

$R^8$ is a heterocycle selected from the group consisting of tetrahydrofuranyl, pyrrolidinyl, piperidinyl, and benzopyrrolidinyl and is unsubstituted or substituted with 1 substituent selected from the group consisting of oxo, $C_{1-6}$alkyl, hydroxymethyl, benzyl, and $CO_2R^7$;

$R^9$ is hydrogen, $C_{1-6}$alkyl, $CO_2R^7$, or $CON(R^7)(R^7)$;

$R^{10}$ is hydrogen or phenyl;

$R^{11}$ is hydrogen, $C_{1-6}$alkyl, or $C_{1-6}$hydroxyalkyl;

$R^{12}$ is hydrogen, $C_{1-6}$alkyl, or $COR^7$;

$Ar^1$ is phenyl, naphthyl, pyridinyl or benzodioxolanyl and is unsubstituted or substituted with 1–2 moieties selected from the group consisting of halo, $C_{1-6}$alkyl, trifluoromethyl, cyano, pyridinyloxy, $OR^7$, $N(R^1)(R^2)$, or $Ar^2$; and $Ar^2$ is pyridinyl, pyrimidinyl, pyridizinyl, or triazinyl;

or a pharmaceutically acceptable salt thereof.

2. A compound of claim 1 where X is a bond.

3. A compound of claim 2 selected from the group consisting of isoquinoline, 1,2,3,4-tetrahydro-2-[[2-(3-methyl-1-piperidinyl)-4-(1-phenylcyclopropyl)-5-pyrimidinyl]carbonyl]-;

isoquinoline, 1,2,3,4-tetrahydro-2-[[2-(4-methyl-1-piperidinyl)-4-(1-phenylcyclopropyl)-5-pyrimidinyl]carbonyl]-;

5-pyrimidinecarboxamide, N-cyclohexyl-N-ethyl-2-(4-methyl-1-piperazinyl)-4-(1-phenylcyclopropyl)-;

5-pyrimidinecarboxamide, 2-[[2-(dimethylamino)ethyl]amino]-N-methyl-4-(1-phenylcyclopropyl)-N-(2-phenylethyl)-;

5-pyrimidinecarboxamide, N-ethyl-2-[(4-methylcyclohexyl)amino]-4-(1-phenylcyclopropyl)-N-(phenylmethyl)-;

5-pyrimidinecarboxamide, N-ethyl-2-(3-methyl-1-piperidinyl)-4-(1-phenylcyclopropyl)-N-(phenylmethyl)-;

5-pyrimidinecarboxamide, N-ethyl-2-(4-methyl-1-piperidinyl)-4-(1-phenylcyclopropyl)-N-(phenylmethyl)-;

5-pyrimidinecarboxamide, N-(1,3-benzodioxol-5-ylmethyl)-4-(1-phenylcyclopropyl)-2-(1-pyrrolidinyl)-;

5-pyrimidinecarboxamide, 2-[(4-methylcyclohexyl)amino]-N-[(1R)-1-(1-naphthalenyl)ethyl]-4-(1-phenylcyclopropyl)-;

5-pyrimidinecarboxamide, 2-(3-methyl-1-piperidinyl)-N-[(1R)-1-(1-naphthalenyl)ethyl]-4-(1-phenylcyclopropyl)-;

5-pyrimidinecarboxamide, 2-(4-methyl-1-piperidinyl)-N-[(1R)-1-(1-naphthalenyl)ethyl]-4-(1-phenylcyclopropyl)-;

5-pyrimidinecarboxamide, 2-[(4-methylcyclohexyl)amino]-N-(1-naphthalenylmethyl)-4-(1-phenylcyclopropyl)-;

5-pyrimidinecarboxamide, 2-(3-methyl-1-piperidinyl)-N-(1-naphthalenylmethyl)-4-(1-phenylcyclopropyl)-;

5-pyrimidinecarboxamide, 2-(4-methyl-1-piperidinyl)-N-(1-naphthalenylmethyl)-4-(1-phenylcyclopropyl)-;

5-pyrimidinecarboxamide, N-[(2,4-dichlorophenyl)methyl]-2-[(4-methylcyclohexyl)amino]-4-(1-phenylcyclopropyl)-;

5-pyrimidinecarboxamide, N-[(2,4-dichlorophenyl)methyl]-2-(3-methyl-1-piperidinyl)-4-(1-phenylcyclopropyl)-;

5-pyrimidinecarboxamide, N-[(2,4-dichlorophenyl)methyl]-2-(4-methyl-1-piperidinyl)-4-(1-phenylcyclopropyl)-;

5-pyrimidinecarboxamide, N-[(2,4-difluorophenyl)methyl]-2-[(4-methylcyclohexyl)amino]-4-(1-phenylcyclopropyl)-;

5-pyrimidinecarboxamide, N-[(2,4-difluorophenyl)methyl]-2-(4-methyl-1-piperidinyl)-4-(1-phenylcyclopropyl)-;

5-pyrimidinecarboxamide, N-[[3-fluoro-5-(trifluoromethyl)phenyl]methyl]-2-[(4-methylcyclohexyl)amino]-4-(1-phenylcyclopropyl)-;

5-pyrimidinecarboxamide, N-[[3-fluoro-5-(trifluoromethyl)phenyl]methyl]-4-(1-phenylcyclopropyl)-2-(1-pyrrolidinyl)-;
5-pyrimidinecarboxamide, N-[[3-fluoro-5-(trifluoromethyl)phenyl]methyl]-2-(4-methyl-1-piperazinyl)-4-(1-phenylcyclopropyl)-;
5-pyrimidinecarboxamide, N-[[3-fluoro-5-(trifluoromethyl)phenyl]methyl]-2-(3-methyl-1-piperidinyl)-4-(1-phenylcyclopropyl)-;
5-pyrimidinecarboxamide, N-[[3-fluoro-5-(trifluoromethyl)phenyl]methyl]-2-(4-methyl-1-piperidinyl)-4-(1-phenylcyclopropyl)-;
5-pyrimidinecarboxamide, N-[1-(4-fluorophenyl)ethyl]-2-[(4-methylcyclohexyl)amino]-4-(1-phenylcyclopropyl)-;
5-pyrimidinecarboxamide, N-[1-(4-fluorophenyl)ethyl]-2-(3-methyl-1-piperidinyl)-4-(1-phenylcyclopropyl)-; and
5-pyrimidinecarboxamide, N-[1-(4-fluorophenyl)ethyl]-2-(4-methyl-1-piperidinyl)-4-(1-phenylcyclopropyl)-;
or a pharmaceutically acceptable salt thereof.

4. A compound of claim 1 where X is methylene.

5. A compound of claim 4 selected from the group consisting of
5-pyrimidinecarboxamide, 4-[1-(4-chlorophenyl)cyclobutyl]-N,N-diethyl-2-[(1-methylpropyl)amino]-;
5-pyrimidinecarboxamide, 4-[1-(4-chlorophenyl)cyclobutyl]-2-[[2-(dimethylamino)ethyl]amino]-N,N-diethyl-;
isoquinoline, 2-[[4-[1-(4-chlorophenyl)cyclobutyl]-2-[[2-(dimethylamino)ethyl]amino]-5-pyrimidinyl]carbonyl]-1,2,3,4-tetrahydro-;
5-pyrimidinecarboxamide, 4-[1-(4-chlorophenyl)cyclobutyl]-2-[[2-(dimethylamino)ethyl]amino]-N-methyl-N-(2-phenylethyl)-;
5-pyrimidinecarboxamide, N-(1,3-benzodioxol-5-ylmethyl)-4-[1-(4-chlorophenyl)cyclobutyl]-2-(1-pyrrolidinyl)-;
5-pyrimidinecarboxamide, N-(1,3-benzodioxol-5-ylmethyl)-4-[1-(4-chlorophenyl)cyclobutyl]-2-(4-methyl-1-piperazinyl)-;
5-pyrimidinecarboxamide, N-(1,3-benzodioxol-5-ylmethyl)-4-[1-(4-chlorophenyl)cyclobutyl]-2-(4-methyl-1-piperidinyl)-;
5-pyrimidinecarboxamide, N-(1,3-benzodioxol-5-ylmethyl)-4-[1-(4-chlorophenyl)cyclobutyl]-2-[(1-methylpropyl)amino]-;
5-pyrimidinecarboxamide, 4-[1-(4-chlorophenyl)cyclobutyl]-2-(cyclopropylamino)-N-(1-naphthalenylmethyl)-;
5-pyrimidinecarboxamide, 4-[1-(4-chlorophenyl)cyclobutyl]-N-(1-naphthalenylmethyl)-2-(1-pyrrolidinyl)-;
5-pyrimidinecarboxamide, 4-[1-(4-chlorophenyl)cyclobutyl]-2-(3-methyl-1-piperidinyl)-N-(1-naphthalenylmethyl)-;
5-pyrimidinecarboxamide, 4-[1-(4-chlorophenyl)cyclobutyl]-N-[(2,4-dichlorophenyl)methyl]-2-(3-methyl-1-piperidinyl)-;
5-pyrimidinecarboxamide, 4-[1-(4-chlorophenyl)cyclobutyl]-N-[(2,4-dichlorophenyl)methyl]-2-(4-methyl-1-piperidinyl)-;
5-pyrimidinecarboxamide, 4-[1-(4-chlorophenyl)cyclobutyl]-N-[(2,4-difluorophenyl)methyl]-2-[(4-methylcyclohexyl)amino]-;
5-pyrimidinecarboxamide, 4-[1-(4-chlorophenyl)cyclobutyl]-N-[[3-fluoro-5-(trifluoromethyl)phenyl]methyl]-2-(3-methyl-1-piperidinyl)-;
5-pyrimidinecarboxamide, 4-[1-(4-chlorophenyl)cyclobutyl]-N-[[3-fluoro-5-(trifluoromethyl)phenyl]methyl]-2-(4-methyl-1-piperidinyl)-; and
5-pyrimidinecarboxamide, 4-[1-(4-chlorophenyl)cyclobutyl]-N-[1-(4-fluorophenyl)ethyl]-2-(3-methyl-1-piperidinyl)-;
or a pharmaceutically acceptable salt thereof.

6. A compound of claim 1 where X is ethylene.

7. A compound of claim 6 selected from the group consisting of
5-pyrimidinecarboxamide, N-methyl-4-(1-phenylcyclopentyl)-N-(phenylmethyl)-2-(1-pyrrolidinyl)-;
5-pyrimidinecarboxamide, N-methyl-2-(4-methyl-1-piperidinyl)-4-(1-phenylcyclopentyl)-N-(phenylmethyl)-;
5-pyrimidinecarboxamide, 2-(cyclopentylamino)-N-methyl-4-(1-phenylcyclopentyl)-N-(phenylmethyl)-;
5-pyrimidinecarboxamide, N,N-diethyl-2-[(4-methylcyclohexyl)amino]-4-(1-phenylcyclopentyl)-;
isoquinoline, 1,2,3,4-tetrahydro-2-[[2-[(4-methylcyclohexyl)amino]-4-(1-phenylcyclopentyl)-5-pyrimidinyl]carbonyl]-;
isoquinoline, 1,2,3,4-tetrahydro-2-[[2-(4-methyl-1-piperidinyl)-4-(1-phenylcyclopentyl)-5-pyrimidinyl]carbonyl]-;
isoquinoline, 2-[[2-(cyclopentylamino)-4-(1-phenylcyclopentyl)-5-pyrimidinyl]carbonyl]-1,2,3,4-tetrahydro-;
5-pyrimidinecarboxamide, N-cyclohexyl-N-ethyl-2-(4-methyl-1-piperidinyl)-4-(1-phenylcyclopentyl)-;
piperidine, 1-[[2-(4-methyl-1-piperidinyl)-4-(1-phenylcyclopentyl)-5-pyrimidinyl]carbonyl]-;
piperidine, 3-methyl-1-[[2-(4-methyl-1-piperidinyl)-4-(1-phenylcyclopentyl)-5-pyrimidinyl]carbonyl]-;
5-pyrimidinecarboxamide, N-methyl-4-(1-phenylcyclopentyl)-N-(2-phenylethyl)-2-(1-pyrrolidinyl)-;
5-pyrimidinecarboxamide, N-methyl-2-(3-methyl-1-piperidinyl)-4-(1-phenylcyclopentyl)-N-(2-phenylethyl)-;
5-pyrimidinecarboxamide, N-methyl-2-(4-methyl-1-piperidinyl)-4-(1-phenylcyclopentyl)-N-(2-phenylethyl)-;
5-pyrimidinecarboxamide, N,N-bis(1-methylethyl)-2-(3-methyl-1-piperidinyl)-4-(1-phenylcyclopentyl)-;
5-pyrimidinecarboxamide, N-ethyl-N-methyl-2-(3-methyl-1-piperidinyl)-4-(1-phenylcyclopentyl)-;
5-pyrimidinecarboxamide, N-ethyl-2-[(4-methylcyclohexyl)amino]-4-(1-phenylcyclopentyl)-N-(phenylmethyl)-;
5-pyrimidinecarboxamide, N-ethyl-2-(3-methyl-1-piperidinyl)-4-(1-phenylcyclopentyl)-N-(phenylmethyl)-;
5-pyrimidinecarboxamide, N-ethyl-2-(4-methyl-1-piperidinyl)-4-(1-phenylcyclopentyl)-N-(phenylmethyl)-;
5-pyrimidinecarboxamide, N-ethyl-2-[(1-methylpropyl)amino]-4-(1-phenylcyclopentyl)-N-(phenylmethyl)-;
5-pyrimidinecarboxamide, 2-(cyclopentylamino)-N-ethyl-4-(1-phenylcyclopentyl)-N-(phenylmethyl)-;
5-pyrimidinecarboxamide, N-(1,3-benzodioxol-5-ylmethyl)-2-(cyclopropylamino)-4-(1-phenylcyclopentyl)-;
5-pyrimidinecarboxamide, N-(1,3-benzodioxol-5-ylmethyl)-2-[(4-methylcyclohexyl)amino]-4-(1-phenylcyclopentyl)-;
5-pyrimidinecarboxamide, N-(1,3-benzodioxol-5-ylmethyl)-2-(4-methyl-1-piperazinyl)-4-(1-phenylcyclopentyl)-;

5-pyrimidinecarboxamide, N-(1,3-benzodioxol-5-ylmethyl)-2-(3-methyl-1-piperidinyl)-4-(1-phenylcyclopentyl)-;
5-pyrimidinecarboxamide, N-(1,3-benzodioxol-5-ylmethyl)-2-(4-methyl-1-piperidinyl)-4-(1-phenylcyclopentyl)-;
5-pyrimidinecarboxamide, N-(1,3-benzodioxol-5-ylmethyl)-2-[(1-methylpropyl)amino]-4-(1-phenylcyclopentyl)-;
5-pyrimidinecarboxamide, 2-[(4-methylcyclohexyl)amino]-N-[1-(1-naphthalenyl)ethyl]-4-(1-phenylcyclopentyl)-;
5-pyrimidinecarboxamide, N-[1-(1-naphthalenyl)ethyl]-4-(1-phenylcyclopentyl)-2-(1-pyrrolidinyl)-;
5-pyrimidinecarboxamide, 2-(3-methyl-1-piperidinyl)-N-[1-(1-naphthalenyl)ethyl]-4-(1-phenylcyclopentyl)-;
5-pyrimidinecarboxamide, 2-(4-methyl-1-piperidinyl)-N-[1-(1-naphthalenyl)ethyl]-4-(1-phenylcyclopentyl)-;
5-pyrimidinecarboxamide, 2-[(1-methylpropyl)amino]-N-[1-(1-naphthalenyl)ethyl]-4-(1-phenylcyclopentyl)-;
5-pyrimidinecarboxamide, 2-(cyclopentylamino)-N-[1-(1-naphthalenyl)ethyl]-4-(1-phenylcyclopentyl)-;
5-pyrimidinecarboxamide, 2-(cyclopropylamino)-N-(1-naphthalenylmethyl)-4-(1-phenylcyclopentyl)-;
5-pyrimidinecarboxamide, 2-[(4-methylcyclohexyl)amino]-N-(1-naphthalenylmethyl)-4-(1-phenylcyclopentyl)-;
5-pyrimidinecarboxamide, 2-(3-methyl-1-piperidinyl)-N-(1-naphthalenylmethyl)-4-(1-phenylcyclopentyl)-;
5-pyrimidinecarboxamide, 2-(4-methyl-1-piperidinyl)-N-(1-naphthalenylmethyl)-4-(1-phenylcyclopentyl)-;
5-pyrimidinecarboxamide, 2-[(1-methylpropyl)amino]-N-(1-naphthalenylmethyl)-4-(1-phenylcyclopentyl)-;
5-pyrimidinecarboxamide, N-[(3,4-dichlorophenyl)methyl]-2-[(4-methylcyclohexyl)amino]-4-(1-phenylcyclopentyl)-;
5-pyrimidinecarboxamide, N-[(3,4-dichlorophenyl)methyl]-2-(3-methyl-1-piperidinyl)-4-(1-phenylcyclopentyl)-;
5-pyrimidinecarboxamide, N-[(3,4-dichlorophenyl)methyl]-2-(4-methyl-1-piperidinyl)-4-(1-phenylcyclopentyl)-;
5-pyrimidinecarboxamide, 2-(cyclopropylamino)-N-[(2,4-dichlorophenyl)methyl]-4-(1-phenylcyclopentyl)-;
5-pyrimidinecarboxamide, N-[(2,4-dichlorophenyl)methyl]-2-[(4-methylcyclohexyl)amino]-4-(1-phenylcyclopentyl)-;
5-pyrimidinecarboxamide, N-[(2,4-dichlorophenyl)methyl]-4-(1-phenylcyclopentyl)-2-(1-pyrrolidinyl)-;
5-pyrimidinecarboxamide, N-[(2,4-dichlorophenyl)methyl]-2-(3-methyl-1-piperidinyl)-4-(1-phenylcyclopentyl)-;
5-pyrimidinecarboxamide, N-[(2,4-dichlorophenyl)methyl]-2-(4-methyl-1-piperidinyl)-4-(1-phenylcyclopentyl)-;
5-pyrimidinecarboxamide, N-[(2,4-dichlorophenyl)methyl]-2-[(1-methylpropyl)amino]-4-(1-phenylcyclopentyl)-;
5-pyrimidinecarboxamide, 2-(cyclopentylamino)-N-[(2,4-dichlorophenyl)methyl]-4-(1-phenylcyclopentyl)-;
5-pyrimidinecarboxamide, N-[(2,4-difluorophenyl)methyl]-2-[(4-methylcyclohexyl)amino]-4-(1-phenylcyclopentyl)-;
5-pyrimidinecarboxamide, N-[(2,4-difluorophenyl)methyl]-4-(1-phenylcyclopentyl)-2-(1-pyrrolidinyl)-;
5-pyrimidinecarboxamide, N-[(2,4-difluorophenyl)methyl]-2-(3-methyl-1-piperidinyl)-4-(1-phenylcyclopentyl)-;
5-pyrimidinecarboxamide, N-[(2,4-difluorophenyl)methyl]-2-(4-methyl-1-piperidinyl)-4-(1-phenylcyclopentyl)-;
5-pyrimidinecarboxamide, N-[(2,4-difluorophenyl)methyl]-2-[(1-methylpropyl)amino]-4-(1-phenylcyclopentyl)-;
5-pyrimidinecarboxamide, 2-(cyclopentylamino)-N-[(2,4-difluorophenyl)methyl]-4-(1-phenylcyclopentyl)-;
5-pyrimidinecarboxamide, 2-(cyclopropylamino)-N-[[3-fluoro-5-(trifluoromethyl)phenyl]methyl]-4-(1-phenylcyclopentyl)-;
5-pyrimidinecarboxamide, N-[[3-fluoro-5-(trifluoromethyl)phenyl]methyl]-2-[(4-methylcyclohexyl)amino]-4-(1-phenylcyclopentyl)-;
5-pyrimidinecarboxamide, N-[[3-fluoro-5-(trifluoromethyl)phenyl]methyl]-4-(1-phenylcyclopentyl)-2-(1-pyrrolidinyl)-;
5-pyrimidinecarboxamide, N-[[3-fluoro-5-(trifluoromethyl)phenyl]methyl]-2-(4-methyl-1-piperazinyl)-4-(1-phenylcyclopentyl)-;
5-pyrimidinecarboxamide, N-[[3-fluoro-5-(trifluoromethyl)phenyl]methyl]-2-(3-methyl-1-piperidinyl)-4-(1-phenylcyclopentyl)-;
5-pyrimidinecarboxamide, N-[[3-fluoro-5-(trifluoromethyl)phenyl]methyl]-2-(4-methyl-1-piperidinyl)-4-(1-phenylcyclopentyl)-;
5-pyrimidinecarboxamide, N-[[3-fluoro-5-(trifluoromethyl)phenyl]methyl]-2-[(1-methylpropyl)amino]-4-(1-phenylcyclopentyl)-;
5-pyrimidinecarboxamide, 2-[[2-(dimethylamino)ethyl]amino]-N-[[3-fluoro-5-(trifluoromethyl)phenyl]methyl]-4-(1-phenylcyclopentyl)-;
5-pyrimidinecarboxamide, 2-(cyclopentylamino)-N-[[3-fluoro-5-(trifluoromethyl)phenyl]methyl]-4-(1-phenylcyclopentyl)-;
5-pyrimidinecarboxamide, N-[1-(4-fluorophenyl)ethyl]-2-[(4-methylcyclohexyl)amino]-4-(1-phenylcyclopentyl)-;
5-pyrimidinecarboxamide, N-[1-(4-fluorophenyl)ethyl]-4-(1-phenylcyclopentyl)-2-(1-pyrrolidinyl)-;
5-pyrimidinecarboxamide, N-[1-(4-fluorophenyl)ethyl]-2-(4-methyl-1-piperazinyl)-4-(1-phenylcyclopentyl)-;
5-pyrimidinecarboxamide, N-[1-(4-fluorophenyl)ethyl]-2-(4-methyl-1-piperidinyl)-4-(1-phenylcyclopentyl)-;
5-pyrimidinecarboxamide, N-[1-(4-fluorophenyl)ethyl]-2-[(1-methylpropyl)amino]-4-(1-phenylcyclopentyl)-;
5-pyrimidinecarboxamide, 2-(cyclopentylamino)-N-[1-(4-fluorophenyl)ethyl]-4-(1-phenylcyclopentyl)-;
5-pyrimidinecarboxamide, 2-[(4-methylcyclohexyl)amino]-4-(1-phenylcyclopentyl)-N-[[4-(trifluoromethyl)phenyl]methyl]-;
5-pyrimidinecarboxamide, 2-(4-methyl-1-piperidinyl)-4-(1-phenylcyclopentyl)-N-[[4-(trifluoromethyl)phenyl]methyl]-;
5-pyrimidinecarboxamide, 4-[1-(4-chlorophenyl)cyclopentyl]-N-methyl-2-(4-methyl-1-piperazinyl)-N-(phenylmethyl)-;
5-pyrimidinecarboxamide, 4-[1-(4-chlorophenyl)cyclopentyl]-N-methyl-2-(4-methyl-1-piperidinyl)-N-(phenylmethyl)-;
5-pyrimidinecarboxamide, 4-[1-(4-chlorophenyl)cyclopentyl]-2-(cyclopentylamino)-N-methyl-N-(phenylmethyl)-;

isoquinoline, 2-[[4-[1-(4-chlorophenyl)cyclopentyl]-2-(cyclopentylamino)-5-pyrimidinyl]carbonyl]-1,2,3,4-tetrahydro-;

5-pyrimidinecarboxamide, 4-[1-(4-chlorophenyl)cyclopentyl]-N-cyclohexyl-N-ethyl-2-[(1-methylpropyl)amino]-;

piperidine, 1-[[4-[1-(4-chlorophenyl)cyclopentyl]-2-(cyclopropylamino)-5-pyrimidinyl]carbonyl]-3-methyl-;

5-pyrimidinecarboxamide, 4-[1-(4-chlorophenyl)cyclopentyl]-2-(cyclopropylamino)-N-methyl-N-(2-phenylethyl)-;

5-pyrimidinecarboxamide, 4-[1-(4-chlorophenyl)cyclopentyl]-N-methyl-2-[(4-methylcyclohexyl)amino]-N-(2-phenylethyl)-;

5-pyrimidinecarboxamide, 4-[1-(4-chlorophenyl)cyclopentyl]-N-methyl-N-(2-phenylethyl)-2-(1-pyrrolidinyl)-;

5-pyrimidinecarboxamide, 4-[1-(4-chlorophenyl)cyclopentyl]-2-(cyclopentylamino)-N-methyl-N-(2-phenylethyl)-;

5-pyrimidinecarboxamide, 4-[1-(4-chlorophenyl)cyclopentyl]-2-(cyclopentylamino)-N-ethyl-N-(phenylmethyl)-;

5-pyrimidinecarboxamide, N-(1,3-benzodioxol-5-ylmethyl)-4-[1-(4-chlorophenyl)cyclopentyl]-2-(cyclopropylamino)-;

5-pyrimidinecarboxamide, N-(1,3-benzodioxol-5-ylmethyl)-4-[1-(4-chlorophenyl)cyclopentyl]-2-[(4-methylcyclohexyl)amino]-;

5-pyrimidinecarboxamide, N-(1,3-benzodioxol-5-ylmethyl)-4-[1-(4-chlorophenyl)cyclopentyl]-2-(1-pyrrolidinyl)-;

5-pyrimidinecarboxamide, N-(1,3-benzodioxol-5-ylmethyl)-4-[1-(4-chlorophenyl)cyclopentyl]-2-(3-methyl-1-piperidinyl)-;

5-pyrimidinecarboxamide, N-(1,3-benzodioxol-5-ylmethyl)-4-[1-(4-chlorophenyl)cyclopentyl]-2-(4-methyl-1-piperidinyl)-;

5-pyrimidinecarboxamide, N-(1,3-benzodioxol-5-ylmethyl)-4-[1-(4-chlorophenyl)cyclopentyl]-2-[(1-methylpropyl)amino]-;

5-pyrimidinecarboxamide, N-(1,3-benzodioxol-5-ylmethyl)-4-[1-(4-chlorophenyl)cyclopentyl]-2-(cyclopentylamino)-;

5-pyrimidinecarboxamide, 4-[1-(4-chlorophenyl)cyclopentyl]-2-(cyclopropylamino)-N-[1-(1-naphthalenyl)ethyl]-;

5-pyrimidinecarboxamide, 4-[1-(4-chlorophenyl)cyclopentyl]-N-[1-(1-naphthalenyl)ethyl]-2-(1-pyrrolidinyl)-;

5-pyrimidinecarboxamide, 4-[1-(4-chlorophenyl)cyclopentyl]-2-(4-methyl-1-piperazinyl)-N-[1-(1-naphthalenyl)ethyl]-;

5-pyrimidinecarboxamide, 4-[1-(4-chlorophenyl)cyclopentyl]-2-(3-methyl-1-piperidinyl)-N-[1-(1-naphthalenyl)ethyl]-;

5-pyrimidinecarboxamide, 4-[1-(4-chlorophenyl)cyclopentyl]-2-(4-methyl-1-piperidinyl)-N-[1-(1-naphthalenyl)ethyl]-;

5-pyrimidinecarboxamide, 4-[1-(4-chlorophenyl)cyclopentyl]-2-[(1-methylpropyl)amino]-N-[1-(1-naphthalenyl)ethyl]-;

5-pyrimidinecarboxamide, 4-[1-(4-chlorophenyl)cyclopentyl]-2-[[2-(dimethylamino)ethyl]amino]-N-[1-(1-naphthalenyl)ethyl]-;

5-pyrimidinecarboxamide, 4-[1-(4-chlorophenyl)cyclopentyl]-2-(cyclopentylamino)-N-[1-(1-naphthalenyl)ethyl]-;

5-pyrimidinecarboxamide, 4-[1-(4-chlorophenyl)cyclopentyl]-2-(cyclopropylamino)-N-(1-naphthalenylmethyl)-;

5-pyrimidinecarboxamide, 4-[1-(4-chlorophenyl)cyclopentyl]-2-[(4-methylcyclohexyl)amino]-N-(1-naphthalenylmethyl)-;

5-pyrimidinecarboxamide, 4-[1-(4-chlorophenyl)cyclopentyl]-N-(1-naphthalenylmethyl)-2-(1-pyrrolidinyl)-;

5-pyrimidinecarboxamide, 4-[1-(4-chlorophenyl)cyclopentyl]-2-(4-methyl-1-piperazinyl)-N-(1-naphthalenylmethyl)-;

5-pyrimidinecarboxamide, 4-[1-(4-chlorophenyl)cyclopentyl]-2-(3-methyl-1-piperidinyl)-N-(1-naphthalenylmethyl)-;

5-pyrimidinecarboxamide, 4-[1-(4-chlorophenyl)cyclopentyl]-2-(4-methyl-1-piperidinyl)-N-(1-naphthalenylmethyl)-;

5-pyrimidinecarboxamide, 4-[1-(4-chlorophenyl)cyclopentyl]-2-[(1-methylpropyl)amino]-N-(1-naphthalenylmethyl)-;

5-pyrimidinecarboxamide, 4-[1-(4-chlorophenyl)cyclopentyl]-2-(cyclopentylamino)-N-(1-naphthalenylmethyl)-;

5-pyrimidinecarboxamide, 4-[1-(4-chlorophenyl)cyclopentyl]-N-[(3,4-dichlorophenyl)methyl]-2-(4-methyl-1-piperazinyl)-;

5-pyrimidinecarboxamide, 4-[1-(4-chlorophenyl)cyclopentyl]-N-[(3,4-dichlorophenyl)methyl]-2-(3-methyl-1-piperidinyl)-;

5-pyrimidinecarboxamide, 4-[1-(4-chlorophenyl)cyclopentyl]-N-[(3,4-dichlorophenyl)methyl]-2-(4-methyl-1-piperidinyl)-;

5-pyrimidinecarboxamide, 4-[1-(4-chlorophenyl)cyclopentyl]-2-(cyclopropylamino)-N-[(2,4-dichlorophenyl)methyl]-;

5-pyrimidinecarboxamide, 4-[1-(4-chlorophenyl)cyclopentyl]-N-[(2,4-dichlorophenyl)methyl]-2-[(4-methylcyclohexyl)amino]-;

5-pyrimidinecarboxamide, 4-[1-(4-chlorophenyl)cyclopentyl]-N-[(2,4-dichlorophenyl)methyl]-2-(1-pyrrolidinyl)-;

5-pyrimidinecarboxamide, 4-[1-(4-chlorophenyl)cyclopentyl]-N-[(2,4-dichlorophenyl)methyl]-2-(4-methyl-1-piperazinyl)-;

5-pyrimidinecarboxamide, 4-[1-(4-chlorophenyl)cyclopentyl]-N-[(2,4-dichlorophenyl)methyl]-2-(3-methyl-1-piperidinyl)-;

5-pyrimidinecarboxamide, 4-[1-(4-chlorophenyl)cyclopentyl]-N-[(2,4-dichlorophenyl)methyl]-2-(4-methyl-1-piperidinyl)-;

5-pyrimidinecarboxamide, 4-[1-(4-chlorophenyl)cyclopentyl]-N-[(2,4-dichlorophenyl)methyl]-2-[methyl(1-methyl-4-piperidinyl)amino]-;

5-pyrimidinecarboxamide, 4-[1-(4-chlorophenyl)cyclopentyl]-N-[(2,4-dichlorophenyl)methyl]-2-[(1-methylpropyl)amino]-;

5-pyrimidinecarboxamide, 4-[1-(4-chlorophenyl)cyclopentyl]-N-[(2,4-dichlorophenyl)methyl]-2-[[2-(dimethylamino)ethyl]amino]-;

5-pyrimidinecarboxamide, 4-[1-(4-chlorophenyl)cyclopentyl]-2-(cyclopentylamino)-N-[(2,4-dichlorophenyl)methyl]-;

5-pyrimidinecarboxamide, 4-[1-(4-chlorophenyl)cyclopentyl]-N-[(2,4-difluorophenyl)methyl]-2-[(4-methylcyclohexyl)amino]-;
5-pyrimidinecarboxamide, 4-[1-(4-chlorophenyl)cyclopentyl]-N-[(2,4-difluorophenyl)methyl]-2-(3-methyl-1-piperidinyl)-;
5-pyrimidinecarboxamide, 4-[1-(4-chlorophenyl)cyclopentyl]-N-[(2,4-difluorophenyl)methyl]-2-(4-methyl-1-piperidinyl)-;
5-pyrimidinecarboxamide, 4-[1-(4-chlorophenyl)cyclopentyl]-2-(cyclopentylamino)-N-[(2,4-difluorophenyl)methyl]-;
5-pyrimidinecarboxamide, 4-[1-(4-chlorophenyl)cyclopentyl]-N-[[3-fluoro-5-(trifluoromethyl)phenyl]methyl]-2-[(4-methylcyclohexyl)amino]-;
5-pyrimidinecarboxamide, 4-[1-(4-chlorophenyl)cyclopentyl]-N-[[3-fluoro-5-(trifluoromethyl)phenyl]methyl]-2-(1-pyrrolidinyl)-;
5-pyrimidinecarboxamide, 4-[1-(4-chlorophenyl)cyclopentyl]-N-[[3-fluoro-5-(trifluoromethyl)phenyl]methyl]-2-(3-methyl-1-piperidinyl)-;
5-pyrimidinecarboxamide, 4-[1-(4-chlorophenyl)cyclopentyl]-N-[[3-fluoro-5-(trifluoromethyl)phenyl]methyl]-2-(4-methyl-1-piperidinyl)-;
5-pyrimidinecarboxamide, 4-[1-(4-chlorophenyl)cyclopentyl]-N-[[3-fluoro-5-(trifluoromethyl)phenyl]methyl]-2-[methyl(1-methyl-4-piperidinyl)amino]-;
5-pyrimidinecarboxamide, 4-[1-(4-chlorophenyl)cyclopentyl]-2-[[2-(dimethylamino)ethyl]amino]-N-[[3-fluoro-5-(trifluoromethyl)phenyl]methyl]-;
5-pyrimidinecarboxamide, 4-[1-(4-chlorophenyl)cyclopentyl]-2-(cyclopentylamino)-N-[[3-fluoro-5-(trifluoromethyl)phenyl]methyl]-;
5-pyrimidinecarboxamide, 4-[1-(4-chlorophenyl)cyclopentyl]-N-[1-(4-fluorophenyl)ethyl]-2-[(4-methylcyclohexyl)amino]-;
5-pyrimidinecarboxamide, 4-[1-(4-chlorophenyl)cyclopentyl]-N-[1-(4-fluorophenyl)ethyl]-2-(3-methyl-1-piperidinyl)-;
5-pyrimidinecarboxamide, 4-[1-(4-chlorophenyl)cyclopentyl]-N-[1-(4-fluorophenyl)ethyl]-2-(4-methyl-1-piperidinyl)-;
5-pyrimidinecarboxamide, 4-[1-(4-chlorophenyl)cyclopentyl]-N-[1-(4-fluorophenyl)ethyl]-2-[(1-methylpropyl)amino]-;
5-pyrimidinecarboxamide, 4-[1-(4-chlorophenyl)cyclopentyl]-2-(cyclopentylamino)-N-[1-(4-fluorophenyl)ethyl]-;
5-pyrimidinecarboxamide, 4-[1-(4-chlorophenyl)cyclopentyl]-2-(4-methyl-1-piperazinyl)-N-[[4-(trifluoromethyl)phenyl]methyl]-;
5-pyrimidinecarboxamide, 4-[1-(4-chlorophenyl)cyclopentyl]-2-(4-methyl-1-piperidinyl)-N-[[4-(trifluoromethyl)phenyl]methyl]-;
5-pyrimidinecarboxamide, 4-[1-(4-chlorophenyl)cyclopentyl]-2-[methyl(1-methyl-4-piperidinyl)amino]-N-[[4-(trifluoromethyl)phenyl]methyl]-;
5-pyrimidinecarboxamide, 4-[1-(4-fluorophenyl)cyclopentyl]-N-methyl-2-(3-methyl-1-piperidinyl)-N-(phenylmethyl)-;
5-pyrimidinecarboxamide, 4-[1-(4-fluorophenyl)cyclopentyl]-N-methyl-2-(4-methyl-1-piperidinyl)-N-(phenylmethyl)-;
5-pyrimidinecarboxamide, N-cyclohexyl-4-[1-(4-fluorophenyl)cyclopentyl]-N-methyl-2-[(4-methylcyclohexyl)amino]-;
5-pyrimidinecarboxamide, N-cyclohexyl-4-[1-(4-fluorophenyl)cyclopentyl]-N-methyl-2-(4-methyl-1-piperidinyl)-;
5-pyrimidinecarboxamide, N-cyclohexyl-2-(cyclopentylamino)-4-[1-(4-fluorophenyl)cyclopentyl]-N-methyl-;
isoquinoline, 2-[[4-[1-(4-fluorophenyl)cyclopentyl]-2-[(4-methylcyclohexyl)amino]-5-pyrimidinyl]carbonyl]-1,2,3,4-tetrahydro-;
isoquinoline, 2-[[4-[1-(4-fluorophenyl)cyclopentyl]-2-(3-methyl-1-piperidinyl)-5-pyrimidinyl]carbonyl]-1,2,3,4-tetrahydro-;
isoquinoline, 2-[[4-[1-(4-fluorophenyl)cyclopentyl]-2-(4-methyl-1-piperidinyl)-5-pyrimidinyl]carbonyl]-1,2,3,4-tetrahydro-;
5-pyrimidinecarboxamide, N-cyclohexyl-N-ethyl-4-[1-(4-fluorophenyl)cyclopentyl]-2-(1-pyrrolidinyl)-;
5-pyrimidinecarboxamide, N-cyclohexyl-N-ethyl-4-[1-(4-fluorophenyl)cyclopentyl]-2-(3-methyl-1-piperidinyl)-;
5-pyrimidinecarboxamide, N-cyclohexyl-N-ethyl-4-[1-(4-fluorophenyl)cyclopentyl]-2-(4-methyl-1-piperidinyl)-;
5-pyrimidinecarboxamide, N-cyclohexyl-N-ethyl-4-[1-(4-fluorophenyl)cyclopentyl]-2-[(1-methylpropyl)amino]-;
5-pyrimidinecarboxamide, N-cyclohexyl-2-(cyclopentylamino)-N-ethyl-4-[1-(4-fluorophenyl)cyclopentyl]-;
piperidine, 1-[[4-[1-(4-fluorophenyl)cyclopentyl]-2-(4-methyl-1-piperidinyl)-5-pyrimidinyl]carbonyl]-3-methyl-;
5-pyrimidinecarboxamide, 4-[1-(4-fluorophenyl)cyclopentyl]-N-methyl-2-[(4-methylcyclohexyl)amino]-N-(2-phenylethyl)-;
5-pyrimidinecarboxamide, 4-[1-(4-fluorophenyl)cyclopentyl]-N-methyl-N-(2-phenylethyl)-2-(1-pyrrolidinyl)-;
5-pyrimidinecarboxamide, 4-[1-(4-fluorophenyl)cyclopentyl]-N-methyl-2-(3-methyl-1-piperidinyl)-N-(2-phenylethyl)-;
5-pyrimidinecarboxamide, 4-[1-(4-fluorophenyl)cyclopentyl]-N-methyl-2-(4-methyl-1-piperidinyl)-N-(2-phenylethyl)-;
5-pyrimidinecarboxamide, 4-[1-(4-fluorophenyl)cyclopentyl]-N-methyl-2-[(1-methylpropyl)amino]-N-(2-phenylethyl)-;
5-pyrimidinecarboxamide, 4-[1-(4-fluorophenyl)cyclopentyl]-N,N-bis(1-methylethyl)-2-(3-methyl-1-piperidinyl)-;
5-pyrimidinecarboxamide, N-ethyl-4-[1-(4-fluorophenyl)cyclopentyl]-N-methyl-2-[(4-methylcyclohexyl)amino]-;
5-pyrimidinecarboxamide, N-ethyl-4-[1-(4-fluorophenyl)cyclopentyl]-N-methyl-2-(3-methyl-1-piperidinyl)-;
5-pyrimidinecarboxamide, N-ethyl-4-[1-(4-fluorophenyl)cyclopentyl]-N-methyl-2-(4-methyl-1-piperidinyl)-;
5-pyrimidinecarboxamide, N-ethyl-4-[1-(4-fluorophenyl)cyclopentyl]-2-[(4-methylcyclohexyl)amino]-N-(phenylmethyl)-;
5-pyrimidinecarboxamide, N-ethyl-4-[1-(4-fluorophenyl)cyclopentyl]-2-(3-methyl-1-piperidinyl)-N-(phenylmethyl)-;
5-pyrimidinecarboxamide, N-ethyl-4-[1-(4-fluorophenyl)cyclopentyl]-2-(4-methyl-1-piperidinyl)-N-(phenylmethyl)-;
5-pyrimidinecarboxamide, N-ethyl-4-[1-(4-fluorophenyl)cyclopentyl]-2-[(1-methylpropyl)amino]-N-(phenylmethyl)-;

5-pyrimidinecarboxamide, 2-(cyclopentylamino)-N-ethyl-4-[1-(4-fluorophenyl)cyclopentyl]-N-(phenylmethyl)-;

5-pyrimidinecarboxamide, N-(1,3-benzodioxol-5-ylmethyl)-2-(cyclopropylamino)-4-[1-(4-fluorophenyl)cyclopentyl]-;

5-pyrimidinecarboxamide, N-(1,3-benzodioxol-5-ylmethyl)-4-[1-(4-fluorophenyl)cyclopentyl]-2-[(4-methylcyclohexyl)amino]-;

5-pyrimidinecarboxamide, N-(1,3-benzodioxol-5-ylmethyl)-4-[1-(4-fluorophenyl)cyclopentyl]-2-(1-pyrrolidinyl)-;

5-pyrimidinecarboxamide, N-(1,3-benzodioxol-5-ylmethyl)-4-[1-(4-fluorophenyl)cyclopentyl]-2-(3-methyl-1-piperidinyl)-;

5-pyrimidinecarboxamide, N-(1,3-benzodioxol-5-ylmethyl)-4-[1-(4-fluorophenyl)cyclopentyl]-2-(4-methyl-1-piperidinyl)-;

5-pyrimidinecarboxamide, N-(1,3-benzodioxol-5-ylmethyl)-4-[1-(4-fluorophenyl)cyclopentyl]-2-[(1-methylpropyl)amino]-;

5-pyrimidinecarboxamide, N-(1,3-benzodioxol-5-ylmethyl)-2-[[2-(dimethylamino)ethyl]amino]-4-[1-(4-fluorophenyl)cyclopentyl]-;

5-pyrimidinecarboxamide, 2-(cyclopropylamino)-4-[1-(4-fluorophenyl)cyclopentyl]-N-[1-(1-naphthalenyl)ethyl]-;

5-pyrimidinecarboxamide, 4-[1-(4-fluorophenyl)cyclopentyl]-2-[(4-methylcyclohexyl)amino]-N-[1-(1-naphthalenyl)ethyl]-;

5-pyrimidinecarboxamide, 4-[1-(4-fluorophenyl)cyclopentyl]-N-[1-(1-naphthalenyl)ethyl]-2-(1-pyrrolidinyl)-;

5-pyrimidinecarboxamide, 4-[1-(4-fluorophenyl)cyclopentyl]-2-(4-methyl-1-piperazinyl)-N-[1-(1-naphthalenyl)ethyl]-;

5-pyrimidinecarboxamide, 4-[1-(4-fluorophenyl)cyclopentyl]-2-(3-methyl-1-piperidinyl)-N-[1-(1-naphthalenyl)ethyl]-;

5-pyrimidinecarboxamide, 4-[1-(4-fluorophenyl)cyclopentyl]-2-(4-methyl-1-piperidinyl)-N-[1-(1-naphthalenyl)ethyl]-;

5-pyrimidinecarboxamide, 4-[1-(4-fluorophenyl)cyclopentyl]-2-[(1-methylpropyl)amino]-N-[1-(1-naphthalenyl)ethyl]-;

5-pyrimidinecarboxamide, 2-(cyclopentylamino)-4-[1-(4-fluorophenyl)cyclopentyl]-N-[1-(1-naphthalenyl)ethyl]-;

5-pyrimidinecarboxamide, 4-[1-(4-fluorophenyl)cyclopentyl]-2-[(4-methylcyclohexyl)amino]-N-(1-naphthalenylmethyl)-;

5-pyrimidinecarboxamide, 4-[1-(4-fluorophenyl)cyclopentyl]-N-(1-naphthalenylmethyl)-2-(1-pyrrolidinyl)-;

5-pyrimidinecarboxamide, 4-[1-(4-fluorophenyl)cyclopentyl]-2-(3-methyl-1-piperidinyl)-N-(1-naphthalenylmethyl)-;

5-pyrimidinecarboxamide, 4-[1-(4-fluorophenyl)cyclopentyl]-2-(4-methyl-1-piperidinyl)-N-(1-naphthalenylmethyl)-;

5-pyrimidinecarboxamide, 4-[1-(4-fluorophenyl)cyclopentyl]-2-[(1-methylpropyl)amino]-N-(1-naphthalenylmethyl)-;

5-pyrimidinecarboxamide, 2-(cyclopentylamino)-4-[1-(4-fluorophenyl)cyclopentyl]-N-(1-naphthalenylmethyl)-;

5-pyrimidinecarboxamide, N-[(3,4-dichlorophenyl)methyl]-4-[1-(4-fluorophenyl)cyclopentyl]-2-(4-methyl-1-piperazinyl)-;

5-pyrimidinecarboxamide, N-[(3,4-dichlorophenyl)methyl]-4-[1-(4-fluorophenyl)cyclopentyl]-2-(3-methyl-1-piperidinyl)-;

5-pyrimidinecarboxamide, N-[(3,4-dichlorophenyl)methyl]-4-[1-(4-fluorophenyl)cyclopentyl]-2-(4-methyl-1-piperidinyl)-;

5-pyrimidinecarboxamide, N-[(3,4-dichlorophenyl)methyl]-2-[[2-(dimethylamino)ethyl]amino]-4-[1-(4-fluorophenyl)cyclopentyl]-;

5-pyrimidinecarboxamide, 2-(cyclopentylamino)-N-[(3,4-dichlorophenyl)methyl]-4-[1-(4-fluorophenyl)cyclopentyl]-;

5-pyrimidinecarboxamide, 2-(cyclopropylamino)-N-[(2,4-dichlorophenyl)methyl]-4-[1-(4-fluorophenyl)cyclopentyl]-;

5-pyrimidinecarboxamide, N-[(2,4-dichlorophenyl)methyl]-4-[1-(4-fluorophenyl)cyclopentyl]-2-[(4-methylcyclohexyl)amino]-;

5-pyrimidinecarboxamide, N-[(2,4-dichlorophenyl)methyl]-4-[1-(4-fluorophenyl)cyclopentyl]-2-(1-pyrrolidinyl)-;

5-pyrimidinecarboxamide, N-[(2,4-dichlorophenyl)methyl]-4-[1-(4-fluorophenyl)cyclopentyl]-2-(3-methyl-1-piperidinyl)-;

5-pyrimidinecarboxamide, N-[(2,4-dichlorophenyl)methyl]-4-[1-(4-fluorophenyl)cyclopentyl]-2-(4-methyl-1-piperidinyl)-;

5-pyrimidinecarboxamide, N-[(2,4-dichlorophenyl)methyl]-4-[1-(4-fluorophenyl)cyclopentyl]-2-[methyl(1-methyl-4-piperidinyl)amino]-;

5-pyrimidinecarboxamide, N-[(2,4-dichlorophenyl)methyl]-4-[1-(4-fluorophenyl)cyclopentyl]-2-[(1-methylpropyl)amino]-;

5-pyrimidinecarboxamide, 2-(cyclopentylamino)-N-[(2,4-dichlorophenyl)methyl]-4-[1-(4-fluorophenyl)cyclopentyl]-;

5-pyrimidinecarboxamide, N-[(2,4-difluorophenyl)methyl]-4-[1-(4-fluorophenyl)cyclopentyl]-2-[(4-methylcyclohexyl)amino]-;

5-pyrimidinecarboxamide, N-[(2,4-difluorophenyl)methyl]-4-[1-(4-fluorophenyl)cyclopentyl]-2-(4-methyl-1-piperazinyl)-;

5-pyrimidinecarboxamide, N-[(2,4-difluorophenyl)methyl]-4-[1-(4-fluorophenyl)cyclopentyl]-2-(3-methyl-1-piperidinyl)-;

5-pyrimidinecarboxamide, N-[(2,4-difluorophenyl)methyl]-4-[1-(4-fluorophenyl)cyclopentyl]-2-(4-methyl-1-piperidinyl)-;

5-pyrimidinecarboxamide, N-[(2,4-difluorophenyl)methyl]-4-[1-(4-fluorophenyl)cyclopentyl]-2-[methyl(1-methyl-4-piperidinyl)amino]-;

5-pyrimidinecarboxamide, N-[(2,4-difluorophenyl)methyl]-2-[[2-(dimethylamino)ethyl]amino]-4-[1-(4-fluorophenyl)cyclopentyl]-;

5-pyrimidinecarboxamide, 2-(cyclopentylamino)-N-[(2,4-difluorophenyl)methyl]-4-[1-(4-fluorophenyl)cyclopentyl]-;

5-pyrimidinecarboxamide, 4-[1-(4-fluorophenyl)cyclopentyl]-N-[[3-fluoro-5-(trifluoromethyl)phenyl]methyl]-2-[(4-methylcyclohexyl)amino]-;

5-pyrimidinecarboxamide, 4-[1-(4-fluorophenyl)cyclopentyl]-N-[[3-fluoro-5-(trifluoromethyl)phenyl]methyl]-2-(1-pyrrolidinyl)-;

5-pyrimidinecarboxamide, 4-[1-(4-fluorophenyl)cyclopentyl]-N-[[3-fluoro-5-(trifluoromethyl)phenyl]methyl]-2-(4-methyl-1-piperazinyl)-;

5-pyrimidinecarboxamide, 4-[1-(4-fluorophenyl)cyclopentyl]-N-[[3-fluoro-5-(trifluoromethyl)phenyl]methyl]-2-(3-methyl-1-piperidinyl)-;

5-pyrimidinecarboxamide, 4-[1-(4-fluorophenyl)cyclopentyl]-N-[[3-fluoro-5-(trifluoromethyl)phenyl]methyl]-2-(4-methyl-1-piperidinyl)-;

5-pyrimidinecarboxamide, 4-[1-(4-fluorophenyl)cyclopentyl]-N-[[3-fluoro-5-(trifluoromethyl)phenyl]methyl]-2-[(1-methylpropyl)amino]-;

5-pyrimidinecarboxamide, 2-(cyclopentylamino)-4-[1-(4-fluorophenyl)cyclopentyl]-N-[[3-fluoro-5-(trifluoromethyl)phenyl]methyl]-;

5-pyrimidinecarboxamide, 4-[1-(4-fluorophenyl)cyclopentyl]-N-[1-(4-fluorophenyl)ethyl]-2-[(4-methylcyclohexyl)amino]-;

5-pyrimidinecarboxamide, 4-[1-(4-fluorophenyl)cyclopentyl]-N-[1-(4-fluorophenyl)ethyl]-2-(1-pyrrolidinyl)-;

5-pyrimidinecarboxamide, 4-[1-(4-fluorophenyl)cyclopentyl]-N-[1-(4-fluorophenyl)ethyl]-2-(4-methyl-1-piperazinyl)-;

5-pyrimidinecarboxamide, 4-[1-(4-fluorophenyl)cyclopentyl]-N-[1-(4-fluorophenyl)ethyl]-2-(3-methyl-1-piperidinyl)-;

5-pyrimidinecarboxamide, 4-[1-(4-fluorophenyl)cyclopentyl]-N-[1-(4-fluorophenyl)ethyl]-2-(4-methyl-1-piperidinyl)-;

5-pyrimidinecarboxamide, 4-[1-(4-fluorophenyl)cyclopentyl]-N-[1-(4-fluorophenyl)ethyl]-2-[(1-methylpropyl)amino]-;

5-pyrimidinecarboxamide, 2-(cyclopentylamino)-4-[1-(4-fluorophenyl)cyclopentyl]-N-[1-(4-fluorophenyl)ethyl]-; and 5-pyrimidinecarboxamide, 4-[1-(4-fluorophenyl)cyclopentyl]-2-(4-methyl-1-piperidinyl)-N-[[4-(trifluoromethyl)phenyl]methyl]-;

or a pharmaceutically acceptable salt thereof.

8. A compound of claim 1 where X is propylene.

9. A composition comprising a therapeutically effective amount of a compound of claim 1 and a pharmaceutically acceptable carrier.

10. A method of treating memory impairment comprising administering a therapeutically effective amount of a compound of claim 1 and a pharmaceutically acceptable carrier to a patient.

* * * * *